United States Patent
Walsh et al.

(10) Patent No.: US 8,236,976 B2
(45) Date of Patent: Aug. 7, 2012

(54) PROCESSES FOR HIGHLY ENANTIO- AND DIASTEREOSELECTIVE SYNTHESIS OF ACYCLIC EPOXY ALCOHOLS AND ALLYLIC EPOXY ALCOHOLS

(75) Inventors: Patrick Walsh, Philadelphia, PA (US); Alice E. Lurain, Brooklyn, NY (US); Ann R. Kelly, Jenkintown, PA (US); Aaron G. Maestri, San Diego, CA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1029 days.

(21) Appl. No.: 10/592,075

(22) PCT Filed: Mar. 9, 2005

(86) PCT No.: PCT/US2005/007778
§ 371 (c)(1), (2), (4) Date: Feb. 10, 2009

(87) PCT Pub. No.: WO2005/087755
PCT Pub. Date: Sep. 22, 2005

(65) Prior Publication Data
US 2009/0163728 A1    Jun. 25, 2009

Related U.S. Application Data

(60) Provisional application No. 60/551,482, filed on Mar. 9, 2004, provisional application No. 60/610,491, filed on Sep. 16, 2004.

(51) Int. Cl.
C07D 301/03    (2006.01)
C07D 301/14    (2006.01)

(52) U.S. Cl. ..................... 549/525; 549/524

(58) Field of Classification Search ............. 549/524, 549/525
See application file for complete search history.

(56) References Cited

U.S. PATENT DOCUMENTS
4,764,628 A    8/1988    Shum

OTHER PUBLICATIONS

H. J. Reich, Organic Chemistry Acronyms, 2002, p. 3.*
Kilpin et al, Organogold(III) complexes containing chelating bis(amidate)ligands: synthesis, characterization and biological activity, 2007, abstract p. 1.*
T. Ayad et al., "A new diorganozinc-based enantioselective access to truncated D-ribo-phytosphingosine", Tetrahedron Letters, 44: 570-582 (2003).
G. Righi et al., "A Study on the "Non-Chelation Controlled" Organometallic Addition to trans alpha,beta-Epoxy Aldehydes—A Straightforward Stereoselective Synthesis of the Abbot Amino Dihydroxyethylene Dipeptide Isoster", Eur. J. Org. Chem., 1573-1577 (2002).
P.R. Krishna et al., "Diastereoselective Baylis-Hillman reaction: first use of chiral 2,3-epoxy aldehydes as novel electrophiles", Tetrahedron Letters, 45: 7847-7850 (2004).
K. Soai et al., "Enantioselective Addition of Organozinc Reagents to Aldehydes", Chem. Rev., 92: 833-856 (1992).
A. Lurain et al., "One-Pot Asymmetric Synthesis of Acyclic Chiral Epoxy Alcohols via Tandem Vinylation-Epoxidation with Dioxygen", J. Org. Chem., 70: 1262-1268 (2005).
C. Garcia et al., "A One-Pot Diastereoselective Synthesis of cis-3-Hexene-1,6-diols via an Unusually Reactive Organozinc Intermediate", J. Am. Chem. Soc., 125: 3210-3211 (2003).
L. Pu et al., "Catalytic Asymmetric Organozinc Additions to Carbonyl Compounds", Chem. Rev., 101: 757-824 (2001).
W. Adam et al., "Diastereoselective Catalytic Epoxidation of Chiral Allylic Alcohols by the TS-1 and Ti-B zeolites: Evidence for a Hydrogen-Bonded, Peroxy-Type Loaded Complex as Oxidizing Species", J. Org. Chem., 62: 3631-3637 (1997).
A. E. Lurain et al., "Highly Enantio- and Diastereoselective One-Pot Synthesis of Acyclic Epoxy Alcohols with Three Contiguous Stereocenters", J. Am. Chem Soc., 126: 13608-13609 (2004).
F. Fringuelli et al., "Regioselective Epoxidation of Allylic Alcohols with Monoperoxyphthalic Acid in Water", J. Org. Chem., 57: 1198-1202 (1992).

* cited by examiner

*Primary Examiner* — Taylor Victor Oh
(74) *Attorney, Agent, or Firm* — Patrick J. Hagan; Dann, Dorfman, Herrell and Skillman, P.C.

(57) ABSTRACT

The inventive subject matter relates to novel processes for making an epoxy alcohol from an aldehyde, comprising the steps of: (a) adding (i) an organozinc compound or (ii) divinylzinc compound and an diorganozinc compound to said aldehyde in the presence of a first catalyst to form an allylic alkoxide compound; and (b) epoxidizing said allylic alkoxide compound in the presence of an oxidant and a second catalyst.

13 Claims, No Drawings

PROCESSES FOR HIGHLY ENANTIO- AND DIASTEREOSELECTIVE SYNTHESIS OF ACYCLIC EPOXY ALCOHOLS AND ALLYLIC EPOXY ALCOHOLS

This application claims the benefit of U.S. Provisional Patent Application Nos. 60/551,482, filed Mar. 9, 2004, and 60/610,491, filed Sep. 16, 2004, the contents of which are hereby incorporated by reference in their entirety.

This work was supported in part by National Science Foundation grant CHE-0315913 and National Institutes of Health, National Institute of General Medicine, grant GM58101. The United States government may have rights in the inventive subject matter by virtue of this support.

BACKGROUND OF THE INVENTIVE SUBJECT MATTER

1. Field of Inventive Subject Matter

The inventive subject matter relates to novel processes for making an epoxy alcohol from an aldehyde, comprising the steps of: (a) adding (i) an organozinc compound or (ii) a divinylzinc compound and an diorganozinc compound to said aldehyde in the presence of a first catalyst to form an allylic alkoxide compound; and (b) epoxidizing said allylic alkoxide compound in the presence of an oxidant and a second catalyst.

2. Background

Epoxides are important intermediates in organic synthesis, as their reactive nature facilitates transformation into many classes of compounds under mild conditions. Epoxy alcohols contain three reactive sites for further elaboration: the carbon bearing the hydroxyl and the two carbons of the oxirane ring. From a synthetic point of view, the large range of possibilities for the three active sites of an epoxy alcohol, which could eventually lead to three consecutive stereogenic centers, makes the epoxy alcohols the most versatile compounds obtained by oxidative olefin methodology. The ability to functionalize epoxy alcohols with excellent control over regiochemistry is what makes these intermediates so valuable. Applicants have developed new methods to prepare epoxy alcohols, most of which are not easily accessible using known methods.

Medications sold as single enantiomers comprise 50 of the 100 top selling drugs, and represent an industry of well over 100 billion dollars per year. The precursors of these medications are chiral substances of high optical purity, which constitute an important class of starting materials for organic and medicinal chemists. Using the stereochemistry of these materials to control generation of subsequent stereogenic centers allows the preparation of biologically and medicinally important target molecules as single enantiomers. Organic compounds of very high optical purity are essential for testing and evaluation of biological activity, because each enantiomer can interact with a distinct site in an organism and elicit very different responses.

Chemical and medical scientists have understood the significance of producing drugs as single enantiomers for many years. As chemists have honed their ability to generate chiral molecules and efficiently analyze their enantiopurity, the FDA has encouraged the pharmaceutical industry to introduce medications as single enantiomers. As a result of the FDA's actions, medications are increasingly being synthesized, tested, and sold as single enantiomers.

The production of medications as single enantiomers has been accomplished primarily by four different techniques: 1) use of natural sources as starting materials, 2) resolution of racemates, 3) chiral auxiliary chemistry, and 4) asymmetric catalysis. Increasingly, the use of chiral catalysts is displacing the application of chiral reagents and chiral auxiliaries in the asymmetric synthesis of natural and unnatural products. An active asymmetric catalyst enables the chemist to prepare large quantities of material with high enantiopurity from small amounts of enantiopure material, without the need to cleave and recover the chiral auxiliary. Despite the recent advances in asymmetric synthesis, many formidable challenges remain. Predominant among these is the development of methods that enable rapid increases in molecular complexity with minimal isolation and purification. Such multicomponent tandem reactions are in high demand, because they enhance synthetic efficiency and facilitate diversity oriented synthesis. The development of experimentally simple, efficient, and highly enantio- and diastereoselective catalysts for the generation of C—C and C—O bonds in chiral epoxy alcohols is a principal result of the inventive subject matter.

Enantioenriched epoxy alcohols are among the most versatile and utile intermediates in asymmetric organic synthesis. These substrates readily undergo regio- and stereoselective ring-opening reactions with a wide array of nucleophiles. As a result, they have been employed frequently in the synthesis of natural and non-natural products. Much interest has been shown, therefore, in developing regio- and stereoselective synthetic methods for this class of compounds. In the prior art, chiral epoxy alcohols have typically been synthesized by selective epoxidation of the corresponding allylic alcohols, a process which can take place under reagent control, in the case of achiral allylic alcohols, or under substrate control, in the case of chiral allylic alcohols.

The Sharpless-Katsuki epoxidation. The history of the Sharpless-Katsuki epoxidation and its impact on synthetic organic chemistry and asymmetric catalysis is well known. The titanium catalyzed asymmetric epoxidation of allylic alcohols has remained virtually unchanged and unchallenged since its discovery in 1980. As shown in Scheme P-1, the Sharpless-Katsuki epoxidation involves a combination of substoichiometric titanium tetraisopropoxide, tert-butyl hydroperoxide (TBHP), a dialkyl tartrate ligand, and an achiral allylic alcohol. The reaction gives excellent enantioselectives for a variety of allylic alcohols (usually >90%), as demonstrated by hundreds of reported applications of this reaction in the last twenty years. Either enantiomer of the epoxy alcohol can be easily prepared, because both enantiomers of the ligands are commercially available.

Scheme P-1. Sharpless-Katsuki Epoxidation

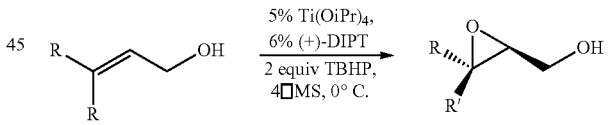

As the Sharpless-Katsuki epoxidation became widely employed, the chemistry of 2,3-epoxy alcohols was greatly expanded.

Particularly relevant to the inventive subject matter is the use of a Sharpless-Katsuki epoxidation catalyst with allylic alcohols containing a preexisting stereocenter at the carbanol carbon, as shown in Scheme P-2. In the kinetic resolution ("KR") of racemic allylic alcohols, one enantiomer of the substrate is epoxidized much faster than the other, with $k_{fast}/k_{slow}$ (defined as $k_{rel}$) often over 50. Although it is usually the resolved allylic alcohol that is desired, the epoxy alcohol can be obtained with good enantio- and diastereoselectivity in most cases. The erythro diastereomer is formed when the substrate and catalyst are matched, whereas the mismatched combination usually gives either the threo or erythro diastereomer with low diastereoselectivity. The major drawbacks to the Sharpless-Katsuki method are 1) the racemic allylic alcohol must be synthesized, isolated, and purified beforehand, 2) the maximum yield in any kinetic resolution is 50%, and 3)

the epoxy alcohol product can be difficult to separated from the unreacted allylic alcohol. Related epoxy alcohols have also been prepared by oxidation of 2,3-epoxy alcohols to the aldehyde, followed by addition of an organometallic reagent. Mixtures of diastereomers are observed in most of these reactions. The inventive subject matter addresses these disadvantages directly, and is complementary to the Sharpless-Katsuki KR in that the threo diastereomer is formed, in contrast to the erythro diastereomer under Sharpless conditions.

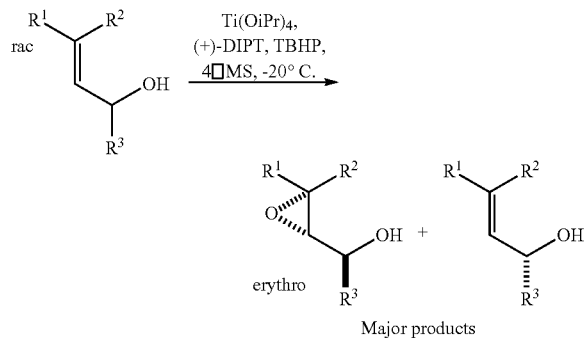

Scheme P-2. Sharpless-Katsuki kinetic resolution of allylic alcohols.

Currently, the asymmetric epoxidation introduced by Sharpless and Katsuki, is the foremost method for synthesizing epoxy alcohols from prochiral allylic alcohols. The Sharpless-Katsuki asymmetric epoxidation employs catalytic titanium tetraisopropoxide, tartrate ester ligands, 4 Å molecular sieves, and tert-butyl hydroperoxide (TBHP) in the construction of enantioenriched epoxy alcohols. The ability to efficiently synthesize these useful chiral building blocks led to new synthetic disconnections and, thereby, transformed the approaches taken to synthesize natural products, making it one of the most useful reactions in organic synthesis.

In contrast to the synthesis of epoxy alcohols from prochiral allylic alcohols, the synthesis of epoxy alcohols containing a stereogenic center at the carbinol carbon from achiral materials requires that three contiguous stereocenters be generated diastereo- and enantioselectively. This transformation is currently performed in a two-step process involving synthesis, isolation, and purification of the enantioenriched allylic alcohol, followed by a directed epoxidation.

Further, the Sharpless-Katsuki KR has significant limitations. As with all kinetic resolutions, the isolated yield of the epoxy alcohol product can be no greater than 50%, and in most cases, it is significantly less. This transformation is performed on a racemic allylic alcohol, and the resulting enantioenriched starting material and the epoxy alcohol product must be separated by column chromatography. In order to obtain the epoxy alcohol with high enantiomeric excess ("ee"), the reaction must be quenched at low conversion, because the ee of the epoxy alcohol decreases over the course of the KR. The epoxy alcohol is therefore not usually obtained directly from the Sharpless KR; rather the enantioenriched allylic alcohol is first isolated. After purification, the allylic alcohol is subjected to a directed epoxidation to yield the desired epoxy alcohol. The lack of efficient methods for the synthesis of this class of epoxy alcohols has prevented their widespread implementation as key intermediates in organic synthesis. An alternate approach to the Sharpless-Katsuki KR is therefore required.

Epoxidation of the isolated enantioenriched secondary allylic alcohols is generally performed using an organic peracid, such as meta-chloroperbenzoic acid (mCPBA), or with a transition-metal catalyst in combination with a stoichiometric oxidant. Good to excellent diastereoselectivities have been achieved with cyclic allylic alcohols using a wide range of oxidizing agents. Acyclic allylic alcohols have proven to be a more synthetically challenging class of chiral building blocks, because the increased conformational freedom permits directed epoxidation to occur at both diastereotopic faces of the olefin.

In the prior art, cyclic allylic alcohols and acyclic allylic alcohols having substitution on the olefin such that significant $A^{1,3}$ or $A^{1,2}$ strain exists in one of the diastereomeric transition states have been produced with good to excellent diastereoselectivities. Thus, $A^{1,3}$ strain encountered in the transition state leading to the minor diastereomer can result in high diastereoselectivity for allylic alcohols that are Z-substituted with respect to the carbanol moiety. Likewise, substrates with substitution geminal to the carbanol group can exhibit $A^{1,2}$ strain in one of the diastereomeric transition states and be epoxidized with high diastereoselectivity. In the prior art, allylic alcohols containing disubstituted (E)-olefins were among the most difficult substrates for directed epoxidation. In the absence of significant $A^{1,3}$ and/or $A^{1,2}$ strain in the diastereomeric transition states, diastereoselectivities for these substrates were typically less than 2:1 with both peracid- and transition-metal catalyzed epoxidation reactions.

As shown in Scheme P-3, we expected that the peracid associates with the allylic alcohol via hydrogen bonding with a dihedral angle of approximately 120°, while in the case of vanadium- and titanium-based peroxide catalysts, the binding of the allylic alkoxide to the metal is expected to favor a dihedral angle of 40-50° and 70-90°, respectively. This dihedral angle determines the spatial relationships between the substituents on the olefin (R2, R3, and R4) and the substituent at the stereogenic center (R1) in the transition state. Therefore, the preferred diastereomer of the product epoxy alcohol and the extent to which it dominates may differ for a given allylic alcohol substrate, depending upon the epoxidizing agent used. For any given epoxidizing agent, the favored diastereomer is dictated by the substitution pattern of the allylic alcohol, which determines whether $A^{1,2}$ or $A^{1,3}$ strain is the dominant steric interaction in the transition state.

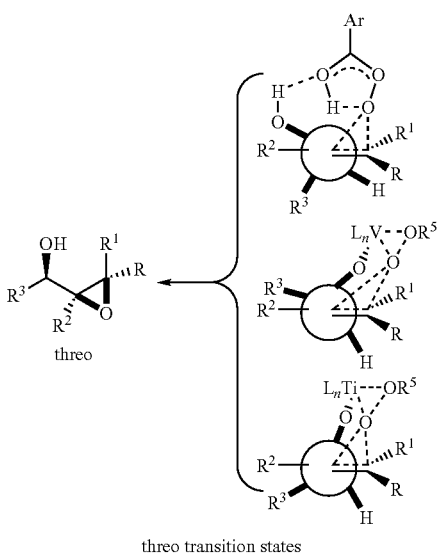

Scheme P-3
Transition states for the directed epoxidation of chiral allylic alcohols via peracid or transition metal peroxides threo transition states -continued

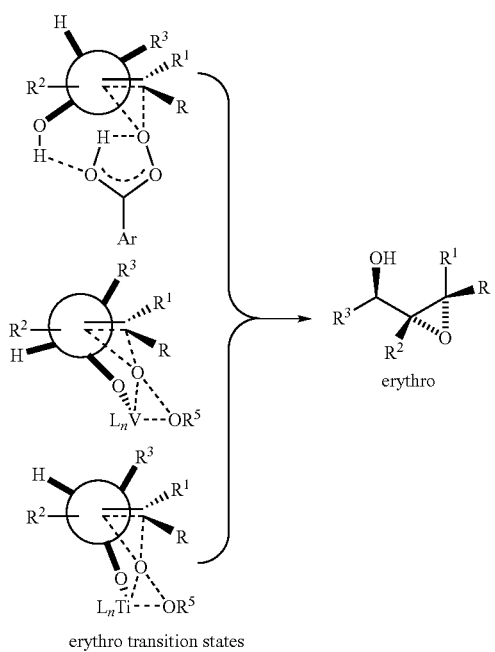

erythro transition states

In the inventive subject matter, titanium catalysts are preferentially employed. When R=alkyl and $R^1$=$R^2$=H, there is no $A^{1,2}$ or $A^{1,3}$ strain in either transition state.

Thus, substitution on the olefin, such that significant $A^{1,2}$ or $A^{1,3}$ strain exists in one of the diastereomeric transition states, can lead to strong preference for formation of one diastereomer over the other; however, the degree of selectivity is dictated by the type of oxidant used (Table P-1). In the case where $A^{1,3}$ strain exists in one of the diastereomeric transition states, the threo diastereomer predominates (Table P-1, entries 1 and 2). On the other hand, the major diastereomer is the erythro in the case where $A^{1,2}$ strain is present in one of the diastereomeric transition states (Table P-1, compound 3). With trans-disubstituted olefins, there is no significant source of allylic strain in either diastereomeric transition state. This leads to low diastereoselectivities, with neither the erythro nor the threo diastereomer consistently predominating (Table P-1, compound 4).

TABLE P-1

Diastereomeric ratios for the directed epoxidation of chiral secondary allylic alcohols with various oxidizing agents.

| | | Diastereomeric Ratios (erthyro:threo) | | |
| --- | --- | --- | --- | --- |
| Entry | Substrate | $Ti(O^iPr)_4$ t-BuOOH | $VO(acac)_2$ t-BuOOH | mCPBA |
| 1 | (cis-pentenol) OH | 1:10 | 1:2.4 | 1:19 |
| 2 | (prenol-type) OH | 1:19 | 1:6.1 | 1:19 |
| 3 | (1,1-disub vinyl) OH | 3.5:1 | 19:1 | 1.2:1 |
| 4 | (trans-pentenol) OH | 1:1.9 | 2.4:1 | 1:1.8 |

Differences in diastereoselectivity for a given allylic alcohol or allylic alkoxide substrate with different epoxidation methods can be explained by examination of the degree of allylic strain in the diastereomeric epoxidation transition states. The dihedral angle, C=C—C—O, of the substrate determines the spatial relationships between the substituents on the olefin ($R^2$, $R^3$ and $R^4$) and the substituent at the stereogenic center ($R^1$) in the transition states (Scheme P-4). The two diastereomeric transition states for epoxidation with $Ti(O^iPr)_4$/TBHP are shown in Scheme P-4. For that system, the titanium peroxide catalyst binds to the allylic alkoxide and delivers the oxidant with a dihedral angle of 70°-90°. This leads to $Ti(O^iPr)_4$/TBHP being more diastereoselective in the case of $A^{1,3}$ strain (Table P-1, entries 1, 2) than in the case of $A^{1,2}$ strain (compound 3).

Scheme P-4
Diasteromeric epoxidation transition states for the titanium-peroxide catalyst

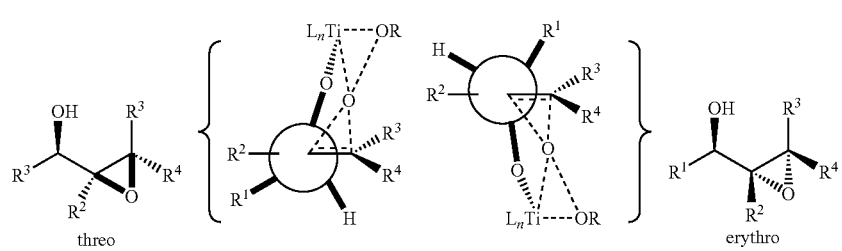

Sharpless has previously demonstrated the application of the KR to a bis(allylic alcohol) for the synthesis of an allylic epoxy alcohol (Scheme P-5). In that case, the starting material, a racemic bis(allylic alcohol), has eight different olefinic faces at which epoxidation can occur. The relative rate of epoxidation of a disubstituted versus a monosubstituted allylic olefin with the Sharpless catalyst is sufficiently large in this example such that high selectivity is observed for the more electron rich, disubstituted double bond. Although this reaction displays the power of the Sharpless catalyst, the yield and synthetic efficiency remain low.

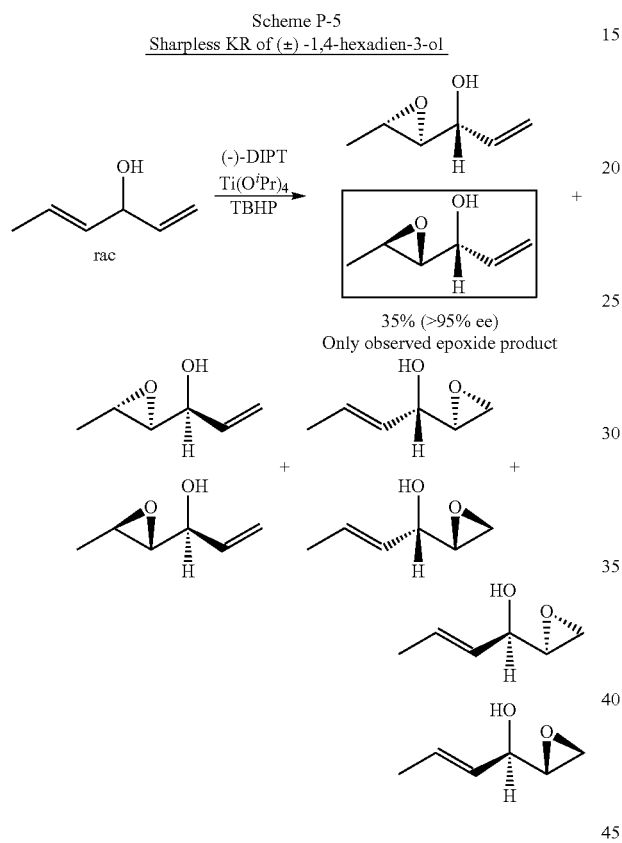

Epoxy alcohols bearing additional functionality, such as allylic epoxy alcohols, are of interest for their increased synthetic potential in the construction of natural products. These compounds contain three different functional groups: an olefin, a carbinol, and the epoxide. This increased functionality makes them especially useful intermediates, but it also makes their synthesis more difficult. As in the case of the epoxy alcohol substrates discussed previously, the issues of enantio- and diastereoselectivity for the generation of three contiguous stereocenters must be addressed. In addition, there are chemoselectivity issues involving differentiation of the two allylic double bonds in the synthesis of allylic epoxy alcohols.

Jacobsen-Katsuki epoxidation. Ten years after the seminal work of Sharpless and Katsuki, Jacobsen and Katsuki introduced catalysts for the epoxidation of isolated olefins based on (salen)Mn complexes, as shown in Scheme P-6. A variety of oxidants can be employed in the epoxidation reaction, with NaOCl and iodosylbenzene being most common. Additives such as N-oxides prolong catalyst lifetimes and increase enantioselectivities. The best substrates are conjugated (Z)-disubstituted olefins, while (E)-isomers give lower enantioselectivities. Terminal olefins remain a challenging class of substrates for these catalysts. It has been found that the (salen) Cr-based catalysts exhibit higher levels of enantioselectivity with (E)-disubstituted olefins, while a (salen)Ru(NO) system introduced by Katsuki exhibited high enantioselectivities with (E)- and (Z)-conjugated olefins.

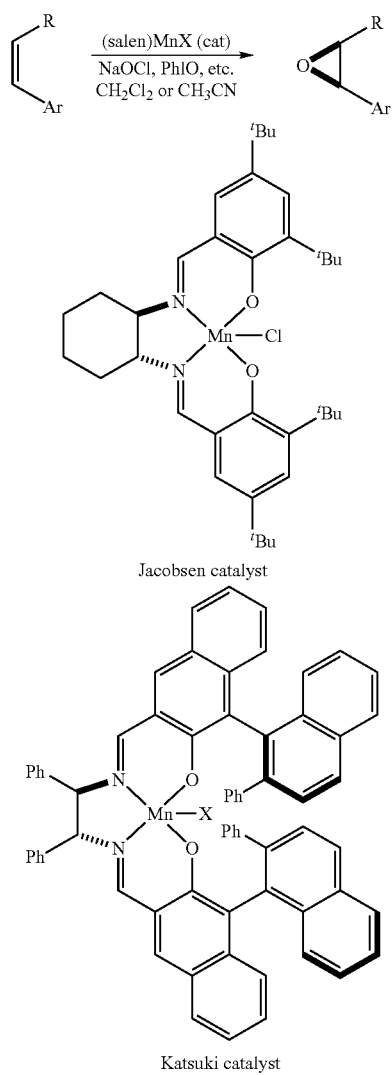

An excellent catalyst has been introduced by Jacobsen and coworkers for the kinetic resolution of terminal epoxides. These catalysts, based on (salen)Co(OAc), exhibit very large relative rates of reaction with enantiomeric epoxides.

Chiral dioxirane epoxidation catalysts. A drawback of the (salen)Mn-based catalysts of Jacobsen and Katsuki is the low levels of enantioselectivity with (E)-disubstituted olefins. It was found, however, that (E)-disubstituted olefins were excellent substrates for dioxirane-based catalysts. A catalyst was developed based on a chiral ketone that can be synthesized in two steps from D-fructose (see Scheme P-7, compound A). The enantiomeric form can be prepared from L-sorbose in 5 steps. This catalyst, which can be used with oxone or hydrogen peroxide as the oxidant is tolerant of a variety of functional groups. The N-Boc derivative (see Scheme P-7, compound B) exhibits good levels of enantioselectivity with (Z)-disubstituted olefins. Other ketone derivatives do not appear to be as efficient or enantioselective.

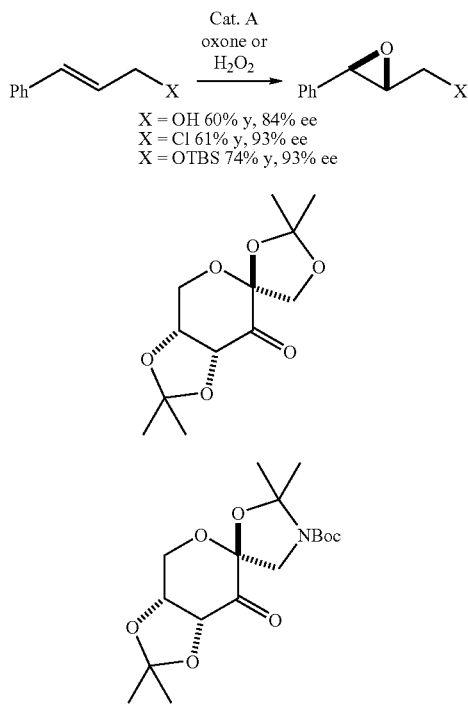

Scheme P-7
Shi epoxidation catalysts for (E)-olefins (A) and (Z)-olefins (B).

Epoxidation of α,β-unsaturated enones and related compounds. The epoxidation of α,β-unsaturated ketones and related carbonyl compounds has been an active area of research in recent years. This epoxidation involves the 1,4-addition of a peroxide to the enone followed by collapse of the intermediate enolate. A variety of catalysts will promote this reaction, including polyleucine catalysts, phase transfer catalysts, lanthanide-BINOL-based catalysts, and main group catalysts. A system involving the stoichiometric epoxidation of enones and nitro alkenes with three equivalents of (R,R)-N-methylpseudoephedrine is noteworthy, because this was the first highly enantioselective epoxidation reactions using diethylzinc and dioxygen to generate the oxidant (see Scheme P-8)

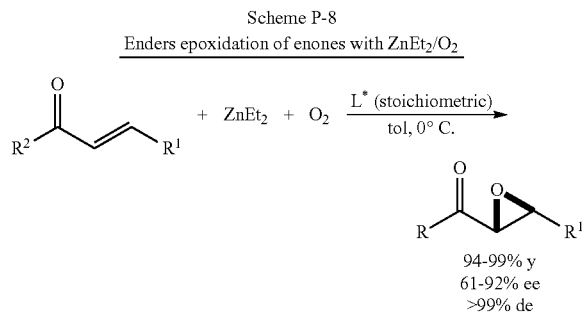

Scheme P-8
Enders epoxidation of enones with ZnEt$_2$/O$_2$

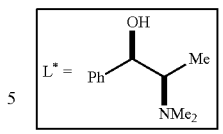

The reaction of diethylzinc with oxygen has had a long and controversial history, and mechanistic work to determine the nature of the oxidation products continues today. The reaction is believed to proceed by insertion of dioxygen into a Zn—C bond to give a zinc peroxy species (see Scheme P-9). In the Enders system, combination of the amino alcohol ligand and diethylzinc in a 1:1 ratio before exposure to dioxygen will not leave any diethylzinc to react with the dioxygen. It was proposed, therefore, that the oxidant in this reaction is zinc bearing the peroxide and the chiral amino alkoxide ligand. This ZnEt$_2$/O$_2$ oxidation reaction was later utilized for the epoxidation of enones a with stoichiometric BINOL polymer. Moderate enantioselectivities and high diastereoselectivities were observed with this system. As shown in Scheme P-9, in cases where there is an excess of dialkylzinc, the oxidant is likely the ethylzinc peroxide, Et-Zn—OOEt. Other mechanistic investigations also support the generation of Et-Zn—OOEt.

Scheme P-9
Formation of zinc peroxides in the Enders epoxidation of enones (upper) and reaction of diethylzinc with dioxygen to generate the alkyl zinc peroxide (lower)

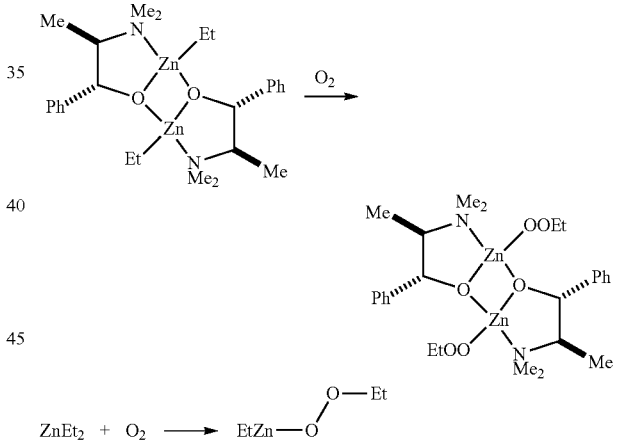

Improved methods to synthesize functionalized epoxides are in high demand, because epoxides are among the most valuable and versatile chiral intermediates in organic synthesis. Epoxy alcohols containing three contiguous stereocenters have not been previously prepared directly from achiral starting materials. The inventive subject matter expands the classes of epoxy alcohols that are synthetically accessible.

In our early work on the synthesis of epoxy alcohols with three contiguous stereocenters, we generated allylic alkoxides with substituents on the olefin that led to $A^{1,2}$ or $A^{1,3}$ strain in one of the diastereomeric transition states. The allylic zinc alkoxide was formed via enantioselective addition of an alkylzinc reagent to an α,β-unsaturated aldehyde or via an asymmetric vinyl addition with a pre-formed divinylzinc species to a simple aldehyde. Subsequent epoxidation was performed using dioxygen and catalytic Ti(O$^i$Pr)$_4$ to provide the desired product with high enantio- and diastereoselectivity. In the absence of either $A^{1,2}$ or $A^{1,3}$ strain, moderate diastereoselectivities were obtained.

In our later work, we have expanded the versatility of our one-pot process for the synthesis of epoxy alcohols with three contiguous stereocenters from prochiral starting materials. We now demonstrate that this method is applicable to the synthesis of densely functionalized allylic epoxy alcohols with high enantio-, diastereo-, and chemoselectivity. Additionally, we describe a procedure whereby TBHP can be substituted for dioxygen in the diastereoselective epoxidation step. This new inventive process for tandem addition/diastereoselective epoxidation reactions allows greater control in the oxidation step and is more amenable to scale-up.

Thus, Applicants have developed a highly enantio- and diastereoselective method to synthesize acyclic epoxy alcohols with three contiguous stereocenters in good to excellent yields. The inventive process entails an enantioselective C—C bond-forming reaction to generate allylic alkoxides that are subsequently epoxidized diastereoselectively via a directed epoxidation using standard oxidants. In this process, three new bonds are formed, allowing efficient assembly of complex chiral building blocks. The advantages of these methods are 1) that they circumvent the need to prepare and isolate either racemic or enantioenriched allylic alcohols, 2) the oxidant is generated under the reaction conditions from organozinc reagents and dioxygen, 3) the enantio- and diastereoselectivities are very high for almost all classes of substrates, and 4) the asymmetric C—C bond-forming step can be catalyzed by literally hundreds of catalysts. Like the epoxy alcohols prepared by the Sharpless asymmetric epoxidation, we anticipate that the epoxy alcohols described here will find widespread utility in enantioselective synthesis.

SUMMARY OF THE INVENTIVE SUBJECT MATTER

The inventive subject matter relates to a highly enantio- and diastereoselective process for making an epoxy alcohol from an aldehyde, comprising the steps of:

(a) adding (i) an organozinc compound or (ii) a divinylzinc compound and an diorganozinc compound to said aldehyde in the presence of a first catalyst to form an allylic alkoxide compound; and (b) epoxidizing said allylic alkoxide compound in the presence of an oxidant and a second catalyst.

DETAILED DESCRIPTION OF THE INVENTIVE SUBJECT MATTER

Definitions

The term "isomers" refer to different compounds that have the same molecular formula. "Stereoisomers" are isomers that differ only in the way the atoms are arranged in space. "Enantiomers" are a pair of stereoisomers that are non-superimposable mirror images of each other. "Diastereoisomers" are stereoisomers which are not mirror images of each other. "Racemic mixture" means a mixture containing equal parts of individual enantiomers. "Non-racemic mixture" is a mixture containing unequal parts of individual enantiomers or stereoisomers.

The term "organozinc compounds" refers to compounds of the general formula R—Zn—X, where R is an organic moiety such as an alkyl, and X is an organic moiety such as R or a halide group.

The term "aldehyde" is used generally herein as understood in the chemical arts, to refer to a class of highly reactive organic chemical compounds obtained by oxidation of primary alcohols, and having the general formula R—CHO. In particular, preferred aldehydes herein are α,β-unsaturated aldehydes and have the formula

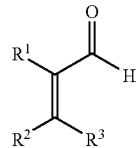

where the $R^1$, $R^2$, and $R^3$ groups are as disclosed herein.

Process for Making an Epoxy Alcohol

The inventive subject matter relates to highly enantio- and diastereoselective processes for making an epoxy alcohol from an aldehyde.

Epoxy alcohols are extremely useful compounds in asymmetric organic synthesis and have been employed extensively in the assembly of natural products. Applicants describe a highly enantio- and diastereoselective one-pot method for the efficient synthesis of synthetically useful acyclic epoxy alcohols and allylic epoxy alcohols. Our method takes advantage of highly enantioselective C—C bond-forming reactions to set the initial chirality. The resulting allylic zinc alkoxide intermediate is then epoxidized in situ using an oxidant such as dioxygen or TBHP, in the presence of a titanium tetraalkoxide. Epoxy alcohols with up to three contiguous stereocenters are formed in one pot with excellent enantio- and diastereoselectivity. In cases where zinc alkoxide intermediates contain two different allylic olefins, the more electron-rich double bond is chemoselectively epoxidized to afford an allylic epoxy alcohol. The inventive methods represent a highly efficient, stereoselective, and chemoselective approach to the synthesis of a wide range of useful epoxy alcohol and allylic epoxy alcohol products that were previously difficult to access.

In our early work on the synthesis of epoxy alcohols with three contiguous stereocenters, we generated allylic alkoxides with substituents on the olefin that led to $A^{1,2}$ or $A^{1,3}$ strain in one of the diastereomeric transition states. The allylic zinc alkoxide was formed via enantioselective addition of an alkylzinc reagent to an α,β-unsaturated aldehyde or via an asymmetric vinyl addition with a pre-formed divinylzinc species to a simple aldehyde. Subsequent epoxidation was performed using dioxygen and catalytic Ti(O$^i$Pr)$_4$ to provide the desired product with high enantio- and diastereoselectivity. In the absence of either $A^{1,2}$ or $A^{1,3}$ strain, moderate diastereoselectivities were obtained.

In our later work, we have expanded the versatility of our one-pot process for the synthesis of epoxy alcohols with three contiguous stereocenters from prochiral starting materials. We now demonstrate that this method is applicable to the synthesis of densely functionalized allylic epoxy alcohols with high enantio-, diastereo-, and chemoselectivity. Additionally, we describe a procedure whereby TBHP can be substituted for dioxygen in the diastereoselective epoxidation step. This new inventive process for tandem addition/diastereoselective epoxidation reactions allows greater control in the oxidation step and is more amenable to scale-up.

In the inventive subject matter, we describe highly enantio- and diastereoselective methods to synthesize acyclic epoxy alcohols and allylic epoxy alcohols with three contiguous stereocenters from prochiral starting materials in good to excellent yields (Table 1). This one-pot two step process begins with a highly enantioselective C—C bond-forming reaction to install the initial chiral center of the allylic alkoxide (see Schemes 1 and 2). In the second step, the resulting allylic alkoxide is then diastereoselectively epoxidized in situ in the presence of a zinc peroxide species and a titanium tetraalkoxide.

The inventive subject matter employs several different methods for the first step in our one-pot procedure, the synthesis of the allylic alkoxide intermediate (Scheme 1, Routes A and B). The first of these is alkyl addition to enals promoted by one of three different ligand systems: two different bis (sulfonamide) ligands (Scheme 1, Route A, $L^*_1$ and $L^*_2$) and Nugent's (−)-MIB ($L^*_3$).[22] To demonstrate the ability of different catalyst systems to facilitate the initial C—C bond-forming reaction, various alkyl zincs were added to aldehydes asymmetrically in the presence of either MIB (Table 1, column 1) or one of 2 bis(sulfonamide) ligands (Table 1, column 2). Both catalyst systems have previously been shown to exhibit good enantioselectivities and yields for diethylzinc additions to aldehydes. The reaction times decreased from over 24 h for the amino alcohol ligand, MIB, to under 2 h with the bis(sulfonamide) ligands, $L^*_1$ and $L^*_2$. Both of the catalyst systems promoted the reaction with enantioselectivities >90%. (Table 1, entries 1-8).

Scheme 1
Two routes in the inventive one-pot asymmetric process
for the synthesis of epoxy alcohols

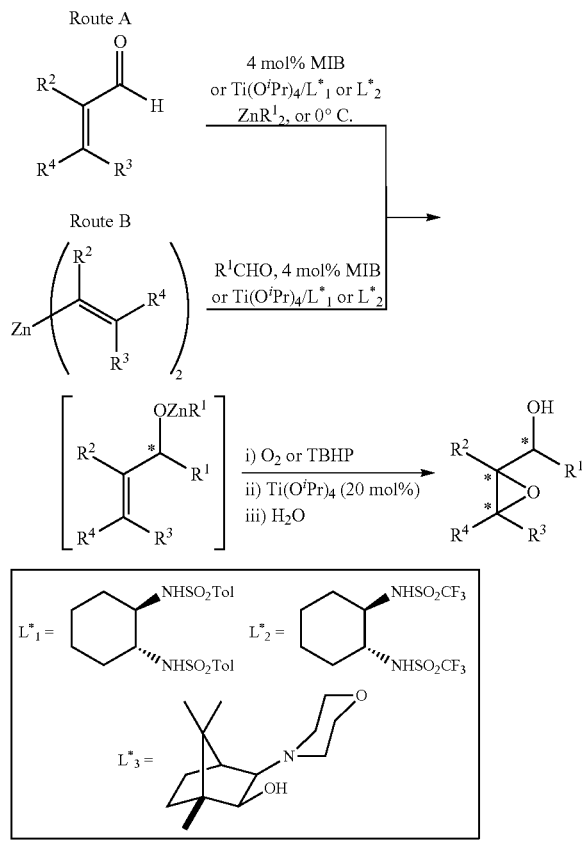

Scheme 2
Two routes in the inventive one-pot asymmetric process
for the synthesis of allylic epoxy alcohols

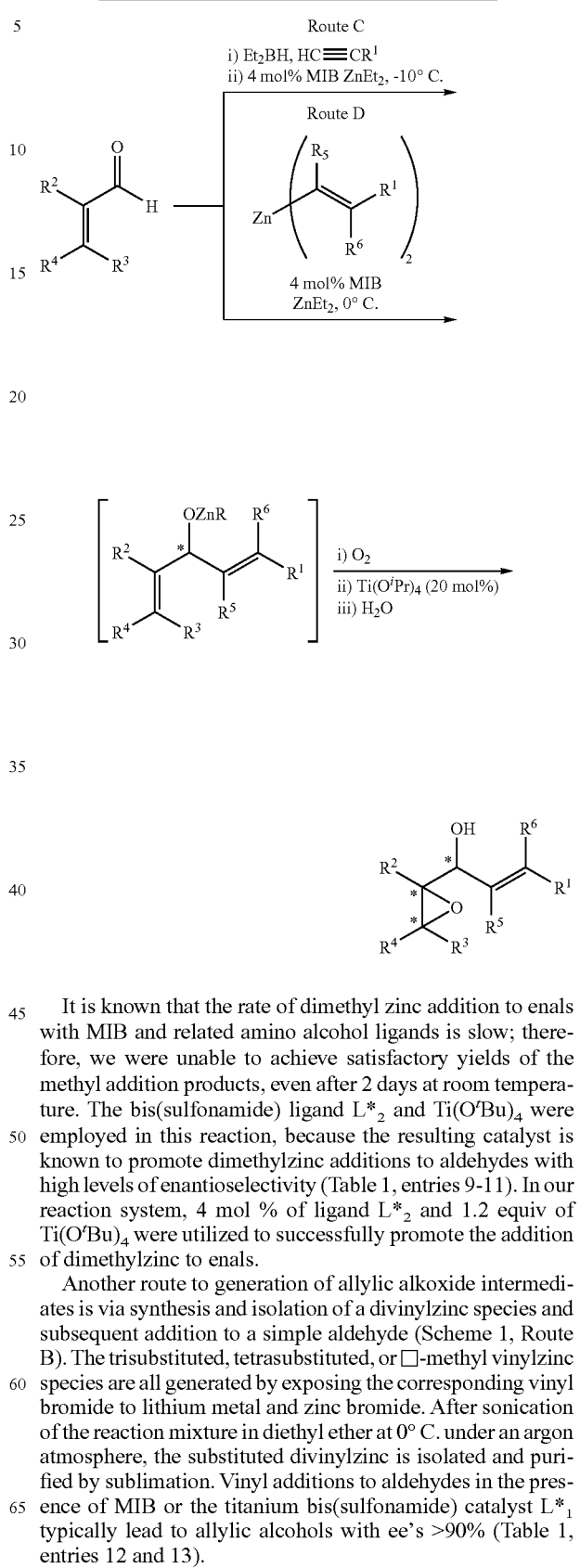

It is known that the rate of dimethyl zinc addition to enals with MIB and related amino alcohol ligands is slow; therefore, we were unable to achieve satisfactory yields of the methyl addition products, even after 2 days at room temperature. The bis(sulfonamide) ligand $L^*_2$ and Ti(O$^t$Bu)$_4$ were employed in this reaction, because the resulting catalyst is known to promote dimethylzinc additions to aldehydes with high levels of enantioselectivity (Table 1, entries 9-11). In our reaction system, 4 mol % of ligand $L^*_2$ and 1.2 equiv of Ti(O$^t$Bu)$_4$ were utilized to successfully promote the addition of dimethylzinc to enals.

Another route to generation of allylic alkoxide intermediates is via synthesis and isolation of a divinylzinc species and subsequent addition to a simple aldehyde (Scheme 1, Route B). The trisubstituted, tetrasubstituted, or □-methyl vinylzinc species are all generated by exposing the corresponding vinyl bromide to lithium metal and zinc bromide. After sonication of the reaction mixture in diethyl ether at 0° C. under an argon atmosphere, the substituted divinylzinc is isolated and purified by sublimation. Vinyl additions to aldehydes in the presence of MIB or the titanium bis(sulfonamide) catalyst $L^*_1$ typically lead to allylic alcohols with ee's >90% (Table 1, entries 12 and 13).

TABLE 1

Results for synthesis of epoxy alcohols with three contiguous stereocenters (Scheme 1, routes A and B)

| entry | aldehyde | epoxy alcohol[a] | L*$_3$, Ti(O$^i$Pr)$_4$ and O$_2$ | | L*$_1$ or L*$_2$, Ti(O$^i$Pr)$_4$ or Ti(O$^i$Bu)$_4$ and O$_2$ | | L*$_2$ or L*$_3$, Ti(O$^i$Pr)$_4$ or Ti(O$^i$Bu)$_4$ and TBHP | |
|---|---|---|---|---|---|---|---|---|
| | | | % ee[b] (% y) | [dr] | % ee[b] (% y) | [dr] | % ee[b] (% y) | [dr] |
| Scheme 3, Route A: Alkylzinc addtions to enals | | | | | | | | |
| 1 | (structure) | (structure) | 93 (60)[f] | [17:1] | 91 (89)[d] | [20:1] | 93 (65)[f] | [20:1] |
| 2 | (structure) | (structure) | 96 (65)[f] | [18:1] | 92 (90)[d] | [20:1] | 96 (79)[f] | [20:1] |
| 3 | (structure) | (structure) | 99 (90)[f] | [20:1] | 99 (91)[d] | [20:1] | 99 (82)[f] | [10:1] |
| 4 | (structure) | (structure) | 91 (96)[f] | [1:10] | 96 (60)[d] | [1:10] | 91 (60)[f] | [1:10] |
| 5 | (structure) | (structure) | 95 (96)[f] | [1:20] | 95 (93)[d] | [1:20] | 95 (98)[f] | [1:20] |
| 6 | (structure) | (structure) | 97 (62)[f] | [15:1] | 97 (85)[d] | [20:1] | 97 (74)[f] | [17:1] |
| 7 | (structure) | (structure) | 96 (81)[f] | [1:20] | 96 (86)[d] | [1:20] | 96 (83)[f] | [1:20] |
| 8 | (structure) | (structure) (CH$_2$)$_5$OTBDPS | 98 (86)[f] | [20:1] | 94 (80)[d] | [20:1] | 98 (85)[f] | [20:1] |
| 9 | (structure) | (structure) | | | 99 (78)[e] | [20:1] | 99 (89)[d] | [19:1] |

TABLE 1-continued

Results for synthesis of epoxy alcohols with three contiguous stereocenters (Scheme 1, routes A and B)

| | | | | | Diastereomeric Ratios (erythro:threo)[c] | | | |
|---|---|---|---|---|---|---|---|---|
| | | | L*[3], Ti(O$^i$Pr)$_4$ and O$_2$ | | L*[1] or L*[2], Ti(O$^i$Pr)$_4$ or Ti(O$^t$Bu)$_4$ and O$_2$ | | L*[2] or L*[3], Ti(O$^i$Pr)$_4$ or Ti(O$^t$Bu)$_4$ and TBHP | |
| entry | aldehyde | epoxy alcohol[a] | % ee[b] (% y) | [dr] | % ee[b] (% y) | [dr] | % ee[b] (% y) | [dr] |
| 10 | Ph-CH=CH-CHO | | | | 85 (89)[e] | [1:10] | 85 (65)[e] | [1:10] |
| 11 | (CH₃)₂C=CH-CHO | | | | 96 (60)[e] | [1:18] | 96 (72)[e] | [1:18] |
| Scheme 3, Route B: Vinylzinc addtions to aldehydes | | | | | | | | |
| 12 | p-tolyl-CHO | | 96 (82)[f] | [16:1] | 94 (89)[d] | [16:1] | 96 (90)[f] | [20:1] |
| 13 | cyclohexyl-CHO | | 90 (75)[f] | [1:19] | 97 (90)[d] | [1:20] | 90 (80)[f] | [1:20] |

[a]Stereochemistry indicated corresponds to that of the major diastereomer.
[b]Determined by chiral HPLC or GC analysis.
[c]Determined by $^1$H NMR analysis.
[d]Ligand L*[1] was used.
[e]Ligand L*[2] was used.
[f]Ligand L[3]* was used The second step of our one-pot process consists of diastereoselective epoxidation of the allylic zinc alkoxide intermediate in the presence of a zinc peroxide species and a titanium tetraalkoxide. As shown in Scheme 3, the first route to generation of the zinc peroxide species is by insertion of dioxygen into a zinc-alkyl bond. We have previously demonstrated that this zinc peroxide, in the presence of Ti(O$^i$Pr)$_4$ or Ti(O$^t$Bu)$_4$, epoxidizes the allylic alkoxide intermediate. Intramolecular oxygen atom transfer from the peroxide to the allylic alkoxide and hydrolysis of the reaction mixture, affords the epoxy alcohol product. Due to the practical difficulties associated with controlling the rate of delivery of dioxygen to reaction mixtures containing dialkylzinc reagents, an alternative route to the formation of a zinc peroxide was explored. TBHP is a commercially available stoichiometric oxidant that is commonly used in the transition-metal catalyzed epoxidations of allylic alcohols. As shown in Scheme 3, in our system, it is expected that TBHP would protonate an ethyl group on the organozinc reagent to yield ethane and an alkyl zinc t-butyl peroxide species.

When MIB was used as the ligand, in the asymmetric addition/diastereoselective epoxidation, a catalytic amount of titanium tetraisopropoxide was added (20 mol %) after the generation of the zinc peroxide species at −20° C. In the case of the titanium bis(sulfonamide)-based catalysts, the reaction mixture was simply cooled to −20° C. and exposed to the oxidant, TBHP or dioxygen.

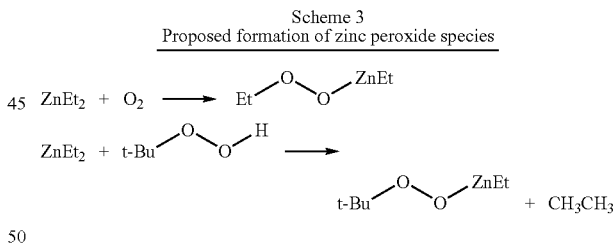

Scheme 3
Proposed formation of zinc peroxide species

The results of the asymmetric addition/diastereoselective epoxidation are shown in Table 1. Entries 1-11 have been synthesized via dialkylzinc additions to enals. The remaining entries were generated from vinylzinc addition to simple aldehydes. For the most part, in comparing columns 1 and 2 of Table 1 with column 3, the diastereoselectivities and yields are similar, regardless of whether the epoxidation step is carried out in the presence of dioxygen or TBHP. The yields tended to be slightly higher in the reactions with TBHP, as the crude epoxy alcohols generated were cleaner. The stereochemistry of the product in compound 4 was confirmed by X-ray crystallography.

Our system is unique in that it demonstrates high levels of diastereoselectivity in the epoxidation step for substrates that exhibit either A$^{1,2}$ or A$^{1,3}$ strain in one of their diastereomeric transition states. Other known substrate directed epoxidation methods tend to show high diastereoselectivity for one type of substrate, but not the other, as illustrated in Table 1. We suspect that our titanium allylic alkoxide/zinc peroxide species has a different set of diastereomeric transition states from the more well-known $Ti(O^iPr)_4$/TBHP system, and we are currently exploring this matter. To probe which type of allylic strain ($A^{1,2}$ or $A^{1,3}$) has a greater impact on our system in the epoxidation transition state, a tetrasubstituted divinylzinc reagent was prepared and added to 4-chlorobenzaldehyde (Scheme 4). Epoxidation of the allylic alkoxide intermediate leads to $A^{1,2}$ strain in one diastereomeric transition states, and $A^{1,3}$ strain in the other.

As shown in scheme 4, the in situ asymmetric addition/diastereoselective epoxidation reaction yielded a 3:1 diastereomeric ratio ("dr"). To assign the stereochemistry, we performed the diastereoselective epoxidation of the corresponding isolated allylic alcohol with $Ti(O^iPr)_4$/TBHP, $VO(acac)_2$/TBHP, and the mCPBA systems. Epoxidation systems in which the dominant transition state steric interaction is $A^{1,3}$ strain generate the threo diastereomer as the predominant product (Scheme 4). Based on the known diastereoselectivity patterns of these epoxidizing agents, the major diastereomer in the one-pot reaction shown in Scheme 4 was assigned as the threo diastereomer. We concluded, therefore, that the predominant steric interaction in the transition state for our one-pot $Ti(O^iPr)_4/O_2/ZnEt_2$ epoxidation system is $A^{1,3}$ strain.

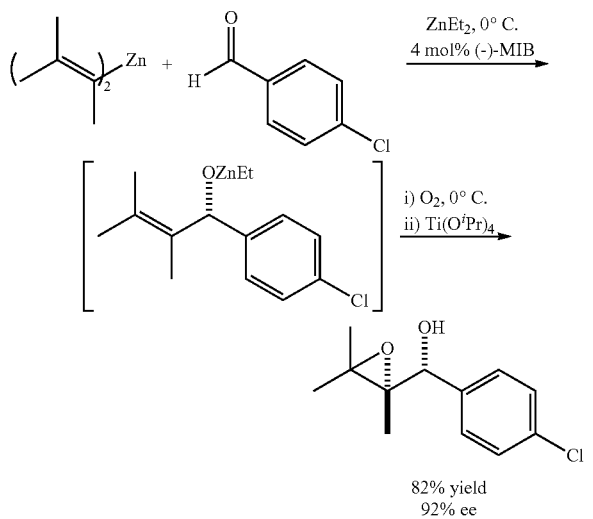

Scheme 4
Determination of the predominant steric interaction in the epoxidation transition state for our one-pot process 82% yield
92% ee Diastereomeric Ratios (erythro:threo)[a]

| One-Pot Method | $Ti(O^iPr)_4$ TBHP | $VO(acac)_2$ TBHP | mCBPA |
|---|---|---|---|
| 1:3 | 1:5[b] | 2:1[b] | 1:10[b] |

[a]dr determined by NMR. [b]epoxidation performed on isolated allylic alcohol. [c]Determined by $^1H$ NMR analysis.

A related selectivity question is the relative rates of epoxidation of cis- versus trans-allylic olefins in our system. In order to explore this, the addition of diethylzinc, followed by in situ epoxidation of an equal mixture of cis- and trans-cinnamaldehyde was performed with 10 mol % $Ti(O^iPr)_4$ and half an equivalent of oxidant (Scheme 5). When the reaction was run under these conditions, only the threo-cis-1-(3-phenyl-oxiranyl)-propan-1-ol was formed, while the trans-1-phenyl-pent-1-en-3-ol was not oxidized. This selective epoxidation demonstrates the ability of our epoxidation system to differentiate between olefins with the same electronics but different geometries.

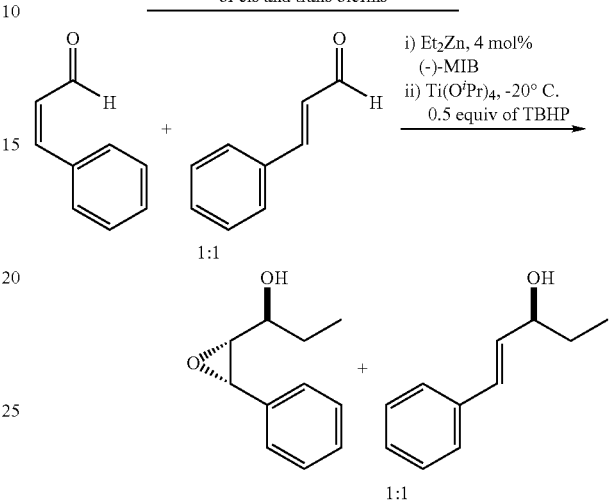

Scheme 5
Comparison of the rates of expoxidation of cis and trans olefins

In expanding the utility of the inventive subject matter, we developed a one-pot process for the synthesis of allylic epoxy alcohols. The first step in our synthesis process of densely functionalized compounds is the generation of a bis(allylic alkoxide) intermediate. We have utilized two methods to generate these intermediates, the first of which is the in situ generation of the vinylzinc species using the hydroboration/transmetalation process of Oppolzer. When a trans-disubstituted vinylzinc reagent, generated in situ from a terminal alkyne, is added to an enal with substitution at the $R^2$ or $R^3$ position, it generates a bis(allylic alkoxide) intermediate with two differently substituted olefins (Scheme 2, Route C). Based on the results depicted in Scheme 5, we expected the trans-disubstituted double bond to be oxidized at a significantly slower rate than the trisubstituted double bond. We found that our epoxidation system is highly chemoselective, leading to epoxidation at the more electron-rich double bond. The allylic epoxy alcohols were produced, therefore, in high yield, and with high enantio- and diastereoselectivities, as shown in Table 2.

TABLE 2

Results for allylic epoxy alcohol synthesis using in situ generated vinylzinc reagents

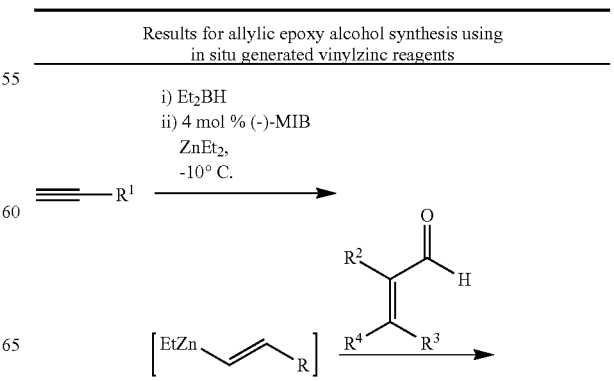

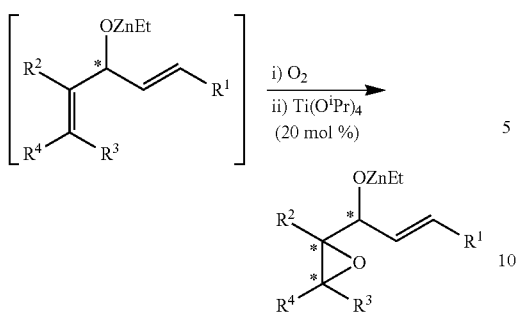

| en-try | allylic epoxy alcohol | % ee (% y) | (ery-thro: threo)[c] [dr] |
|---|---|---|---|
| 1 | (cyclohexane epoxide with OH and chain ending in Cl) | 99[a] (78) | [20:1] |
| 2 | (dimethyl epoxide with OH and t-Bu alkene) | 98[a] (76) | [1:20] |
| 3 | (cyclohexane epoxide with OH and t-Bu alkene) | 97[a] (87) | [20:1] |
| 4 | (cyclohexane epoxide with OH and pentyl alkene) | 99[a] (78) | [20:1] |
| 5 | (cyclohexane epoxide with OH and chain ending in OTr) | 92[b] (60) | [20:1] |
| 6 | (Ph, Me epoxide with OH and pentyl alkene) | 90[b] (80) | [20:1] |

[a]Determined by chiral GC anaylsis.
[b]Determined by chiral HPLC anaylsis.
[c]Determrined by $^1$H NMR analysis.

The second route involves addition of an isolated, purified divinylzinc reagent to an enal, as in Scheme 2, Route D. This leads to an intermediate with two differently substituted olefins, either of which can be diastereoselectively epoxidized, as they both have substituents on the olefin that lead to $A^{1,2}$ or $A^{1,3}$ strain in one of the diastereomeric transition states. In these reactions, it was found that cyclic olefins were chemoselectively epoxidized over di- or trisubstituted double bonds (see Table 3, entries 1, 2 and 4). In Table 3, compound 7, the cis double bond was not epoxidized due to deactivation of the double bond by the electron withdrawing silyl ether. These synthetically challenging allylic epoxy alcohols were synthesized in high yields and with high enantio- and diastereoselectivities (see Table 3, entries 1-4, 7). In the case of vinyl additions to ynals, the epoxy alcohol products were generated with slightly lower enantioselectivites (87% and 86%) and with about 5:1 or 4:1 dr's. This is most likely due to the small size of the alkyne, which does not impart significant $A^{1,2}$ or $A^{1,3}$ strain in a disfavored transition state. Overall, this synthetic route to allylic epoxy alcohols is extremely efficient and selective.

TABLE 3

Results of allylic epoxy alcohol synthesis using isolated, purified divinyl zinc reagents

| entry | allylic epoxy alcohol | % ee (% y) | (erythro:threo)[c] [dr] |
|---|---|---|---|
| 1 | (cyclohexane epoxide with OH and isobutenyl) | 96[a] (61) | [20:1] |
| 2 | (cyclohexane epoxide with OH and isopropenyl) | 95[a] (90) | [20:1] |
| 3 | (dimethyl epoxide with OH and isopropenyl) | 91[a] (91) | [1:20] |
| 4 | (cyclopentane epoxide with OH and isobutenyl) | 96[a] (76) | [20:1] |

TABLE 3-continued

Results of allylic epoxy alcohol synthesis using isolated, purified divinyl zinc reagents

| entry | allylic epoxy alcohol | % ee (% y) | (erythro:threo)[c] [dr] |
|---|---|---|---|
| 5 | (structure) | 87[a] (92) | [1:5] |
| 6 | (structure) | 86[a] (90) | [4:1] |
| 7 | (structure) | 95[b] (80) | [20:1] |

[a]Determined by chiral GC anaylsis.
[b]Detemrined by chiral HPLC anaylsis.
[c]Determined by $^1$H NMR analysis.

Thus, as shown in Table 1, we have developed a convenient one-pot method for the synthesis of epoxy alcohols and allylic epoxy alcohols. The versatility of this method has been demonstrated by a comparison of different catalyst systems. We expect these epoxy alcohols to find widespread utility in asymmetric synthesis of natural and non-natural products.

All methods shown involve initial asymmetric C—C bond formation followed by in situ diastereoselective epoxidation. The oxidation can be achieved using either TBHP or dioxygen and an alkylzinc reagent to generate the active oxidant. Both processes lead to the synthesis of epoxy alcohols in high yields and with high enantio- and diastereoselectivities. We believe that the inventive process employing TBHP will facilitate implementation of this chemistry on large scale.

Our method for the synthesis of epoxy alcohols offers several advantages over existing methods. First, it circumvents the need to prepare and isolate the allylic or bis(allylic) alcohol intermediates, which can be susceptible to decomposition via highly delocalized carbocations. Second, different stoichiometric oxidants may be utilized. Third, the enantio- and diastereoselectivities are high for a wide range of substrates. Lastly, although here we have exemplified three, the initial C—C bond-forming step can be catalyzed by literally hundreds of catalysts.

Alternate catalysts. To date, we have used only titanium tetraisopropoxide, with a limited range of tartrate ligands and BINOL, and VO(acac)$_2$. We expect that diols, tridentate salen ligands, substituted acetylacetonate derivatives, and metallocenes will be acceptable catalysts. These classes of ligands and complexes have been shown to promote epoxidation reaction of alkenols with a variety of metals. We have found that using achiral ligands, including achiral ligands that can adopt chiral conformations, affect substrate directed epoxidation reactions. The C1 stereocenter can induce asymmetry into the achiral ligand, resulting in higher diastereoselectivity, as we have observed in related systems. We have previously prepared a large number of methylene bis(phenols) for an unrelated project and demonstrated that these ligands can adopt chiral binding modes. Simple 1,3-propane diols and 1,3-diketones (precursors to acac ligands) are easily prepared with a variety of substituents. Diols may be used with group (IV) metals, while M(acac) derivatives are known to be excellent epoxidation catalysts with group(V) metals. Metallocenes are also known to promote directed epoxidation reactions. We expect that a group(IV) complexes, including a series of unsymmetrical CpCp'MCl$_2$ derivatives will have an effect on the substitution pattern of the Cp' ligand and on epoxidation diastereoselectivity.

Use of non-racemic chiral ligands in the diastereoselective epoxidation reaction has the benefit of potential kinetic resolutions (KR) of the allylic alkoxide intermediate. Thus, if the addition goes with only moderate enantioselectivity, and the matched and mismatched catalyst/substrate combinations have significantly different rates of epoxidation, the enantiomeric excess of the product epoxy alcohol can be increased over that of the addition product (by KR). We expect that tridentate salen ligands with group IV-VI metals will be useful catalysts. The electron donating salen ligand will stabilize the catalysts with respect to reduction under the reaction conditions. Such reduction was observed with VO(acac)$_2$. TADDOL ligands have been prepared for use in asymmetric catalysis, and are expected to be useful in the diastereoselective epoxidation step with group(IV) metals. Tartrate ligands with bulky alkyl groups, such as cyclododecyl, benzhydrol and CH$_2$(anthracyl) are expected to impact epoxidation because of steric bulk. Given the large number of metals that promote epoxidation reactions, and the variety of their ancillary ligands, it is expected that many catalysts that give high diastereoselectivities in the epoxidation of (E)-disubstituted allylic alcohols can be identified.

Processes of the Inventive Subject Matter

The inventive subject matter relates to a highly enantio- and diastereoselective process for making an epoxy alcohol from an aldehyde, comprising the steps of:

(a) adding (i) an organozinc compound or (ii) a divinylzinc compound and an diorganozinc compound to said aldehyde in the presence of a first catalyst to form an allylic alkoxide compound; and (b) epoxidizing said allylic alkoxide compound in the presence of an oxidant and a second catalyst.

In one aspect of the inventive subject matter, said aldehyde is selected from the group consisting of α,β-unsaturated, aliphatic, and aromatic aldehydes.

In another aspect of the inventive subject matter, said organozinc compound is a compound of formula $Zn(R^1)_2$:

wherein each said $R^1$ is independently selected from the group consisting of:

straight or branched chain $C_1$-$C_9$ alkyl, straight or branched chain $C_1$-$C_9$ alkyl substituted with one or more halo, trifluoromethyl, nitro, $C_1$-$C_6$ straight or branched chain alkyl, $C_2$-$C_6$ straight or branched chain alkenyl, hydroxy, $C_1$-$C_4$ alkoxy, $C_2$-$C_4$ alkenyloxy, phenoxy, benzyloxy, amino, or Ar, O— ($C_1$-$C_9$ straight or branched chain alkyl), straight or branched chain $C_2$-$C_9$ alkenyl or alkynyl, and straight or branched chain $C_2$-$C_9$ alkenyl or alkynyl substituted with one or more halo, trifluoromethyl, nitro, $C_1$-$C_6$ straight or branched chain alkyl, $C_2$-$C_6$ straight or branched chain alkenyl, hydroxy, $C_1$-$C_4$ alkoxy, $C_2$-$C_4$ alkenyloxy, phenoxy, benzyloxy, amino, or Ar, O— ($C_2$-$C_9$ straight or branched chain alkenyl), 1,2-methylenedioxy, alkenoxy, alkoxy, alkylamino, alkylaryloxy, alkylthio, amido, amino, aminoalkyl, arylalkyloxy, aryloxy, azo, benzyl, benzyloxy, $C_1$-$C_9$ alkoxy, $C_2$-$C_9$ alkenyloxy, $C_3$-$C_8$ cycloalkyl, $C_5$-$C_7$ cycloalkenyl, carbonyl, carboxy, carboxylic and heterocyclic moieties cyano, diazo, ester, formanilido, halo, haloalkyl, hydrogen, hydroxy, hydroxymethyl, imino, isocyano, isonitrilo, nitrilo, nitro, nitroso, O-benzyl, O-phenyl, phenoxy, phenyl, sulfhydryl, sulfonyl, sulfonylsulfoxy, thio, thioalkyl, thiocarbonyl, thiocyano, thioester, thioformamido, trifluoromethoxy, trifluoromethyl, and Ar; and Ar is an alicyclic or aromatic, mono-, bi- or tricyclic, carbo- or heterocyclic ring, wherein the ring is either unsubstituted or substituted with one or more substituent(s); wherein the individual ring size is 5-8 members; wherein the heterocyclic ring contains 1-6 heteroatom(s) independently selected from the group consisting of O, N, and S; wherein an aromatic or tertiary alkyl amine is optionally oxidized to a corresponding N-oxide.

In another aspect of the inventive subject matter, said divinylzinc compound is a compound of formula I:

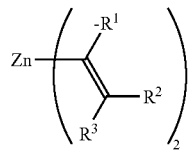

wherein $R^1$, $R^2$, and $R^3$ are independently selected from the group consisting of:

hydrogen, straight or branched chain $C_1$-$C_9$ alkyl, straight or branched chain $C_1$-$C_9$ alkyl substituted with one or more halo, trifluoromethyl, nitro, $C_1$-$C_6$ straight or branched chain alkyl, $C_2$-$C_6$ straight or branched chain alkenyl, hydroxy, $C_1$-$C_4$ alkoxy, $C_2$-$C_4$ alkenyloxy, phenoxy, benzyloxy, amino, or Ar, O— ($C_1$-$C_9$ straight or branched chain alkyl), straight or branched chain $C_2$-$C_9$ alkenyl or alkynyl, and straight or branched chain $C_2$-$C_9$ alkenyl or alkynyl substituted with one or more halo, trifluoromethyl, nitro, $C_1$-$C_6$ straight or branched chain alkyl, $C_2$-$C_6$ straight or branched chain alkenyl, hydroxy, $C_1$-$C_4$ alkoxy, $C_2$-$C_4$ alkenyloxy, phenoxy, benzyloxy, amino, or Ar, O— ($C_2$-$C_9$ straight or branched chain alkenyl), 1,2-methylenedioxy, alkenoxy, alkoxy, alkylamino, alkylaryloxy, alkylthio, amido, amino, aminoalkyl, arylalkyloxy, aryloxy, azo, benzyl, benzyloxy, $C_1$-$C_9$ alkoxy, $C_2$-$C_9$ alkenyloxy, $C_3$-$C_8$ cycloalkyl, $C_5$-$C_7$ cycloalkenyl, carbonyl, carboxy, carboxylic and heterocyclic moieties cyano, diazo, ester, formanilido, halo, haloalkyl, hydrogen, hydroxy, hydroxymethyl, imino, isocyano, isonitrilo, nitrilo, nitro, nitroso, O-benzyl, O-phenyl, phenoxy, phenyl, sulfhydryl, sulfonyl, sulfonylsulfoxy, thio, thioalkyl, thiocarbonyl, thiocyano, thioester, thioformamido, trifluoromethoxy, trifluoromethyl, and Ar; and Ar is an alicyclic or aromatic, mono-, bi- or tricyclic, carbo- or heterocyclic ring, wherein the ring is either unsubstituted or substituted with one or more substituent(s); wherein the individual ring size is 5-8 members; wherein the heterocyclic ring contains 1-6 heteroatom(s) independently selected from the group consisting of O, N, and S; wherein an aromatic or tertiary alkyl amine is optionally oxidized to a corresponding N-oxide.

In another aspect of the inventive subject matter, said first catalyst is selected from the group consisting of amino alcohol-based catalysts and bis(sulfonamide) catalysts. However, Applicants observe that the inventive subject matter is intended in its broadest sense to encompass other catalysts for promoting the addition of an alkyl, vinyl, or acetylide to an aldehyde. Such other catalysts are known to one of ordinary skill in the art.

In a preferred embodiment, said amino alcohol-based catalyst is Nugent's morpholino isoborneol (MIB) ligand.

In another preferred embodiment, said bis(sulfonamide) catalyst is selected from the group consisting of

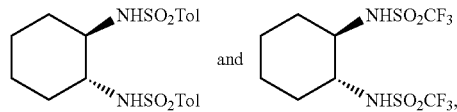

wherein said bis(sulfonamide) catalyst is used with $Ti(O^iPr)_4$ or $Ti(O^tBu)_4$.

In a further aspect of the inventive subject matter, said oxidant is selected from the group consisting of dioxygen, tert-butyl hydroperoxide, and hydroperoxides of formula ROOH. However, Applicants observe that the inventive subject matter is intended in its broadest sense to encompass other oxidants for epoxidizing an alkoxide. Such other oxidants are known to one of ordinary skill in the art.

In an alternate aspect of the inventive subject matter, said second catalyst is selected from the group consisting of a transition metal catalysts, and organic peracids.

In a preferred embodiment, said transition metal catalyst is selected from the group consisting of $VO(acac)_2$, $Ti(O^iPr)_4$, and $Ti(O^tBu)_4$.

In another preferred embodiment, said organic peracid is meta-chloroperoxybenzoic acid.

Further, in another aspect of the inventive subject matter, said process for making an acyclic epoxy alcohol comprises the steps of:

(a) adding a first organozinc compound to an aldehyde in the presence of a first catalyst selected from the group consisting of Nugent's morpholino isoborneol ligand,

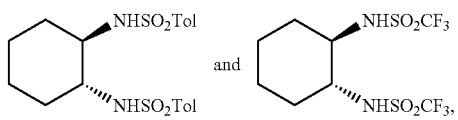

to form an allylic alkoxide compound, wherein said first catalyst additionally comprises Ti(O$^i$Pr)$_4$ or Ti(O$^t$Bu)$_4$ when a bis(sulfonamide) is used; and (b) epoxidizing said allylic alkoxide compound in the presence of diethyl zinc, an oxidant selected from the group consisting of dioxygen and tert-butyl hydroperoxide, and a second catalyst selected from the group consisting of VO(acac)$_2$, Ti(O$^i$Pr)$_4$, Ti(O$^t$Bu)$_4$, and meta-chloroperoxybenzoic acid.

In a preferred embodiment, said first organozinc compound is dimethylzinc and said first catalyst is selected from the group consisting of

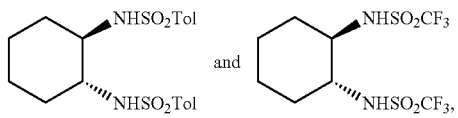

in combination with Ti(O$^i$Pr)$_4$ or Ti(O$^t$Bu)$_4$.

In another aspect of the inventive subject matter, said process for making an acyclic epoxy alcohol comprises the steps of:

(a) adding a divinylzinc compound to a aldehyde in the presence of a first catalyst selected from the group consisting of Nugent's morpholino isoborneol ligand,

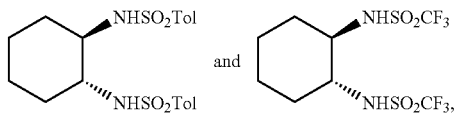

to form an allylic alkoxide compound; and (b) epoxidizing said allylic alkoxide compound in the presence of an oxidant selected from the group consisting of dioxygen and tert-butyl hydroperoxide, and a second catalyst selected from the group consisting of VO(acac)$_2$, Ti(O$^i$Pr)$_4$, Ti(O$^t$Bu)$_4$, and meta-chloroperoxybenzoic acid.

In an alternate aspect of the inventive subject matter, said process for making an acyclic epoxy alcohol comprises the steps of:

(a) adding a trans-disubstituted divinylzinc compound and an organozinc compound to an α,β-unsaturated aldehyde in the presence of a first catalyst selected from the group consisting of

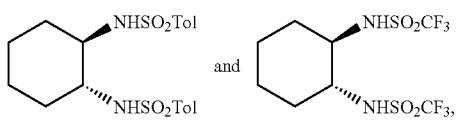

to form a bis(allylic alkoxide) compound; and (b) epoxidizing said bis(allylic alkoxide) compound in the presence of an oxidant selected from the group consisting of dioxygen and tert-butyl hydroperoxide, and a second catalyst selected from the group consisting of VO(acac)$_2$, Ti(O$^i$Pr)$_4$, Ti(O$^t$Bu)$_4$, and meta-chloroperoxybenzoic acid.

In a preferred embodiment, said trans-disubstituted divinylzinc compound is optionally synthesized in situ by a hydroboration/transmetalation reaction of a terminal alkyne with an enal substituted at the R$^2$ or R$^3$ position, to generate said bis(allylic alkoxide) intermediate.

In the preparation of the compounds of the inventive subject matter, one skilled in the art will understand that one may need to protect or block various reactive functionalities on the starting compounds or intermediates while a desired reaction is carried out on other portions of the molecule. After the desired reactions are complete, or at any desired time, normally such protecting groups will be removed by, for example, hydrolytic or hydrogenolytic means. Such protection and deprotection steps are conventional in organic chemistry. One skilled in the art is referred to "Protective Groups in Organic Chemistry," McOmie, ed., Plenum Press, New York, N.Y. (1973); and "Protective Groups in Organic Synthesis, 3$^{rd}$ Edition" Greene, ed., John Wiley & Sons, New York, N.Y. (1999) for the teaching of protective groups which may be useful in the preparation of compounds of the inventive subject matter.

The product and intermediates may optionally be isolated or purified using one or more standard purification techniques, including, for example, one or more of simple solvent evaporation, recrystallization, distillation, sublimation, filtration, chromatography, including thin-layer chromatography, HPLC (e.g. reverse phase HPLC), column chromatography, flash chromatography, radial chromatography, trituration, and the like.

In addition to the disclosure of the inventive subject matter above, another synthetic route from our early work is based on the highly enantioselective alkyl addition to α,β-unsaturated aldehydes promoted by catalyst generated from Nugent's (-)-MIB[8] (1, Scheme 6). The ee's of the allylic alcohols formed on quenching the reaction with aqueous NH$_4$Cl are recorded in Table 4. In the tandem addition/epoxidation procedure, the newly formed allylic alkoxide is exposed to 1 atm of dioxygen at 0° C. (30 min), cooled to −20° C., and titanium tetraisopropoxide (20 mol %) is added. Epoxidation is complete in 18 h at this temperature. We believe the oxidant is formed upon insertion of dioxygen into a Zn—C bond to generate the peroxy species R—Zn—OOR. Subsequent transmetalation to the titanium allylic alkoxide intermediate is followed by directed epoxidation. After workup, the dr's were determined by $^1$H NMR of the crude products and are shown in Table 4, along with the combined yields of both diastereomers after chromatography.

The rate of addition of dimethylzinc to aldehydes with MIB and related amino alcohol-based catalysts is slow at rt. We therefore, employed bis(sulfonamide) ligand 2 in the methyl addition reactions at rt (Scheme 6, Table 4) followed by exposure to dioxygen.

Scheme 1. Tandem Asymmetric Addition/Diastereoselective Epoxidations.

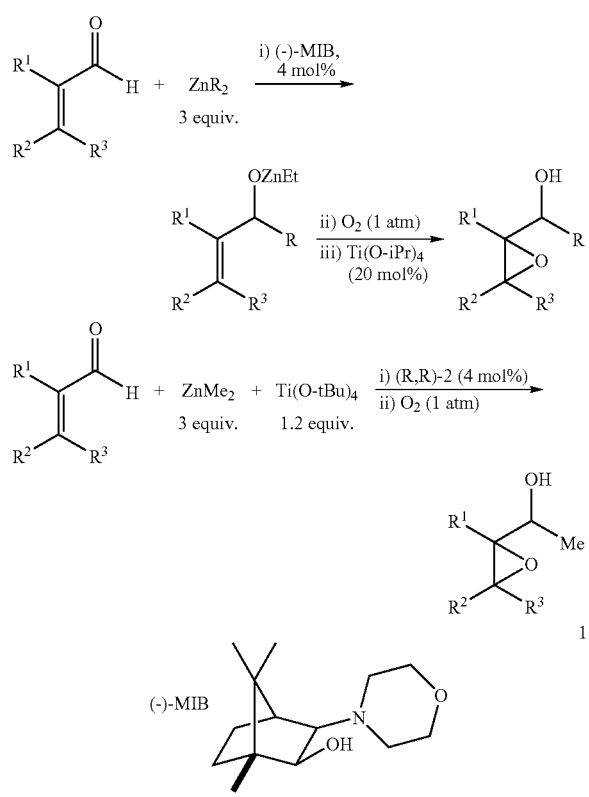

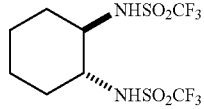

The levels of enantioselectivity in the asymmetric addition of a variety of alkyl groups were very high (85-99%, Table 4). Moderate to excellent dr's were found and, in most cases, were better than those we observed on epoxidation of the isolated allylic alcohols with Ti(O-iPr)$_4$/TBHP, VO(acac)$_2$/TBHP or m-CPBA. Allylic alkoxide intermediates possessing A$^{1,2}$-strain in one of the diastereomeric transition states afford mainly the erythro products (entries 1-4 and 7-9), while those with A$^{1,3}$-strain primarily furnish the threo diastereomers (entries 5, 6, 10-12). The stereochemistry of the product in compound 5 was confirmed by X-ray crystallography.

A second synthetic route to epoxy alcohols from our earlier work entailed the addition of divinylzinc reagents 3 and 4 to aliphatic and aromatic aldehydes, as illustrated in Table 4. The divinylzinc reagents are easily prepared and purified by sublimation. In order to conserve the divinylzinc reagents, 3.1 equiv. diethylzinc was added before the aldehyde. This likely results in formation of ethyl vinyl zinc species, in which the more reactive vinyl group is preferentially transferred. As displayed in Table 4 (entries 1-5), the enantio- and diastereoselectivities with divinylzinc reagent 3 are excellent, and the yields are high. Likewise, reaction of the 2,2'-dimethyl divinylzinc reagent 4 resulted in very high enantio- and diastereoselectivities, except with unbranched aldehydes, where the enantioselectivities were around 80%.

TABLE 4

Synthesis of epoxy alcohols from enals

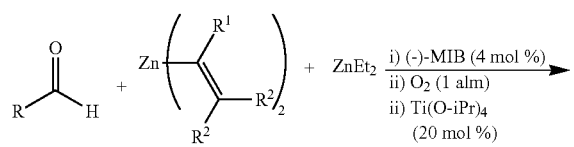

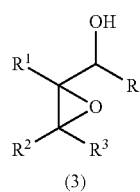

(3)

| | | one-pot method | | Ti(OiPr)$_4$ | VO(acac)$_2$ | |
|---|---|---|---|---|---|---|
| entry | epoxy alcohol[a] | % ee[b] (% y) | [dr] | t-BuOOH | t-BuOOH | mCPBA |
| 1 | 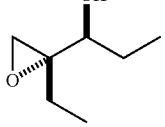 | 93 (60) | [17:1] | 8:1 | 20:1 | 1.1:1 |

Diastereomeric Ratios (erythro:threo)[c]

TABLE 4-continued

Synthesis of epoxy alcohols from enals 1 equiv.
3, R¹ = Me, R² = H
4, R¹ = H, R² = Me 3.1 equiv.

i) (-)-MIB (4 mol %)
ii) O₂ (1 atm)
ii) Ti(O-iPr)₄ (20 mol %)

(3)

| entry | epoxy alcohol[a] | one-pot method | | Ti(OiPr)₄ | VO(acac)₂ | |
| | | % ee[b] (% y) | [dr] | t-BuOOH | t-BuOOH | mCPBA |
| --- | --- | --- | --- | --- | --- | --- |
| 2 | | 96 (65) | [18:1] | 8:1 | 20:1 | 1:1.1 |
| 3 | | 99 (90) | [20:1] | 6:1 | 18:1 | 1.6:1 |
| 4 | | 95 (81) | [5.5:1] | 3.1:1 | 9:1 | 1:1.1 |
| 5 | | 91 (96) | [1:10] | 1:7 | 1:3 | 1:8 |
| 6 | | 95 (96) | [1:20] | 1:6 | 1:2 | 1:20 |
| 7 | | 99 (78) | [20:1] | | | |
| 8 | | 97 (62) | [15:1] | | | |

Diastereomeric Ratios (erythro:threo)[c]

TABLE 4-continued

Synthesis of epoxy alcohols from enals

R-CHO + Zn(CR¹=CR²R²)₂ + ZnEt₂ →
i) (-)-MIB (4 mol %)
ii) O₂ (1 atm)
ii) Ti(O-iPr)₄ (20 mol %)

1 equiv.
3, R¹ = Me, R² = H
4, R¹ = H, R² = Me 3.1 equiv.

Product (3): epoxy alcohol with R¹, R², R³, R substituents and OH group

| | | Diastereomeric Ratios (erythro:threo)[c] | | | |
|---|---|---|---|---|---|
| | | one-pot method | | Ti(OiPr)₄ | VO(acac)₂ |
| entry | epoxy alcohol[a] | % ee[b] (% y) | [dr] | t-BuOOH | t-BuOOH | mCPBA |
| 9 | (cyclohexane epoxide with OH and (CH₂)₅OTBDPS) | 98 (86) | [20:1] | | | |
| 10 | (Ph, OH, epoxide with methyl) | 85 (89) | [1:10] | | | |
| 11 | (dimethyl epoxide with OH) | 96 (60) | [1:18] | | | |
| 12 | (dimethyl epoxide with OH and isohexyl chain) | 96 (81) | [1:20] | | | |

[a]Stereochemistry indicated corresponds to that of the major diastereomer.
[b]Determined by chiral HPLC or GC analysis.
[c]Determined by ¹H NMR analysis.

TABLE 5

Synthesis of epoxy alcohols from divinylzinc reagents

| | | | | Diastereomeric Ratios (erythro:threo)[c] | |
|---|---|---|---|---|---|
| | | one-pot method | | VO(acac)$_2$ | |
| entry | epoxy alcohol[a] | % ee[b] (% y) | [dr] | t-BuOOH | mCPBA |
| 1 | | 92 (87) | [17:1] | 18:1 | 1:1.1 |
| 2 | | 87 (80) | [18:1] | 18:1 | 1.1:1 |
| 3 | | 97 (80) | [18:1] | 17:1 | 1:1.1 |
| 4 | | 90 (85) | [14:1] | | |
| 5 | | 96 (82) | [16:1] | | |
| 6 | | 90 (75) | [19:1] | 1:4 | 1:17 |
| 7 | | 85 (78) | [1:17] | 1:4 | 1:16 |
| 8 | | 96 (84) | [1:18] | 1:3 | 1:17 |
| 9 | | 81 (77) | [1:20] | | |

TABLE 5-continued

Synthesis of epoxy alcohols from divinylzinc reagents

| entry | epoxy alcohol[a] | % ee[b] (% y) | [dr] | one-pot method t-BuOOH | VO(acac)$_2$ mCPBA |
|---|---|---|---|---|---|
| 10 | (structure) | 95 (81) | [1:19] | | |

Diastereomeric Ratios (erythro:threo)[c]

[a]Stereochemistry indicated corresponds to that of the major diastereomer.
[b]Determined by chiral HPLC or GC analysis.
[c]Determined by $^1$H NMR analysis.

Finally, our earliest work relates to the process shown in Scheme 7 below, the results of which are summarized in Table 6 below.

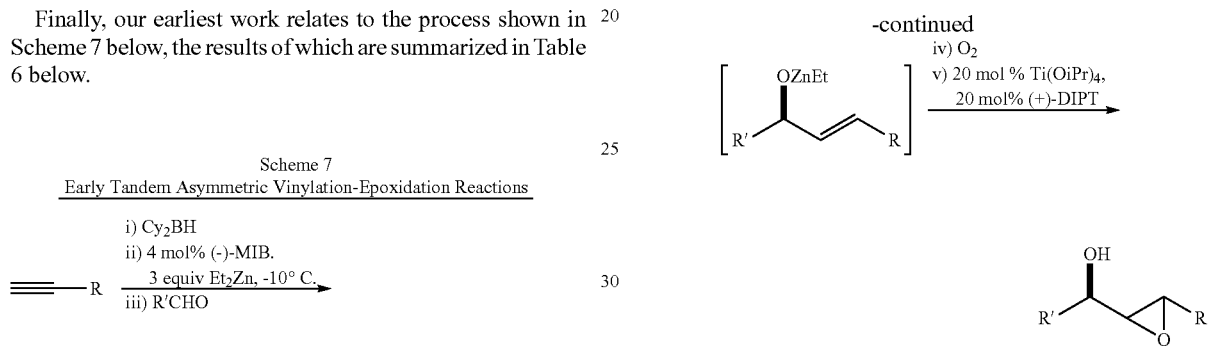

Scheme 7
Early Tandem Asymmetric Vinylation-Epoxidation Reactions

TABLE 6

Enantio- and Diastereoselectivities for One-Pot Asymmetric Synthesis of trans-Disubstituted Epoxy Alcohols

| entry | allylic alcohol | % ee | epoxy alcohol | dr (threo:erythro)[c] | yield[d] |
|---|---|---|---|---|---|
| 1 | 1 | 96[a] | 15 | 4.3:1 | 77 |
| 2 | 2 | 94[a] | 16 | 3.5:1 | 83 |
| 3 | 3 | 93[a] | 17 | 4.1:1 | 78 |

TABLE 6-continued

Enantio- and Diastereoselectivities for One-Pot Asymmetric Synthesis of trans-Disubstituted Epoxy Alcohols

| entry | allylic alcohol | % ee | epoxy alcohol | dr (threo:erythro)[c] | yield[d] |
|---|---|---|---|---|---|
| 4 | 4 | 94[a] | 18 | 3.8:1 | 77 |
| 5 | 5 | 95[a] | 19 | 3.6:1 | 85 |
| 6 | 6 | 95[a] | 20 | 3.5:1 | 76 |
| 7 | 7 | 93[b] | 21 | 2.9:1 | 92 |
| 8 | 8 | 95[a] | 22 | 3.3:1 | 85 |
| 9 | 9 | 95[a] | 23 | 3.3:1 | 83 |
| 10 | 10 | 96[b] | 24 | 3.8:1 | 74 |

TABLE 6-continued

Enantio- and Diastereoselectivities for One-Pot Asymmetric
Synthesis of trans-Disubstituted Epoxy Alcohols

| entry | allylic alcohol | % ee | epoxy alcohol | dr (threo:erythro)[c] | yield[d] |
|---|---|---|---|---|---|
| 11 | 11 | 85[b] | 25 | 4.3:1 | 89 |
| 12 | 12 | 79[b] | 26 | 3.2:1 | 69 |
| 13 | 13 | 77[b] | 27 | 4.5:1 | 68 |
| 14 | 14 | 92[b] | 28 | 3.1:1 | 77 |

[a]Determined by chiral HPLC analysis.
[b]Determined by chiral GC analysis.
[c]Diastereomeric ratio of threo:erythro determined by $^1$H NMR analysis.
[d]Total isolated yield for both diastereomers.

EXAMPLES

The following examples are illustrative of the inventive subject matter and are not intended to be limitations thereon. Unless otherwise indicated, all percentages are based upon 100% by weight of the final composition.

The following examples illustrate the preparation of preferred intermediates and products provided according to the inventive subject matter.

Example 1

General Methods

All reactions were carried out under a nitrogen atmosphere with oven-dried glassware. The progress of all reactions was monitored by thin-layer chromatography to ensure the reactions had reached completion. All manipulations involving dialkylzinc reagents were carried out using an inert atmosphere in a drybox or by using standard Schlenk or vacuum line techniques. Dichloromethane and hexanes were dried through alumina columns. All aldehydes were distilled prior to use and stored under $N_2$. Unless otherwise specified, all chemicals were commercially available and obtained from Acros, Aldrich, or GFS Chemicals, and all solvents were commercially available and purchased from Fischer Scientific. The $^1$H NMR and $^{13}$C{$^1$H} NMR spectra were obtained on a Bruker AM-500 Fourier transform NMR spectrometer at 500 and 125 MHz, respectively. Chemical shifts are reported in units of parts per million downfield from tetramethylsilane, and all coupling constants are reported in Hertz. The infrared spectra were obtained using a Perkin-Elmer 1600 series spectrometer. Thin-layer chromatography was performed on Whatman precoated silica gel 60 F-254 plates and visualized by ultra-violet light or by staining with cerric ammonium molybdate stain. Silica gel (230-400 mesh, Silicycle) was used for air-flashed chromatography. Analysis of enantiomeric excess was performed using a Hewlett-Packard 1100 Series HPLC and a Chiralcel OD-H column or by chiral capillary gas chromatography on a Hewlett-Packard 6890 GC with a Beta-DEX column. Absolute configuration was determined by comparison of optical rotation to literature data for known compounds.

Compounds from Table 2

Example 2

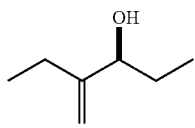

43

General Procedure A

Preparation of (S)-2-Ethyl-pent-1-en-3-ol (Table 2, Compound 1)

A 10 mL Schlenk flask was charged with (−)-MIB (1.9 mg, 0.008 mmol) and 1 mL hexanes and cooled, to 0° C. A hexanes solution of $Et_2Zn$ (0.2 mL, 2.0 M) was added, followed by addition of 2-ethylpropenal (16.8 mg, 0.20 mmol) dropwise. The reaction was stirred at 0° C. for 8 h and quenched with a saturated solution of aq $NH_4Cl$. The organic and aqueous layers were separated, and the aqueous layer was, extracted with hexanes (3×10 mL). The combined organic layers were then washed with brine and $H_2O$ and dried over $MgSO_4$. The filtrate was concentrated in vacuo and the residue was chromatographed on silica (20% ethyl acetate in hexanes) to afford the title compound as a colorless oil in 80% yield (45.7 mg, 0.20 mmol). $^1H$ NMR and $^{13}C\{^1H\}$ NMR spectra for this compound were identical to the previously reported literature data.

Example 3

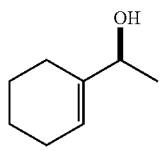

General Procedure B

Preparation of (S)-1-Cyclohex-1-enyl-ethanol (Table 2, Compound 9)

A 10 mL Schlenk flask was charged with bis(sulfonamide) ligand L*₂ (3.8 mg, 0.01 mmol), $Ti(O^tBu)_4$ (193 □L, 0.50 mmol), and 0.5 mL hexanes and stirred for 30 min at room temp. A hexanes solution of $Me_2Zn$ (0.32 mL, 0.63 mmol) was then added, and after stirring for 10 min, cyclohexenecarboxaldehyde (28 □L, 0.25 mmol) was added. The reaction was stirred at room temp for 19 h and quenched with a saturated solution of aq $NH_4Cl$. The organic and aqueous layers were separated, and the aqueous layer was extracted with hexanes (3×10 mL). The combined organic layers were then washed with brine and $H_2O$ and dried over $MgSO_4$. The filtrate was concentrated in vacuo and the residue was chromatographed on silica (10% ethyl acetate in hexanes) to afford the title compound as a colorless oil in 94% yield (30 mg, 0.23 mmol). $^1H$ NMR and $^{13}C\{^1H\}$ NMR spectra for this compound were identical to the previously reported literature data.

Example 4

44

General Procedure C

Epoxidation with $Ti(O^iPr)_4$ and Dioxygen

Preparation of erythro-1-(2-Ethyl-oxiranyl)-propan-1-ol. (Table 2, Compound 1)

A 10 mL Schlenk flask was charged, with (−)-MIB (5.0 mg, 0.020 mmol) and 1 mL hexanes and cooled to 0° C. A hexanes solution of $Et_2Zn$ (0.5 mL, 2.0 M) was added, followed by addition of 2-ethylpropenal (52 µL, 0.5 mmol) dropwise. The reaction was stirred at 0° C. for 8 h until alkyl addition was complete by TLC. The reaction flask was then capped with a balloon of oxygen. After stirring at 0° C. for 1 h, the reaction flask was cooled to −20° C., and a hexanes solution of $Ti(O^iPr)_4$ (0.05 mL, 1.0 M) was added. The reaction continued to stir at −20° C. under an $O_2$ atmosphere for 18 h. It was then quenched with 15% tartaric acid solution, allowed to stir for 45 min, and poured into a separatory funnel with a solution of $Na_2S_2O_4$. The organic and aqueous layers were separated, and the aqueous layer was extracted with hexanes (3×10 mL). The combined organic layers were then washed with brine and $H_2O$ and dried over $MgSO_4$. The filtrate was concentrated in vacuo, and the residue was chromatographed on silica (20% ethyl acetate in hexanes) to afford the title compound as a colorless oil in 60% yield (39 mg, 0.30 mmol).

Example 5

General Procedure D

Epoxidation with $Ti(O^iPr)_4$ and TBHP

A 10 mL Schlenk flask was charged with (−)-MIB (4.8 mg, 0.020 mmol) and 2 mL of hexanes and cooled to 0° C. A hexanes solution of $Et_2Zn$ (0.75 mL, 2.0 M) was added, followed by addition of 2-ethylpropenal (49 µL, 0.5 mmol) dropwise. The reaction was stirred at 0° C. for 20 h until alkyl addition was complete by TLC, then the reaction flask was cooled to −20° C. A solution of $Ti(O^iPr)_4$ in dichloromethane (100 µL, 1.0 M) was added, followed by dropwise, careful addition of a decane solution of TBHP (0.45 mL, 5.5 M). The reaction continued to stir at −20° C. for 8 h. It was then quenched with 4 mL saturated aq $NH_4Cl$, allowed to stir for 30 min at room temp, and poured into a separatory funnel with a solution of $Na_2S_2O_4$. The organic and aqueous layers were separated, and the aqueous layer was extracted with diethyl ether (3×5 mL). The combined organic layers were then washed with 5 mL brine and 5 mL $H_2O$ and dried over $MgSO_4$. The filtrate was concentrated in vacuo, and the residue was chromatographed on silica (10% ethyl acetate in hexanes) to afford the title compound as a colorless oil in 65% yield (42 mg, 0.32 mmol). $^1H$ NMR and $^{13}C\{^1H\}$ NMR spectra for this compound were identical to the previously reported literature data.

Example 6

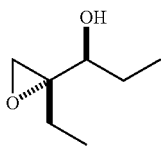

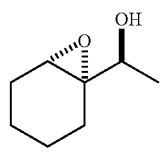

General Procedure E

Epoxidation with Ti(O$^t$Bu)$_4$ and Dioxygen

Preparation of erythro-1-(7-Oxa-bicyclo[4.1.0]hept-1-yl)-ethanol (Table 2, Compound 9)

A 10 mL Schlenk flask was charged with bis(sulfonamide) ligand L*$_2$ (3.8 mg, 0.01 mmol), Ti(O$^t$Bu)$_4$ (97 μL, 0.25 mmol), and 0.5 mL hexanes and stirred for 30 min at room temp. A hexanes solution of Me$_2$Zn (0.25 mL, 0.50 mmol) was then added, and after stirring for 10 min, cyclohexenecarboxaldehyde (14 μL, 0.13 mmol) was added. The reaction was stirred at room temp for 20 h, until alkyl addition was complete by TLC, then cooled to 0° C. 1 equiv Me$_2$Zn (63 μL, 0.13 mmol) was added; the reaction flask was capped with a balloon of oxygen, warmed to room temperature and allowed to stir under an O$_2$ atmosphere for 19 h. It was then quenched with 15% tartaric acid solution, allowed to stir for 45 min, poured into a separatory funnel with a solution of Na$_2$S$_2$O$_4$. The organic and aqueous layers were separated, and the aqueous layer was extracted with hexanes (3×10 mL). The combined organic layers were then washed with brine and H$_2$O and dried over MgSO$_4$. The filtrate was concentrated in vacuo, and the residue was chromatographed on silica (10% ethyl acetate in hexanes) to afford the title compound as a colorless oil in 78% yield (14 mg, 0.099 mmol).

Example 7

General Procedure F

Epoxidation with Ti(O$^t$Bu)$_4$ and TBHP

A 10 mL Schlenk flask was charged with bis(sulfonamide) ligand L*$_2$ (30 mg, 0.08 mmol), Ti(O$^t$Bu)$_4$ (0.77 mL, 2.0 mmol), and 1.0 mL of hexanes and stirred for 30 min at room temp. A hexanes solution of Me$_2$Zn (2.0 mL, 4.0 mmol) was then added, and after stirring for 10 min, cyclohexenecarboxaldehyde (114 μL, 1.0 mmol) was added. The reaction was stirred at room temp for 20 h, until alkyl addition was complete by TLC, then cooled to 0° C. A solution of TBHP in decane (0.91 mL, 5.5 M) was carefully added dropwise, and the stirring continued at 0° C. for 20 h. It was then quenched with 4 mL saturated aq NH$_4$Cl, allowed to stir for 30 min at room temp, and poured into a separatory funnel with a solution of Na$_2$S$_2$O$_4$. The organic and aqueous layers were separated, and the aqueous layer was extracted with diethyl ether (3×5 mL). The combined organic layers were then washed with 5 mL brine and 5 mL H$_2$O and dried over MgSO$_4$. The filtrate was concentrated in vacuo, and the residue was chromatographed on silica (10% ethyl acetate in hexanes) to afford the title compound as a colorless oil in 89% yield (126 mg, 0.89 mmol). $^1$H NMR and $^{13}$C{$^1$H} NMR spectra for this compound were identical to the previously reported literature data.

Example 8

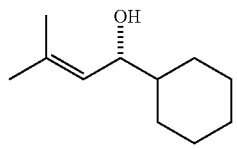

General Procedure G

Preparation of (S)-1-Methyl-4-cyclohexyl-buten-4-ol (Table 2, Compound 13)

A 10 mL Schlenk flask was charged with 3.5 mg (0.015 mmol) (−)-MIB and a stir bar. Under a nitrogen atmosphere in a glovebox, the di(2-methyl-propene)zinc reagent (89.5 mg, 0.51 mmol) was weighed and added to the Schlenk flask. Toluene (1.5 mL) was added, followed by 3.1 equiv Et$_2$Zn (115 μL, 1.13 mmol). After cooling to 0° C., cyclohexanecarboxaldehyde (40.8 mg, 0.36 mmol) was added dropwise. After the reaction was complete (2 h), it was quenched with saturated aq NH$_4$Cl. The organic and aqueous layers were separated and the aqueous layer was extracted with diethyl ether (3×25 mL). The combined organic layers were washed with brine, dried over MgSO$_4$ and concentrated. The crude product was purified by column chromatography on silica (70:20:10, hexanes:CH$_2$Cl$_2$:EtOAc) to afford the title compound as a colorless oil in 75% yield (45.8 mg, 0.27 mmol). $^1$H NMR and $^{13}$C{$^1$H} NMR spectra for this compound were identical to the previously reported literature data.

Example 9

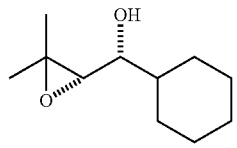

General Procedure H

Preparation of threo-(S)-1-(1-Methyl-2-oxiranyl-4-cyclohexyl)-butan-4-ol (Table 2, Compound 13)

A 10 mL Schlenk flask was charged with 3.5 mg (0.015 mmol) (−)-MIB and a stir bar. Under a nitrogen atmosphere in a glovebox, the di(2-methyl-propene)zinc reagent (89.5 mg, 0.51 mmol) was weighed and added to the Schlenk flask. Toluene (1.5 mL) was added, followed by 3.1 equiv Et$_2$Zn (115 μL, 1.13 mmol). After cooling to 0° C., cyclohexanecarboxaldehyde (40.8 mg, 0.36 mmol) was added dropwise. The reaction was stirred for 2 h, then the solution was cooled to −20° C., and saturated with 1 atm of O$_2$ for 30 min. A solution of Ti(O$^i$Pr)$_4$ in toluene (0.095 mmol, 2.0 M) was added under an N$_2$ purge dropwise, followed by resaturation of the solution with the O₂ balloon. After stirring the reaction at −20° C. for 12 h, the flask was warmed to 0° C. The epoxidation reaction was stirred for 24 h, then quenched with saturated aq NH₄Cl and 8 mL aq Na₂CO₃. The pale yellow biphasic solution and salts were filtered through celite, washed with diethyl ether (2×25 mL), and the aqueous layer was extracted with diethyl ether (3×30 mL). The combined organic layers were washed with brine, dried over MgSO₄ and concentrated. The crude product was purified by column chromatography on silica (60:30:10, hexanes:CH₂Cl₂:EtOAc) to afford the title compound as a colorless oil in 79% yield (68.9 mg, 0.37 mmol). $^1$H NMR and $^{13}$C{$^1$H} NMR spectra for this compound were identical to the previously reported literature data.

Compounds from Table 2

Example 10

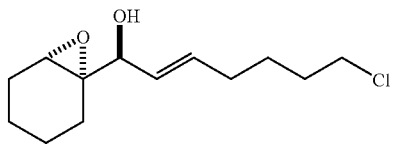

General Procedure I

Preparation of erythro-(S)-7-Chloro-1-(7-oxa-bicyclo[4.1.0]hept-1-yl)-hept-2-en-1-ol (Table 2, Compound 1)

6-Chloro-hex-1-yne [140 mg (1.2 mmol)] and diethylborane [1.2 mL (1.2 mmol, 1.0 M in hexanes)] were stirred at room temp for 1 h. The solvent was removed in vacuo, and 1 mL of hexanes was added. In a separate flask, 2.2 mL (2.2 mmol, 1.0 M in hexanes) diethylzinc, 9.6 mg (0.04 mmol) (−)-MIB, and a 114 μL (1.0 mmol) cyclohexenecarboxaldehyde were combined and stirred at −78° C. The hydroboration product was cannulated into the reaction flask, and after 30 min, the temperature was increased to −10° C. The reaction was monitored by TLC until the addition was complete (6 h). The temperature was then decreased to −20° C., the reaction headspace was purged, and the reaction was exposed to dioxygen. After 30 min, 200 μL (0.20 mmol, 1.0 M in hexanes) Ti(O$^i$Pr)₄ was added. The reaction proceeded under 1 atm of O₂. After the reaction was complete (24 h), it was quenched with saturated aq NH₄Cl and extracted with hexanes (3×10 mL). The crude product was dried over MgSO₄, concentrated in vacuo, and purified by column chromatography on silica (10% ethyl acetate in hexanes) to afford the title compound as a colorless oil in 78% yield (191 mg, 0.78 mmol). [α]$_D^{20}$=−2.16 (c=0.74, CHCl₃); $^1$H NMR (CDCl₃, 500 MHz) δ 1.25 (m, 2H), 1.43 (m, 2H), 1.57 (s, 4H), 1.76 (m, 2H), 1.96 (m, 2H), 2.10 (q, 2H, J=7.0 Hz), 2.32 (br s, 1H), 3.23 (s, 1H), 3.52 (t, 2H, J=5.0 Hz), 3.98 (d, 1H, J=10.0 Hz), 5.40 (dd, 1H, J=10.0, 15.0 Hz), and 5.77 (dt, 1H, J=5.0, 15.0 Hz) ppm; $^{13}$C{$^1$H} NMR (CDCl₃, 125 MHz) δ 20.1, 20.8, 25.0, 25.5, 26.8, 32.1, 32.6, 45.5, 55.9, 65.2, 74.0, 136.0, and 140.9 ppm; IR (neat) 3387, 2920, 2860, 1615, 1430, 1259, and 1060 cm$^{-1}$; HRMS-CI m/z 227.1204 [(M−OH)⁺; calcd for C₁₃H₂₀OCl: 227.1203].

Example 11

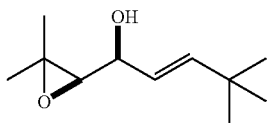

Preparation of threo-(S)-1-(3,3-Dimethyl-oxiranyl)-4,4-dimethyl-pent-2-en-1-ol (Table 2, Compound 2)

The product was prepared by General Procedure I using 98.5 mg (1.2 mmol) t-butyl acetylene, 1.2 mL (1.2 mmol, 1.0 M in hexanes) diethylborane, 2.2 mL (2.2 mmol, 1.0 M in hexanes) diethylzinc, 9.6 mg (0.04 mmol) (−)-MIB, 200 μL (0.20 mmol, 1.0 M in hexanes) Ti(O$^i$Pr)₄, 84 mg (1.0 mmol) 3-methyl-but-2-enal. The crude product was purified by column chromatography on silica (10% ethyl acetate in hexanes) to afford the title compound as a colorless oil in 76% yield (140 mg, 0.76 mmol). [α]$_D^{20}$=−4.04 (c=0.94, CHCl₃); $^1$H NMR (CDCl₃, 500 MHz) δ 1.02 (s, 9H), 1.24 (s, 3H), 1.25 (s, 3H), 2.04 (br s, 1H), 2.75 (d, 1H, J=8.0 Hz), 3.94 (t, 1H, J=5.5 Hz), 5.4 (dd, 1H, J=6.1, 15.0 Hz) and 5.76 (d, 1H, J=10.0 Hz) ppm; $^{13}$C{$^1$H} NMR (CDCl₃, 125 MHz) δ 19.3, 24.8, 24.9, 29.3, 67.0, 72.0, 78.1, 122.6, and 144.7 ppm; IR (neat) 3365, 2957, 2854, 1618, 1380, 1261, and 1091 cm$^{-1}$; HRMS-CI m/z 167.1439 [(M−OH)⁺; calcd for C₁₁H₁₉O: 167.1436].

Example 12

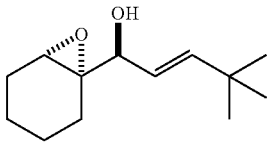

Preparation of erythro-(S)-4,4-Dimethyl-1-(7-oxa-bicyclo[4.1.0]hept-1-yl)-pent-2-en-1-ol (Table 2, Compound 3)

The product was prepared by General Procedure I using 98.5 mg (1.2 mmol) t-butyl acetylene, 1.2 mL (1.2 mmol, 1.0 M in hexanes) diethylborane, 2.2 mL (2.2 mmol, 1.0 M in hexanes) diethylzinc, 9.6 mg (0.04 mmol) (−)-MIB, 200 μL (0.20 mmol, 1.0 M in hexanes) Ti(O$^i$Pr)₄, and 114 μL (1.0 mmol) cyclohexenecarboxaldehyde. The crude product was purified by column chromatography on silica (10% ethyl acetate in hexanes) to afford the title compound as a colorless oil in 87% yield (183 mg, 0.87 mmol). [α]$_D^{20}$=−3.50 (c=0.40, CHCl₃); $^1$H NMR (CDCl₃, 500 MHz) δ 1.05 (s, 9H), 1.28 (m, 2H), 1.47 (m, 2H), 1.78 (m, 2H), 2.00 (m, 2H), 2.32 (br s, 1H), 3.27 (s, 1H), 4.01 (d, 1H, J=6.1 Hz), 5.31 (dd, 1H, J=5.9, 14.9 Hz), and 5.88 (d, 1H, J=14.9 Hz) ppm; $^{13}$C{$^1$H} NMR (CDCl₃, 125 MHz) δ 19.7, 20.2, 24.5, 24.9, 29.4, 35.1, 55.1, 62.0, 73.6, 122.6, and 146.6 ppm; IR (neat) 3431, 2931, 2859,

Example 13

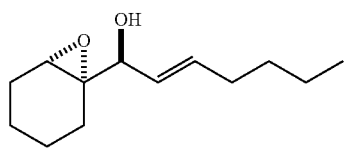

Preparation of erythro-(S)-1-(7-Oxa-bicyclo[4.1.0] hept-1-yl)-hept-2-en-1-ol (Table 2, Compound 4)

The product was prepared by General Procedure I using 98.6 mg (1.2 mmol) 1-hexyne, 1.2 mL (1.2 mmol, 1.0 M in hexanes) Et$_2$BH, 2.2 mL (2.2 mmol, 1.0 M in hexanes) diethylzinc, 9.6 mg (0.04 mmol) (−)-MIB, 114 μL (1.0 mmol) cyclohexenecarboxaldehyde, and 200 μL (0.20 mmol, 1.0 M in hexanes) Ti(O$^i$Pr)$_4$ was added to the reaction vessel. The crude product was purified by column chromatography on silica treated with triethylamine (10% ethyl acetate in hexanes) to afford the title compound as a colorless oil in 78% yield (164 mg, 0.78 mmol). [α]$_D^{20}$=−1.79 (c=1.78, CHCl$_3$); $^1$H NMR (C$_6$D$_6$, 360 MHz) δ 0.85 (t, 3H, J=5.0 Hz), 1.03 (m, 2H), 1.27 (m, 4H), 1.38 (m, 4H), 1.78 (m, 4H), 1.97 (m, 1H), 2.22 (br s, 1H), 3.13 (s, 1H), 3.95 (d, 1H, J=8.0 Hz), 5.52 (dd, 1H, J=8.0, 15.0 Hz), and 5.72 (m, 1H); $^{13}$C{$^1$H} NMR (C$_6$D$_6$, 90.6 MHz) δ 13.7, 19.7, 20.4, 22.1, 24.6, 24.8, 31.3, 32.0, 54.9, 61.5, 73.6, 128.8, and 133.9 ppm; IR (neat) 3402, 2925, 2856, 1722, 1445, 1260, 1021, and 800 cm$^{-1}$; HRMS-ESI m/z 210.1626 [M$^+$; calcd for C$_{13}$H$_{22}$O$_2$: 210.1620].

Example 14

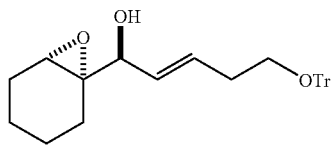

General Procedure J

Preparation of erythro-(S)-1-(7-Oxa-bicyclo[4.1.0] hept-1-yl)-3-trityloxy-prop-2-en-1-ol (Table 2, Compound 5)

374 mg (1.2 mmol) trityl protected 3-butyn-1-ol, was added to 1.2 mL (1.2 mmol, 1.0 M in hexanes) Et$_2$BH and stirred at room temp for 1 h. The solvent was removed in vacuo, and 1 mL of hexanes was added. In a separate flask, 9.6 mg (0.04 mmol) (−)-MIB, 114 μL (1.0 mmol) cyclohexenecarboxaldehyde, 1 mL of toluene, and 2.2 mL (2.2 mmol, 1.0 M in hexanes) diethylzinc were combined and stirred at −30° C. The hydroboration product was added to the reaction flask via syringe pump over 30 min, and the reaction was monitored by TLC. When no enal remained (after 5 h), the temperature was increased to −20° C., the reaction headspace was purged, and the reaction was exposed to dioxygen (1 atm). After 30 min, 200 μL (0.20 mmol, 1.0 M in hexanes) Ti(O$^i$Pr)$_4$ was added to the reaction vessel. After the reaction was complete, it was quenched with saturated aq NH$_4$Cl and extracted with hexanes (3×10 mL). The crude product was dried over MgSO$_4$, concentrated in vacuo, and purified by column chromatography on silica (10% ethyl acetate in hexanes) to afford the title compound as a colorless oil in 60% yield (264 mg, 0.60 mmol). [α]$_D^{20}$=−0.504 (c=1.19, CHCl$_3$); $^1$H NMR (CDCl$_3$, 500 MHz) δ 1.21 (s, 2H), 1.77 (m, 2H), 1.81 (m, 2H), 2.00 (m, 2H), 2.13 (m, 2H), 2.34 (br s, 1H), 2.80 (s, 2H), 3.57 (d, 1H, J=3.5 Hz), 3.80 (s, 1H), 5.46 (m, 1H), 5.5 (m, 1H), and 7.28 (m, 15H) ppm; $^{13}$C{$^1$H} NMR (CDCl$_3$, 125 MHz) δ 12.7, 13.5, 15.1, 20.4, 21.4, 21.6, 61.0, 64.1, 68.3, 73.6, 127.0, 127.4, 128.3, 128.5, 133.1, and 138.6 ppm; IR (neat) 3308, 3058, 2924, 2359, 1597, 1489, 1446, 1369, 1155, 1063, and 896 cm$^{-1}$; HRMS-CI m/z 440.2359 [M$^+$; calcd for C$_{30}$H$_{32}$O$_3$: 440.2351].

Example 15

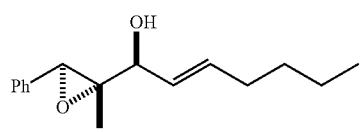

Preparation of erythro-(S)-1-(2-Methyl-3-phenyl-oxiranyl)-hept-2-en-1-ol (Table 2, Compound 6)

The product was prepared by General Procedure I using 98.6 mg (1.2 mmol) 1-hexyne, 1.2 mL (1.2 mmol, 1.0 M in hexanes) Et$_2$BH, 2.2 mL (2.2 mmol, 1.0 M in hexanes) diethylzinc, 9.6 mg (0.04 mmol) (−)-MIB, 200 μL (0.20 mmol, 1.0 M in hexanes) Ti(O$^i$Pr)$_4$, and 146 mg (1.0 mmol) □-methyl-trans-cinnamaldehyde. The crude product was purified by column chromatography on silica (10% ethyl acetate in hexanes) to afford the title compound as a colorless oil in 80% yield (197 mg, 0.80 mmol). [α]$_D^{20}$=−0.963 (c=1.04, CHCl$_3$); $^1$H NMR (CDCl$_3$, 500 MHz) δ 0.92 (t, 3H, J=9.0 Hz), 1.01 (m, 2H), 1.39 (m, 2H), 1.56 (s, 3H), 2.01 (m, 2H), 2.34 (s, 1H), 2.66 (br s, 1H), 4.22 (d, 1H, J=6.0 Hz), 5.50 (dd, 1H J=15.0, 6.0 Hz), 5.85 (dt, 1H, J=15.0, 6.0 Hz), and 7.35 (m, 5H), ppm; $^{13}$C{$^1$H} NMR (CDCl$_3$, 125 MHz) δ 13.5, 13.8, 22.2, 31.1, 32.0, 59.4, 65.9, 73.9, 126.3, 127.4, 127.5, 127.9, 128.1, and 136.1 ppm; IR (neat) 3388, 2924, 1628, 1442, 1262, and 1090 cm$^{-1}$; HRMS-CI m/z 229.1601 [(M−OH)$^+$; calcd for C$_{16}$H$_{21}$O$_1$: 229.1592].

Compounds from Table 3

Example 16

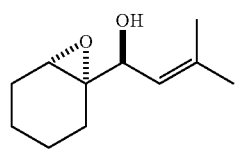

General Procedure K

Preparation of erythro-(S)-3-Methyl-1-(7-oxa-bicyclo[4.1.0]hept-1-yl)-but-2-en-1-ol (Table 3, Compound 1)

Di(2-methyl-propene)zinc (86 mg, 0.5 mmol), 1.5 mL (1.5 mmol, 1.0 M in hexanes) diethylzinc, 9.6 mg (0.04 mmol) (−)-MIB, and 1 mL of toluene were combined and stirred at 0° C. 114 μL (1.0 mmol) cyclohexenecarboxaldehyde was added, and the reaction was monitored by TLC. When no enal remained (after 6 h), the temperature was decreased to −20° C., the reaction headspace was purged, and the reaction was exposed to dioxygen (1 atm). After 30 min, 200 μL (0.20 mmol, 1.0 M in hexanes) Ti(O$^i$Pr)$_4$ was added to the reaction vessel. After the reaction was complete, it was quenched with saturated aq NH$_4$Cl and extracted with hexanes (3×10 mL). The crude product was dried over MgSO$_4$, concentrated in vacuo, and purified by column chromatography on silica (10% ethyl acetate in hexanes) to afford the title compound as a colorless oil in 61% yield (111 mg, 0.61 mmol). [α]$_D^{20}$=−3.33 (c=0.24, CHCl$_3$); $^1$H NMR (CDCl$_3$, 500 MHz) δ 0.89 (m, 2H), 1.31 (br s, 1H), 1.54 (m, 2H), 1.65 (m, 2H), 1.73 (s, 3H), 1.75 (s, 3H), 1.78 (m, 2H), 3.27 (s, 1H), 4.31 (d, 1H, J=9.1 Hz), and 5.06 (d, 1H, J=9.2 Hz) ppm; $^{13}$C{$^1$H} NMR (C$_6$D$_6$, 90.6 MHz) δ 18.3, 19.9, 20.4, 24.6, 25.0, 25.6, 54.4, 62.0, 68.9, 124.3, and 136.9 ppm; IR (neat) 3430, 2930, 1620, 1445, 1379, 1260, and 1036 cm$^{-1}$; HRMS-CI m/z 182.1304 [M$^+$; calcd for C$_{11}$H$_{18}$O$_2$: 182.1307].

Example 17

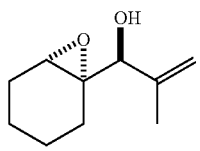

Preparation of erythro-(S)-2-Methyl-1-(7-oxa-bicyclo[4.1.0]hept-1-yl)-prop-2-en-1-ol (Table 3, Compound 2)

The product was prepared by General Procedure K using di(1-methyl-ethylene)zinc (73 mg, 0.5 mmol), 1.5 mL (1.5 mmol, 1.0 M in hexanes) diethylzinc, 9.6 mg (0.04 mmol) (−)-MIB, 114 μL (1.0 mmol) cyclohexenecarboxaldehyde, and 200 μL (0.20 mmol, 1.0 M in hexanes) Ti(O$^i$Pr)$_4$. The crude product was purified by column chromatography on silica (10% ethyl acetate in hexanes) to afford the title compound as a colorless oil in 90% yield (151 mg, 0.90 mmol). [α]$_D^{20}$=−5.83 (c=1.2, CHCl$_3$); $^1$H NMR (CDCl$_3$, 500 MHz) δ 1.23 (m, 2H), 1.54 (s, 3H), 1.67 (m, 2H), 1.79 (m, 2H), 1.93 (m, 2H), 2.02 (br s, 1H), 3.35 (s, 1H), 4.03 (s, 1H), 4.99 (1H, s), and 5.05 (s, 1H) ppm; $^{13}$C{$^1$H} NMR (C$_6$D$_6$, 90.6 MHz) δ 18.1, 19.7, 20.2, 24.4, 24.6, 54.9, 60.5, 76.4, 113.8, and 144.3 ppm; IR (neat) 3398, 2360, 1621, 1498, 1220, and 1007 cm$^{-1}$; LRMS-CI m/z 167.11[(M−H)$^+$; calcd for C$_{10}$H$_{15}$O$_2$: 167.11].

Example 18

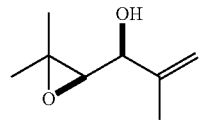

Preparation of threo-(S)-1-(3,3,-Dimethyl-oxiranyl)-2-methyl-prop-2-en-1-ol (Table 3, Compound 3)

The product was prepared by General Procedure K using Di(1-methyl-ethylene)zinc (73 mg, 0.5 mmol), 1.5 mL (1.5 mmol, 1.0 M in hexanes) diethylzinc, 9.6 mg (0.04 mmol) (−)-MIB, 84 mg (1.0 mmol) 3-methyl-but-2-enal, and 200 μL (0.20 mmol, 1.0 M in hexanes) Ti(O$^i$Pr)$_4$. The crude product was purified by column chromatography on silica (10% ethyl acetate in hexanes) to afford the title compound as a colorless oil in 91% yield (194 mg, 0.43 mmol). [α]$_D^{20}$=−5.00 (c=0.22, CHCl$_3$); $^1$H NMR (CDCl$_3$, 500 MHz) δ 1.29 (s, 3H), 1.30 (s, 3H), 1.74 (s, 3H), 2.02 (br s, 1H), 2.73 (d, 1H, J=, 6.0 Hz), 3.87 (d, 1H, J=6.0 Hz), 4.90 (s, 1H), and 5.02 (s, 1H) ppm; $^{13}$C{$^1$H} NMR (C$_6$D$_6$, 125 MHz) δ 18.9, 19.5, 24.8, 59.3, 67.1, 73.7, 111.7, and 128.4 ppm; IR (neat) 3390, 2950, 2924, 1601, 1430, 1260, and 1090 cm$^{-1}$; HRMS-CI m/z 125.0966 [(M−OH)$^+$; calcd for C$_8$H$_{13}$O$_1$: 125.0966].

Example 19

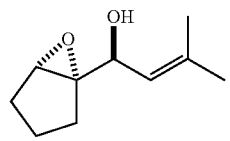

Preparation of erythro-(S)-3-Methyl-1-(6-oxa-bicyclo[3.1.0]hex-1-yl)-but-2-en-1-ol (Table 3, Compound 4)

The product was prepared by General Procedure K using di(2-methyl-propene)zinc (86 mg, 0.5 mmol), 1.5 mL (1.5 mmol, 1.0 M in hexanes) diethylzinc, 9.6 mg (0.04 mmol) (−)-MIB, 96 mg (1.0 mmol) cyclopentanecarboxaldehyde, and 200 μL (0.20 mmol, 1.0 M in hexanes) Ti(O$^i$Pr)$_4$. The crude product was purified by column chromatography on silica (10% ethyl acetate in hexanes) to afford the title compound as a colorless oil in 76% yield (127.7 mg, 0.76 mmol). [α]$_D^{20}$=−5.00 (c=1.0, CHCl$_3$); $^1$H NMR (CDCl$_3$, 500 MHz) δ 1.28 (m, 2H), 1.55 (m, 2H), 1.56 (s, 3H), 1.67 (s, 3H), 1.80 (m, 2H), 1.98 (br s, 1H), 3.44 (s, 1H), 4.61 (d, 1H, J=10.0 Hz), and 5.08 (d, 1H, J=10.0 Hz) ppm; $^{13}$C{$^1$H} NMR (C$_6$D$_6$, 75 MHz) δ 18.7, 20.1, 26.1, 27.2, 27.8, 60.7, 67.3, 71.1, 125.8 and 137.5 ppm; IR (neat) 3410, 2957, 1624, 1413, 1261, 1089, and 800 cm$^{-1}$; LRMS-CI m/z 167.23 [(M−H)$^+$; calcd for C$_{10}$H$_{15}$O$_2$: 167.22].

Example 20

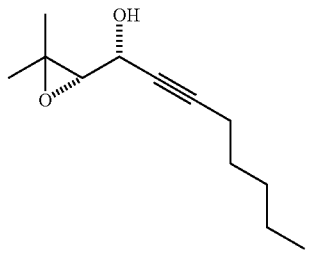

Preparation of threo-(S)-1-(3,3-Dimethyl-oxiranyl)-oct-2-yn-1-ol (Table 3, Compound 5)

The product was prepared by General Procedure K using di(2-methyl-propene)zinc (86 mg, 0.5 mmol), 1.5 mL (1.5 mmol, 1.0 M in hexanes) diethylzinc, 9.6 mg (0.04 mmol) (−)-MIB, 124.1 mg (1.0 mmol) oct-2-ynal, and 200 μL (0.20 mmol, 1.0 M in hexanes) Ti(O$^i$Pr)$_4$. The crude product was purified by column chromatography on silica (10% ethyl acetate in hexanes) to afford the title compound as a colorless oil in 92% yield (180 mg, 0.92 mmol). [α]D$^{20}$=−0.571 (c=0.35, CHCl$_3$); $^1$H NMR (CDCl$_3$, 500 MHz) δ 0.87 (t, 3H, J=5.0 Hz), 1.23 (m, 2H), 1.32 (s, 3H), 1.33 (s, 3H), 1.49 (q, 2H, J=7.0 Hz), 2.01 (br s, 1H), 2.14 (d, 2H, J=2.0 Hz), 2.20 (t, 2H, J=8.7 Hz), 2.94 (d, 1H, J=7.8 Hz), and 4.15 (d, 1H, J=7.8 Hz) ppm; $^{13}$C{$^1$H} NMR (C$_6$D$_6$, 90.6 MHz) δ 13.8, 18.6, 18.8, 22.2, 24.3, 28.3, 30.9, 58.0, 62.6, 67.0, 78.4, and 86.8 ppm; IR (neat) 3391, 2979, 2969, 2929, 2359, 2101, 1457, 1380, 1260, 1092, and 1020 cm$^{-1}$; HRMS-CI m/z 197.1542 [(M+H)$^+$; calcd for C$_{12}$H$_{21}$O$_2$: 197.1538].

Example 21

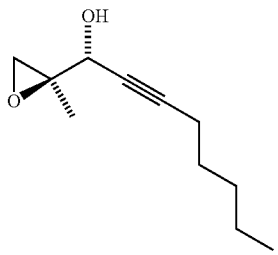

Preparation of erythro-(S)-1-(2-Methyl-oxiranyl)-oct-2-yn-1-ol (Table 3, Compound 6)

The product was prepared by General Procedure K using di(1-methyl-ethylene)zinc (73 mg, 0.5 mmol), 1.5 mL (1.5 mmol, 1.0 M in hexanes) diethylzinc, 9.6 mg (0.04 mmol) (−)-MIB, 124.1 mg (1.0 mmol) oct-2-ynal, and 200 μL (0.20 mmol, 1.0 M in hexanes) Ti(O$^i$Pr)$_4$. The crude product was purified by column chromatography on silica (10% ethyl acetate in hexanes) to afford the title compound as a colorless oil in 90% yield (164 mg, 0.90 mmol). [α]$_D^{20}$=−0.590 (c=0.21, CHCl$_3$); $^1$H NMR (CDCl$_3$, 500 MHz) δ 0.88 (q, 3H, J=5.0 Hz), 1.23 (m, 4H), 1.32 (s, 3H), 1.51 (m, 2H), 2.05 (br s, 1H), 2.22 (t, 2H, J=8.0 Hz), 2.65 (d, 1H, J=5.0 Hz), 2.99 (d, 1H, J=5.0 Hz), 4.36 (s, 1H) ppm; $^{13}$C{$^1$H} NMR (C$_6$D$_6$, 90.6 MHz) δ 13.8, 17.2, 18.6, 22.2, 28.3, 30.7, 50.7, 58.3, 64.8, 78.3, and 86.3 ppm; IR (neat) 3360, 2923, 2359, 2126, 1731, 1461 and 1154 cm$^{-1}$; HRMS-CI m/z 183.1389[(M H)$^+$; calcd for C$_{11}$H$_{19}$O$_2$: 183.1385].

Example 22

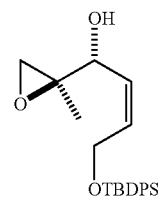

Preparation of erythro-(S)-4-(Isopropyl-diphenyl-silanyloxy)-1-(2-methyl-oxiranyl)-but-2-en-1-ol (Table 3, Compound 7)

The product was prepared by General Procedure K using di(1-methyl-ethylene)zinc (73 mg, 0.5 mmol), 1.5 mL (1.5 mmol, 1.0 M in hexanes) diethylzinc, 9.6 mg (0.04 mmol) (−)-MIB, 234.5 mg, 1 mL (1.0 mmol, 1.0 M in hexanes) 4-(tert-butyl-diphenyl-silanyloxy)-but-2-enal, and 200 μL (0.20 mmol, 1.0 M in hexanes) Ti(O$^i$Pr)$_4$. The crude product was purified by column chromatography on silica (10% ethyl acetate in hexanes) to afford the title compound as a colorless oil in 80% yield (306 mg, 0.80 mmol). [α]D$^{20}$=−0.047 (c=4.3, CHCl$_3$); $^1$H NMR (CDCl$_3$, 500 MHz) δ 1.05 (s, 9H), 1.23 (s, 3H) 2.87 (br s, 1H), 2.88 (s, 2H), 4.26 (d, 1H, J=13.0 Hz), 4.35 (d, 2H, J=14.0 Hz), 5.45 (dt, 1H, J=6.0, 14.0 Hz), 5.95 (m, 1H), 7.43 (m, 5H), and 7.70 (m, 5H) ppm; $^{13}$C{$^1$H} NMR (CDCl$_3$, 125 MHz) δ 17.8, 19.1, 26.8, 50.2, 58.7, 60.4, 68.8, 127.7, 128.4, 129.9, 133.9, 134.8, and 135.5 ppm; IR (neat) 3340, 2927, 1594, 1260, and 1006 cm$^{-1}$; HRMS-ESI m/z 405.1870 [(M−Na)$^+$; calcd for C$_{23}$H$_{30}$O$_3$NaSi: 405.1862].

Example 23

Conditions for the Determination of Enantiomeric Excess

The enantiomeric excess values for the following epoxy alcohols were determined by chiral HPLC analysis using a Chiralcel OD-H column. The conditions for the resolution of the racemates are described below.

(Table 2, Compound 5) 1-(7-Oxa-bicyclo[4.1.0]hept-1-yl)-3-trityloxy-prop-2-en-1-ol. t$_1$=7.6 min, t$_2$=13.2 min (hexanes/2-propanol: 95/5, 0.5 mL/min)

(Table 2, Compound 6) 1-(2-Methyl-3-phenyl-oxiranyl)-hept-2-en-1ol. t$_1$=5.9 min, t$_2$=6.6 min (hexanes/2-propanol: 95/5, 0.5 mL/min).

(Table 2, Compound 7) 1-(3-tert-Butyl-oxiranyl)-2-methyl-3-phenyl-prop-2-en-1-ol. t$_1$=10.1 min, t$_2$=11.1 min (hexanes/2-propanol: 97/3, 0.3 mL/min).

(Table 3, Compound 7) 4-(Isopropyl-diphenyl-silanyloxy)-1-(2-methyl-oxiranyl)-but-2-en-1-ol. t$_1$=16.4 min, t$_2$=18.4 min (hexanes/2-propanol: 97/3, 1.0 mL/min).

The enantiomeric excess values for the following epoxy alcohols were determined by chiral capillary GC analysis using a Supleco β-Dex 120 fused silica column (30 m×0.25 mm×0.25 μm film thickness). The carrier gas was nitrogen; inlet temperature was 250° C.; FID detector at 270° C. The conditions for the resolution of the racemates are described below.

(Table 2, Compound 1) 7-Chloro-1-(7-oxa-bicyclo[4.1.0]hept-1-yl)-hept-2-en-1-ol. $t_1$=53.4 min, $t_2$=65.0 min (100° C., 1.0 mL/min).

(Table 2, Compound 2) 1-(3,3-Dimethyl-oxiranyl)-4,4-dimethyl-pent-2-en-1-ol. $t_1$=47.2 min, $t_2$=53.1 min (100° C., 1.0 mL/min).

(Table 2, Compound 3) 4,4-Dimethyl-1-(7-oxa-bicyclo[4.1.0]hept-1-yl)-pent-2-en-1-ol. $t_1$=100.2 min, $t_2$=113.4 min (120° C., 1.0 mL/min).

(Table 2, Compound 4) 1-(7-Oxa-bicyclo[4.1.0]hept-1-yl)-hept-2-en-1-ol. $t_1$=9.1 min, $t_2$=19.2 min (100° C., 1.0 mL/min).

(Table 3, Compound 1) 3-Methyl-1-(6-oxa-bicyclo[3.1.0]hex-1-yl)-but-2-en-1-ol. $t_1$=277.4 min, $t_2$=284.0 min (90° C., 0.5 mL/min).

(Table 3, Compound 2) 2-Methyl-1-(7-oxa-bicyclo[4.1.0]hept-1-yl)-prop-2-en-1-ol. $t_1$=18.4 min, $t_2$=20.5 min (110° C., 1.0 mL/min).

(Table 3, Compound 3) 1-(3,3,-Dimethyl-oxiranyl)-2-methyl-prop-2-en-1-ol. $t_1$=6.2 min, $t_2$=16.6 min (110° C., 1.0 mL/min).

(Table 3, Compound 4) 3-Methyl-1-(6-oxa-bicyclo[3.1.0]hex-1-yl)-but-2-en-1-ol. $t_1$=103.8 min, $t_2$=108.9 min (130° C., 1.0 mL/min).

(Table 3, Compound 5) 1-(3,3-Dimethyl-oxiranyl)-oct-2-yn-1-ol. $t_1$=75.8 min, $t_2$=82.0 min (130° C., 1.0 mL/min).

(Table 3, Compound 6) 1-(2-Methyl-oxiranyl)-oct-2-yn-1-ol. $t_1$=17.9 min, $t_2$=26.0 min (100° C., 1.0 mL/min).

Substrates and Products From Table 4

Example 24

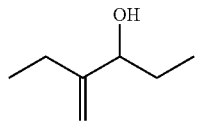

General Procedure L

Preparation of (S)-2-Ethyl-pent-1-en-3-ol

A 10 mL Schlenk flask was charged with (−)-MIB (1.9 mg, 0.008 mmol) and 1 mL hexanes and cooled to 0° C. A hexanes solution of Et$_2$Zn (0.2 mL, 2.0 M) was added, followed by addition of 2-ethylpropenal (16.8 mg, 0.2 mmol) dropwise. The reaction was stirred at 0° C. for 8 h and quenched with a saturated solution of aq NH$_4$Cl. The organic and aqueous layers were separated, and the aqueous layer was extracted with hexanes. The combined organic layers were then washed with brine and H$_2$O and dried over MgSO$_4$. The filtrate was concentrated in vacuo and the residue was chromatographed on silica (20% ethyl acetate in hexanes) to afford the title compound as a colorless oil in 80% yield (45.7 mg, 0.2 mmol). $[\alpha]_D^{20}$=−0.031 (c=0.003, CHCl$_3$, 93% ee); $^1$H NMR and $^{13}$C NMR spectra for this compound compare with previously reported literature data.

Example 25

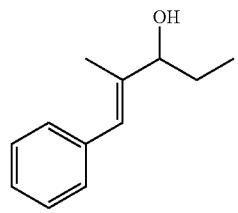

Preparation of (S)-2-Methyl-1-phenyl-pent-1-en-3-ol

The product was prepared by General procedure L using 0.1 mL (0.2 mmol, 2.0 M in hexanes) Et$_2$Zn, 1.0 mg (0.004 mmol) (−)-MIB, and 15 mg (0.1 mmol) 2-methyl-cinnamaldehyde. The crude product was purified by column chromatography on silica (20% ethyl acetate in hexanes) to afford the title compound as a colorless oil in 80% yield (17.6 mg, 0.1 mmol): $[\alpha]_D^{20}$=−10.67 (c=0.003, CHCl$_3$, 95% ee); $^1$H NMR (CDCl$_3$, 500 MHz) δ 7.32 (m, 2H), 7.20 (m, 3H), 6.48 (s, 1H), 4.09 (t, 1H J=5.0 Hz), 1.85 (s, 3H), 1.67 (m, 2H) and 0.93 (t, 3H, J=7.3 Hz) ppm; $^{13}$C{$^1$H} NMR (CDCl$_3$, 125 MHz): δ 140.08, 137.64, 128.97, 128.09, 126.40, 125.97, 79.52, 27.95, 13.09, and 10.05 ppm; IR (neat) 3403.8, 2962.3, 2931.2, 2872.3, 2364.1, 1452.4, 1374.8, 1260.1, and 1187.2 cm$^{-1}$. HRMS-CI m/z 176.1196 [M$^+$; calcd for C$_{12}$H$_{16}$O: 176.1201].

Example 26

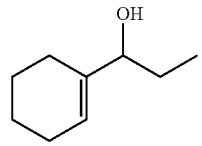

Preparation of (S)-1-Cyclohex-1-enyl-propan-1-ol

The product was prepared by General procedure L using 0.28 mL (0.55 mmol, 2.0 M in hexanes) Et$_2$Zn, 4.8 mg (0.02 mmol) (−)-MIB, and 55 mg (0.50 mmol) cyclohexenecarboxaldehyde. The crude product was purified by column chromatography on silica (10% ethyl acetate in hexanes) to afford the title compound in 90% yield (104 mg, 0.39 mmol) as a colorless oil, $[\alpha]_D^{20}$=−3.4 (c=0.005, CHCl$_3$, 99% ee); $^1$H NMR (CDCl$_3$, 500 MHz): δ 0.8 (t, 3H, J=7.5 Hz), 1.3 (br s, 2H), 1.5-1.6 (m, 4H), 1.8 (s, 1H), 2.0 (s, 4H) 3.84 (q, 1H, J=10.0 Hz), and 5.63 (s, 1 H) ppm; $^{13}$C{$^1$H} NMR (CDCl$_3$, 125 MHz): δ 10.1, 22.6, 23.3, 24.9, 27.6, 29.6, 78.1, 123.2, and 139.6 ppm; IR (neat) 3500, 2962, 2922, 2874, 2360,

Example 27

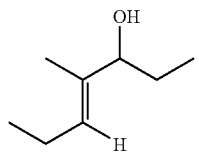

Preparation of (S)-4-Methyl-hept-4-en-3-ol

The product was prepared by General procedure L using 1.0 mL (2.0 mmol, 2.0 M in hexanes) Et$_2$Zn, 9.6 mg (0.04 mmol) (−)-MIB, and 114 µL (1.0 mmol) 2-methyl-2-pentenal. The crude product was purified by column chromatography on silica (10% ethyl acetate in hexanes) to afford the title compound as a colorless oil in 73% yield (93 mg, 0.73 mmol). [α]$_D^{20}$=−5.8 (c=0.73, CHCl$_3$, 95% ee); $^1$H NMR (CDCl$_3$, 500 MHz) δ 0.77 (t, 3H, J=7.4 Hz), 0.89 (t, 3H, J=7.5 Hz), 1.45-1.49 (m, 2H), 1.51 (s, 3H), 1.61 (br s, 1H), 1.96 (q, 2H, J=7.4 Hz), 3.81 (t, 1H, J=6.7 Hz), and 5.29 (t, 1H, J=6.9 Hz) ppm; $^{13}$C {$^1$H} NMR (CDCl$_3$, 125 MHz) δ 10.0, 10.8, 14.0, 20.7, 27.6, 79.4, 128.6, and 136.1 ppm; IR (neat) 3360, 2962, 2932, 2875, 2348, 1722, 1670, 1461, 1376, 1335, 1308, 1261, 1097, 1054, and 1008 cm$^{-1}$; HRMS-CI m/z 128.1206 [M$^+$; calcd for C$_8$H$_{16}$O: 128.1201].

Example 28

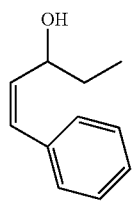

Preparation of (S)-1-Phenyl-pent-1-en-ol

The product was prepared by General procedure L using 0.25 mL (0.50 mmol, 2.0 M in hexanes) Et$_2$Zn, 2.4 mg (0.01 mmol) (−)-MIB, and 32 µL (0.25 mmol) cis-cinnamaldehyde. The crude product was purified by column chromatography on silica (10% ethyl acetate in hexanes) to afford the title compound as a colorless oil in 90% yield (37 mg, 0.23 mmol). [α]$_D^{20}$=−5.2 (c=1.3, CHCl$_3$, 91% ee); $^1$H NMR (CDCl$_3$, 500 MHz) δ 0.97 (t, 3H, J=7.4 Hz), 1.65 (m, 2H), 1.79 (br s, 1H), 4.20 (dt, 1H, J=6.5, 6.4 Hz), 6.20 (dd, 1H, J=15.9, 6.7 Hz), 6.56 (d, 1H, J=15.9 Hz), 7.23 (t, 1H, J=7.3 Hz), 7.30 (t, 2H, J=7.4 Hz), and 7.37 (d, 2H, J=7.4 Hz) ppm; $^{13}$C{$^1$H} NMR (CDCl$_3$, 125 MHz) δ 9.68, 30.2, 74.3, 126.4, 127.5, 128.5, 130.3, 132.3, and 136.7 ppm; IR (neat) 3355, 3081, 3059, 3026, 2959, 2923, 2853, 2726, 235, 1946, 1876, 1802, 1713, 1732, 1456, and 1260 cm$^{-1}$. HRMS-CI m/z 123.1174 [(M−OH)$^+$; calcd for C$_9$H$_{15}$: 123.1173].

Example 29

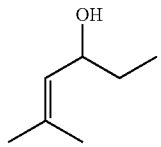

Preparation of (S)-5-Methyl-hex-4-en-3-ol

The product was prepared by General procedure L using 1.0 mL (2.0 mmol, 2.0 M in hexanes) Et$_2$Zn, 10 mg (0.04 mmol) (−)-MIB, and 84 mg (1.0 mmol) 3-methylbut-2-en-al. The crude product was purified by column chromatography on silica (20% ethyl acetate in hexanes) to afford the title compound as a colorless oil in 82% yield (93.6 mg, 0.82 mmol). [α]$_D^{20}$=−10.5 (c=0.002, CHCl$_3$, 95% ee); $^1$H NMR and $^{13}$C NMR spectra for this compound compare with previously reported literature data.

Example 30

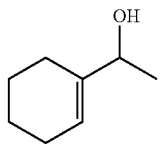

General Procedure M

Preparation of (S)-1-Cyclohex-1-enyl-ethanol

A 10 mL Schlenk flask was charged with bis(sulfonamide) ligand 2 (3.8 mg, 0.01 mmol), Ti(OtBu)$_4$ (193 µL, 0.50 mmol), and 0.5 mL hexanes and stirred for 30 min at room temp. A hexanes solution of Me$_2$Zn (0.32 mL, 0.63 mmol) was then added, and after stirring for 10 min, cyclohexenecarboxaldehyde (28 µL, 0.25 mmol) was added. The reaction was stirred at room temp for 19 h and quenched with a saturated solution of aq NH$_4$Cl. The organic and aqueous layers were separated, and the aqueous layer was extracted with hexanes. The combined organic layers were then washed with brine and H$_2$O and dried over MgSO$_4$. The filtrate was concentrated in vacuo and the residue was chromatographed on silica (10% ethyl acetate in hexanes) to afford the title compound as a colorless oil in 94% yield (30 mg, 0.23 mmol). $^1$H NMR (CDCl$_3$, 500 MHz) δ 1.20 (d, 3H, J=6.2 Hz), 1.51 (m, 4H), 1.61 (br s, 1H), 1.99 (m, 4H), 4.10 (q, 1H, J=6.2 Hz), and 5.61 (br t, 1H) ppm; $^{13}$C{$^1$H} NMR (CDCl$_3$; 125 MHz) δ 21.4, 22.5, 22.6, 23.6, 24.8, 72.0, 121.3, and 141.2 ppm. $^1$H 1646, 1599, 1578, 1492, 1463, 1378, 1332, 1300, 1261, and 1129 cm$^{-1}$; HRMS-CI m/z 145.1019 [(M−OH)$^+$; calcd for C$_{11}$H$_{13}$: 145.1017].

Example 31

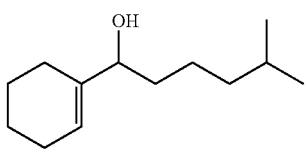

Preparation of (S)-1-Cyclohex-1-enyl-5-methyl-hexan-1-ol

The product was prepared by General procedure L using 1.0 mL (1.0 mmol, 1.0 M in hexanes) dialkylzinc, 5.0 mg (0.02 mmol) (−)-MIB, and 55 mg (0.5 mmol) cyclohexencarboxaldehyde. The crude product was purified by column chromatography on silica (20% ethyl acetate in hexanes) to afford the title compound as a colorless oil in 86% yield (84.4 mg, 0.43 mmol): $[\alpha]_D^{20}$=−20.0 (c=0.001, CHCl$_3$, 97% ee); $^1$H NMR (CDCl$_3$, 500 MHz) δ 5.63 (s, 1H), 3.93 (t, 1H J=5.0 Hz), 2.02 (m, 2H), 1.89 (m, 1H), 1.63-1.58 (m, 2H), 1.55-1.49 (m, 2H), 1.37-1.26 (m, 6H), 1.24-1.14 (m, 2H) and 0.85 (d, 6H J=6.0 Hz) ppm; $^{13}$C{$^1$H} NMR (CDCl$_3$, 125 MHz): δ 140.073, 123.0, 76.82, 38.91, 35.10, 27.88, 24.97, 23.60, 23.36, 22.67, 22.60, 22.54, and 14.07 ppm; IR (neat) 3500, 2927.4, 2369.0, 2341.2, 1684.7, 1456.0, 1385.7, and 1261.4 cm$^{-1}$. HRMS-CI m/z 195.1741 [(M−H)$^+$; calcd for C$_{13}$H$_{23}$: 195.1742].

Example 32

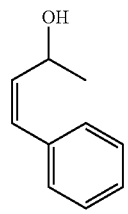

Preparation of (S)-4-Phenyl-but-3-en-2-ol

The product was prepared by General procedure M using 4.5 mg (0.012 mmol) ligand 2, 0.30 mL (0.60 mmol, 2.0 M in hexanes) Me$_2$Zn, 116 µL (0.30 mmol) Ti(OtBu)$_4$, and 19 µL (0.15 mmol) cis-cinnamaldehyde. The crude product was purified by column chromatography on silica (10% ethyl acetate in hexanes) to afford the title compound as a colorless oil in 91% yield (20 mg, 0.14 mmol). $^1$H NMR (CDCl$_3$, 500 MHz) δ □ □□ (d, 3H, J=6.2 Hz), 1.66 (br s, 1H), 4.69 (dq, 1H, J=8.5, 6.4 Hz), 5.60 (dd, 1H, J=11.5, 9.3 Hz), 6.40 (d, 1H, J=11.6 Hz), 7.18 (d, 2H, J=7.4 Hz), and 7.25 (t, 3H, J=7.5 Hz) ppm; $^{13}$C{$^1$H} NMR (CDCl$_3$, 125 MHz) δ 23.6, 64.1, 127.2, 128.3, 128.8, 130.0, 135.7, and 136.7 ppm; $^1$H NMR and $^{13}$C NMR spectra for this compound compare with previously reported literature data.

Example 33

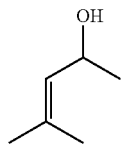

Preparation of (S)-4-Methyl-pent-3-en-2-ol

The product was prepared by General Procedure B using 7.6 mg (0.02 mmol) ligand 2, 0.50 mL (1.0 mmol, 2.0 M in hexanes) Me$_2$Zn, 193 µL (0.50 mmol) Ti(OtBu)$_4$, and 21 µL (0.25 mmol) 3-methylbut-2-en-al. The crude product was purified by column chromatography on silica (10% ethyl acetate in hexanes) to afford the title compound as a colorless oil in 68% yield (17 mg, 0.17 mmol). $^1$H NMR (CDCl$_3$, 500 MHz) δ 1.20 (d, 3H, J=6.2 Hz), 1.57 (br s, 1H), 1.66 (s, 3H), 1.68 (s, 1H), 4.52 (dq, 1H, J=8.1, 6.4 Hz), and 5.18 (d, 1H, J=8.4 Hz) ppm; $^{13}$C{$^1$H} NMR (CDCl$_3$, 125 MHz) δ 17.9, 23.6, 25.6, 64.7, 129.4, and 134.0 ppm; $^1$H NMR and $^{13}$C NMR spectra for this compound compare with previously reported literature data.

Example 34

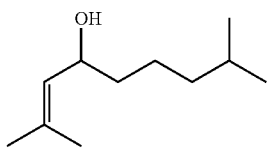

Preparation of (S)-2,8-Dimethyl-non-2-en-4-ol

The product was prepared by General procedure L using 1.0 mL (1.0 mmol, 1.0 M in hexanes) dialkylzinc, 5.0 mg (0.02 mmol) (−)-MIB, and 48 µL (0.5 mmol) 3-methylbut-2-en-al. The crude product was purified by column chromatography on silica (2.0% ethyl acetate in hexanes) to afford the title compound as a colorless oil in 80% yield (68.0 mg, 0.5 mmol): $[\alpha]_D^{20}$=−45.0 (c=0.002, CHCl$_3$, 96% ee); $^1$H NMR (CDCl$_3$, 500 MHz) δ 5.14 (d, 1H, J=8.5 Hz), 4.3 (q, 1H, J=5.0 Hz), 1.70 (s, 3H), 1.66 (s, 3H), 1.50 (t, 1H, J=5.5 Hz), 1.18-1.14 (m, 6H), and 0.85 (q, 6H, J=5.0 Hz) ppm; $^{13}$C{$^1$H} NMR (CDCl$_3$, 125 MHz): δ 134.9, 128.32, 68.72, 38.92, 37.96, 27.92, 25.73, 23.22, 22.57, 22.53, and 18.19 ppm; IR (neat)

3412.4, 2960.0, 2871.8, 2362.1, 1651.9, 1457.3, 1381.9, 1260.5, and 1260 cm$^{-1}$. LRMS-CI m/z 152.16 [(M–H$_2$O)$^+$; calcd for C$_{11}$H$_{20}$: 152.16].

Example 35

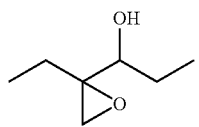

General Procedure N

Preparation of erythro-1-(2-Ethyl-oxiranyl)-propan-1-ol

A 10 mL Schlenk flask was charged with (–)-MIB (5.0 mg, 0.5 mmol) and 1 mL hexanes and cooled to 0° C. A hexanes solution of Et$_2$Zn (0.5 mL, 2.0 M) was added, followed by addition of 2-ethylpropenal (52 µL, 0.5 mmol) dropwise. The reaction was stirred at 0° C. for 8 h until alkyl addition was complete by TLC. The reaction flask was then capped with a balloon of oxygen. After stirring at 0° C. for 1 h, the reaction flask was cooled to –20° C., and a hexanes solution of Ti(O-iPr)$_4$ (0.05 mL, 1.0 M) was added. The reaction continued to stir at –20° C. under an O$_2$ atmosphere for 18 h. It was then quenched with 15% tartaric acid solution, allowed to stir for 45 min, then poured into a separatory funnel with a solution of Na$_2$S$_2$O$_4$. The organic and aqueous layers were separated, and the aqueous layer was extracted with hexanes. The combined organic layers were then washed with brine and H$_2$O and dried over MgSO$_4$. The filtrate was concentrated in vacuo and the residue was chromatographed on silica (20% ethyl acetate in hexanes) to afford the title compound as a colorless oil in 60% yield (39 mg, 0.3 mmol): [α]$_D^{20}$=–3.0 (c=0.008, CHCl$_3$); $^1$H NMR (CDCl$_3$, 500 MHz) δ 3.85 (d, 1H, J=8.0 Hz), 3.38 (d, 1H, J=8.0 Hz), 2.39 (t, 1H, J=9.0 Hz), 1.95-1.91 (m, 2H), 1.70-1.57 (m, 2H) and 0.91 (t, 6H J=7.2 Hz) ppm; $^{13}$C{$^1$H} NMR (CDCl$_3$, 125 MHz): δ 71.0, 62.1, 48.2, 25.8, 23.9, 9.9, and 8.0 ppm; IR (neat) 3400.3, 2942.1, 2836.1, 2358.9, 1651.8, 1460.1, and 1259.1 cm$^{-1}$. HRMS-CI m/z 113.0973 [(M–OH)$^+$; calcd for C$_7$H$_{13}$O: 113.0967].

Example 36

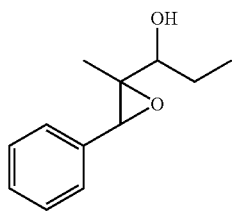

Preparation of erythro-1-(2-Methyl-3-phenyl-oxiranyl)-propan-1-ol

The product was prepared by General procedure N using 0.5 mL (1.0 mmol, 2.0 M in hexanes) Et$_2$Zn, 5 mg (0.02 mmol) (–)-MIB, 73 mg (0.5 mmol) 2-methylcinnamaldehyde, and 0.05 mL (0.05 mmol, 1.0 M in hexanes) Ti(OiPr)$_4$. The crude product was purified by column chromatography on silica (20% ethyl acetate in hexanes) to afford the title compound as a colorless oil in 65% yield (62.4 mg, 0.325 mmol): [α]$_D^{20}$=–27.2 (c=0.005, CHCl$_3$); $^1$H NMR (CDCl$_3$, 500 MHz) δ 7.33 (m, 2H), 7.26 (m, 3H), 4.17 (s, 1H), 3.74 (dd, 1H, J=3.1 Hz), 2.25 (s, 1H), and 1.6 (m, 2H) ppm; $^{13}$C{$^1$H} NMR (CDCl$_3$, 125 MHz): δ 135.7, 128.12, 127.48, 126.23, 73.34, 59.49, 25.66, 13.66, and 9.76 ppm; IR (neat) 3452, 2964, 2933, 2877, 1605, 1498, 1451, 1384, 1227 cm$^{-1}$. HRMS-CI m/z 175.1120 [(M–OH)$^+$; calcd for C$_{12}$H$_{15}$: 175.1122].

Example 37

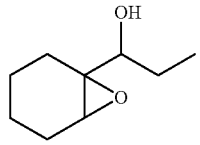

Preparation of erythro-1-(7-Oxa-bicyclo[4.1.0]hept-1-yl)-propan-1-ol

The product was prepared by General procedure N using 0.5 mL (1.0 mmol, 2.0 M in hexanes) Et$_2$Zn, 5 mg (0.02 mmol) (–)-MIB, 55 mg (0.5 mmol) cyclohexencarboxaldehyde, and 0.05 mL (0.05 mmol, 1.0 M in hexanes) Ti(OiPr)$_4$. The crude product was purified by column chromatography on silica (20% ethyl acetate in hexanes) to afford the title compound as a colorless oil in 90% yield (70.2 mg, 0.45 mmol): [α]$_D^{20}$=–18.64 (c=0.011, CHCl$_3$); $^1$H NMR (CDCl$_3$, 500 MHz) δ 3.46 (d, 1H J=6.0 Hz), 3.19 (s, 1H), 2.16 (s, 1H), 1.95 (dt, 2H, J=15.3, 6.0 Hz), 1.77-1.65 (m, 3H), 1.47-1.38 (m, 2H), 1.27-1.20 (m, 2H), and 0.98 (t, 3H J=7.25 Hz) ppm; $^{13}$C{$^1$H} NMR (CDCl$_3$, 125 MHz): δ 72.91, 62.03, 55.44, 25.66, 25.10, 24.43, 20.31, 19.71, and 9.99 ppm; IR (neat), 3333.6, 2918.1, 2354.4, 2322.3, 1644.3, 1448.3, and 1259.6 cm$^{-1}$. HRMS-CI m/z 139.1116 [(M–OH)$^+$; calcd for C$_9$H$_{16}$O$_2$: 139.1123].

Example 38

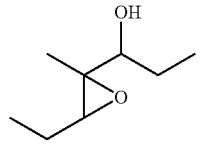

Preparation of erythro-1-(3-Ethyl-2-methyl-oxiranyl)-propan-1-ol

The product was prepared by General procedure N using 0.75 mL (1.5 mmol, 2.0 M in hexanes) Et$_2$Zn, 4.8 mg (0.02 mmol) (–)-MIB, 57 µL (0.5 mmol) 2-methyl-2-pentenal, and 50 µL (0.05 mmol, 1.0 M in hexanes) Ti(OiPr)$_4$. The crude product was purified by column chromatography on silica (10% ethyl acetate in hexanes) to afford the title compound as a colorless oil in 81% yield (58 mg, 0.40 mmol). [α]$_D^{20}$=–5.4

(c=1.3, CHCl₃); ¹H NMR (CDCl₃, 500 MHz) δ 0.99 (t, 3H, J=7.4 Hz), 1.02 (t, 3H, J=7.5 Hz), 1.25 (s, 3H), 1.40 (m, 1H), 1.52 (m, 1H), 1.66 (m, 2H), 2.08 (br s, 1H), 2.98 (t, 1H, J=6.4 Hz), and 3.56 (dd, 1H, J=8.1, 3.0 Hz) ppm; ¹³C{¹H} NMR (CDCl₃, 125 MHz) δ 9.9, 10.4, 14.4, 21.5, 25.6, 60.3, 62.7, and 73.6 ppm; IR (neat) 3443, 2967, 2926, 2877, 2852, 2349, 1722, 1641, 1462, 1380, 1333, 1304, 1259, 1110, 1070, and 1057 cm⁻¹; HRMS-CI m/z 128.1206, [M⁺; calcd for C₈H₁₆O: 128.1201].

Example 39

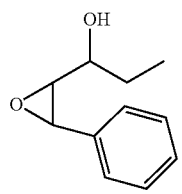

Preparation of threo-1-(3-Phenyl-oxiranyl)-propan-1-ol

The product was prepared by General procedure N using 0.38 mL (0.75 mmol, 2.0 M in hexanes) Et₂Zn, 2.4 mg (0.01 mmol) (−)-MIB, 32 μL (0.25 mmol) cis-cinnamaldehyde, and 50 μL (0.05 mmol, 1.0 M in dichloromethane) Ti(OiPr)₄. The crude product was purified by column chromatography on silica (10% ethyl acetate in hexanes) to afford the title compound as a colorless oil in 96% yield (43 mg, 0.24 mmol). [α]$_D^{20}$=−8.3 (c=2.0, CHCl₃); ¹H NMR (CDCl₃, 500 MHz δ 1.06 (t, 3H, J=7.4 Hz), 1.63 (m, 1H), 1.73 (m, 1H), 1.97 (br s, 1H), 3.09 (br s, 1H), 3.93 (br m, 1H), 3.98 (br s, 1H), and 7.27-7.38 (m, 5H) ppm; ¹³C {¹H} NMR (CDCl₃, 125 MHz) δ 9.5, 26.3, 54.6, 64.7, 69.6, 125.7, 128.2, 128.5 and 137.0 ppm; IR (neat) 3400, 3074, 3027, 2962, 2925, 2854, 2346, 1719, 1654, 1605, 1498, 1463, 1378, 1314, 1267, 1243, and 1141 cm⁻¹; HRMS-CI m/z 161.0973 [(M−OH)⁺; calcd for C₁₁H₁₃O: 161.0966].

Example 40

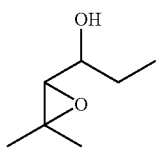

Preparation of threo-1-(3,3-Dimethyl-oxiranyl)-propan-1-ol

The product was prepared by General procedure N using 0.5 mL (1.0 mmol, 2.0 M in hexanes) Et₂Zn, 5.0 mg (0.02 mmol) (−)-MIB, 48 μL (0.5 mmol) 3-methylbut-2-en-al, and 0.05 mL (0.05 mmol, 1.0 M in hexanes) Ti(OiPr)₄. The crude product was purified by column chromatography on silica (20% ethyl acetate in hexanes) to afford the title compound as a colorless oil in 95% yield (61.8 mg, 0.47 mmol): [α]$_D^{20}$=−8.0 (c=0.002, CHCl₃); ¹H NMR (CDCl₃, 500 MHz) δ 0.95 (t, 3H, J=7.0 Hz), 1.51-1.54 (m, 1H), 1.61-1.65 (m, 1H), 2.1 (s, 1H), 2.67 (d, 1H, J=4.5 Hz), and 3.39-3.42 (q, 1H J=7.0 Hz) ppm; ¹³C{¹H} NMR (CDCl₃, 125 MHz): δ 9.3, 19.4, 24.9, 27.0, 59.7, 67.6, and 71.6 ppm; IR (neat) 3362.8, 2938.4, 2894.0, 2806.6, 1727.2, 1453.8, 1381.2, and 1258.5 cm⁻¹. HRMS-CI m/z 131.1069 [(M+H)⁺; calcd for C₇H₁₅O₂: 131.1072].

Example 41

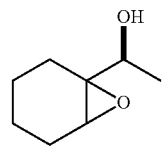

General Procedure O

Preparation of erythro-1-(7-Oxa-bicyclo[4.1.0]hept-1-yl)-ethanol

A 10 mL Schlenk flask was charged with bis(sulfonamide) ligand 2 (3.8 mg, 0.01 mmol), Ti(OtBu)₄ (97 μL, 0.25 mmol), and 0.5 mL hexanes and stirred for 30 min at room temp. A hexanes solution of Me₂Zn (0.25 mL, 0.50 mmol) was then added, and after stirring for 10 min, cyclohexenecarboxaldehyde (14 μL, 0.13 mmol) was added. The reaction was stirred at room temp for 20 h, until alkyl addition was complete by TLC, then cooled to 0° C. 1 equiv Et₂Zn (63 μL, 0.13 mmol) was added; the reaction flask was capped with a balloon of oxygen, warmed to room temperature and allowed to stir under an O₂ atmosphere for 19 h. It was then quenched with 15% tartaric acid solution, allowed to stir for 45 min, then poured into a separatory funnel with a solution of Na₂S₂O₄. The organic and aqueous layers were separated, and the aqueous layer was extracted with hexanes. The combined organic layers were then washed with brine and H₂O and dried over MgSO₄. The filtrate was concentrated in vacuo, and the residue was chromatographed on silica (10% ethyl acetate in hexanes) to afford the title compound as a colorless oil in 78% yield (14 mg, 0.099 mmol). ¹H NMR (CDCl₃, 500 MHz) δ 1.17 (d, 3H J=6.3 Hz), 1.23 (m, 2H), 1.38-1.47 (m, 2H), 1.74 (m, 4H), 2.25 (br s, 1H), 3.18 (m, 1H), and 3.66 (q, 1H J=6.2 Hz) ppm; ¹³C{¹H} NMR (CDCl₃, 125 MHz): δ 18.3, 19.7, 20.3, 24.5, 24.8, 55.2, 63.0, and 67.9 ppm; ¹H NMR and ¹³C NMR spectra for this compound compare with previously reported literature data.

Example 42

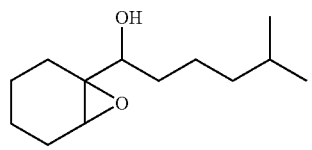

Preparation of erythro-5-Methyl-1-(7-oxa-bicyclo [4.1.0]hept-1-yl)-hexan-1-ol

The product was prepared by General procedure N using 1.0 mL (1.0 mmol, 1.0 M in hexanes) dialkylzinc, 5.0 mg (0.02 mmol) (–)-MIB, 55 mg (0.5 mmol) cyclohexenecarboxaldehyde, and 0.05 mL (0.05 mmol, 1.0 M in hexanes) Ti(OiPr)$_4$. The crude product was purified by column chromatography on silica (20% ethyl acetate in hexanes) to afford the title compound as a colorless oil in 62% yield (65.8 mg, 0.31 mmol): $[\alpha]_D^{20}$=–7.25 (c=0.024, CHCl$_3$, 97% ee); $^1$H NMR (CDCl$_3$, 500 MHz) δ 3.54 (d, 1H J=5.0 Hz), 3.19 (s, 1H), 2.1-2.0 (m, 2H), 1.80-1.72 (m, 2H), 1.61.5 (m, 4H), 1.45-1.30 (m, 2H), 1.30-1.25 (m, 2H), and 0.87 (d, 6H, J=6.5 Hz) and ppm; $^{13}$C{$^1$H} NMR (CDCl$_3$, 125 MHz): δ 71.75, 62.44, 55.40, 39.06, 33.09, 27.91, 25.14, 24.47, 23.57, 22.61, 22.52, 20.36, and 19.70 ppm; IR (neat) 3490.2, 2960.0, 2931.2, 2861.1, 2358.1, 2341.2, 1728.6, 1633.5, 1600.3, 1580.7, 1462.7, 1383.4, and 1261.2 cm$^{-1}$. HRMS-CI m/z 213.1864 [(M–H)$^+$; calcd for C$_{13}$H$_{25}$O$_2$: 213.1855].

Example 43

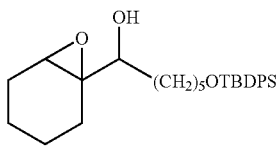

Preparation of erythro-6-(tert-Butyl-diphenyl-silanyloxy)-1-(7-oxa-bicyclo[4.1.0]hept-1-yl)-hexan-1-ol The product was prepared by General procedure N using 1.5 mL (1.5 mmol, 1.0 M in hexanes) dialkylzinc, 4.8 mg (0.02 mmol) (–)-MIB, 57 μL (0.5 mmol) cyclohexene carboxaldehyde, and 100 μL (0.10 mmol, 1.0 M in hexanes) Ti(OiPr)$_4$. The crude product was purified by column chromatography on silica (10% ethyl acetate in hexanes) to afford the title compound as a colorless oil in 86% yield (194 mg, 0.43 mmol). $[\alpha]_D^{20}$=–87.3 (c=0.74, CHCl$_3$); $^1$H NMR (CDCl$_3$, 500 MHz) δ 0.98 (s, 9H), 1.12 (m, 2H), 1.32 (m, 4H), 1.43 (m, 2H), 1.52 (m, 4H), 1.68 (m, 2H), 1.91 (dt, 2H, J=15.3, 5.6 Hz), 2.03 (br s, 1H), 3.12 (br s, 1H), 3.46 (br m, 1H), 3.59 (t, 2H, J=6.4 Hz), 7.31 (m, 6H), and 7.59 (d, 4H, J=6.6 Hz) ppm; $^{13}$C{$^1$H} NMR (CDCl$_3$, 125 MHz) δ 19.2, 19.7, 20.3, 24.5, 25.1, 25.6, 25.9, 26.9, 32.5, 32.8, 55.4, 62.2, 63.9, 71.7, 127.6, 129.5, 134.2, and 135.6 ppm; IR (neat) 3457, 3070, 3048, 2932, 2857, 1731, 1589, 1461, 1428, 1389, 1361, 1261, 1187, 1111, 1029, and 1007 cm$^{-1}$; HRMS-ESI m/z 475.2630 [(M–Na)$^+$; calcd for C$_{28}$H$_{40}$O$_3$NaSi: 475.2644].

Example 44

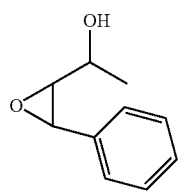

Preparation of threo-1-(3-Phenyl-oxiranyl)-ethanol

The product was prepared by General procedure O using 4.5 mg (0.012 mmol) ligand 2, 0.30 mL (0.6 mmol, 2.0 M in hexanes) Me$_2$Zn, 116 μL (0.30 mmol) Ti(OtBu)$_4$, 19 μL (0.15 mmol) cis-cinnamaldehyde, and 75 μL (0.15 mmol, 2.0 M in hexanes) Et$_2$Zn. The crude product was purified by column chromatography on silica (10% ethyl acetate in hexanes) to afford the title compound as a colorless oil in 89% yield (22.3 mg, 0.14 mmol). $^1$H NMR (CDCl$_3$, 500 MHz) δ 1.01 (d, 3H, J=6.4 Hz), 3.15 (dd, 1H, J=8.4, 4.4 Hz), 3.28 (dq, 1H, J=8.1, 6.4 Hz), and 4.18 (d, 1H, J=4.3 Hz) ppm; $^{13}$C{$^1$H} NMR (CDCl$_3$, 125 MHz) δ 18.3, 57.5, 63.2, 66.2, 126.0, 127.8, 128.3, and 134.7 ppm; $^1$H NMR and $^{13}$C NMR spectra for this compound compare with previously reported literature data.

Example 45

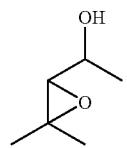

Preparation of threo-1-(3,3-Dimethyl-oxiranyl)-ethanol

The product was prepared by General procedure O using 7.6 mg (0.02 mmol) ligand 2, 0.50 mL (1.0 mmol, 2.0 M in hexanes) Me$_2$Zn, 193 μL (0.50 mmol) Ti(OtBu)$_4$, 21 μL (0.25 mmol) 3-methylbut-2-en-al, and 125 μL (0.25 mmol, 2.0 M in hexanes) Et$_2$Zn. The crude product was purified by column chromatography on silica (10% ethyl acetate in hexanes) to afford the title compound as a colorless oil in 60% yield (17.5 mg, 0.15 mmol). $^1$H NMR (CDCl$_3$, 500 MHz) δ 1.24 (d, 3H, J=6.0 Hz), 1.29 (s, 3H), 1.32 (s, 3H), 2.69 (d, 1H, J=7.9 Hz), and 3.64 (dq, 1H, J=7.1, 5.7 Hz) ppm; $^{13}$C{$^1$H} NMR (CDCl$_3$, 125 MHz) δ 18.99, 19.01, 24.9, 60.1, 67.3, and 68.8 ppm; $^1$H NMR and $^{13}$C NMR spectra for this compound compare with previously reported literature data.

Example 46

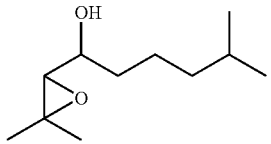

Preparation of threo-1-(3,3-Dimethyl-oxiranyl)-5-methyl-hexan-1-ol

The product was prepared by General procedure N using 0.5 mL (1.0 mmol, 2.0 M in hexanes) Et$_2$Zn, 5.0 mg (0.02 mmol) (–)-MIB, 48 μL (0.5 mmol) 3-methylbut-2-en-al, and 0.05 mL (0.05 mmol, 1.0 M in hexanes) Ti(OiPr)$_4$. The crude product was purified by column chromatography on silica (20% ethyl acetate in hexanes) to afford the title compound as a colorless oil in 81% yield (75.33 mg, 0.41 mmol): $[\alpha]_D^{20}$=–4.77 (c=0.013, CHCl$_3$, 96% ee); $^1$H NMR (CDCl$_3$, 500 MHz) δ 3.46 (q, 1H J=5.0 Hz), 2.68 (d, 1H, J=8.0 Hz), 1.94 (OH, s, 1H), 1.66-1.52 (m, 4H), 1.47-1.42 (m, 1H), 1.31 (d, 6H J=9.5 Hz), 1.24-1.18 (m, 2H) and 0.88 (d, 6H, J=6.5 Hz) ppm;

$^{13}C\{^1H\}$ NMR (CDCl$_3$, 125 MHz): δ 70.40, 67.78, 63.26, 38.91, 34.26, 27.88, 24.90, 22.75, 22.55, and 19.41 ppm; IR (neat) 3409.9, 2992.1, 2961.3, 2274.0, 1662.0, 1588.3, 1548.2, 1529.0, 1480.5, 1260.1, and 1098.6 cm$^{-1}$; HRMS-CI m/z 187.1695 [(M+H)$^+$; calcd for C$_{11}$H$_{23}$O$_2$: 187.1698].

Substrates and Products From Table 5

Example 47

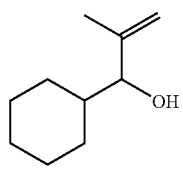

General Procedure P

Preparation of (S)-2-Methyl-3-cyclohexyl-propen-3-ol

Into a 20-mL scintal vial 46.5 mg (0.41 mmol) cyclohexanecarboxaldehyde was added dropwise (neat) and diluted with 1.5 mL toluene in a nitrogen atmosphere glovebox. A dry and thoroughly purged (N$_2$) 10 mL Schlenk flask capped with a rubber septum was charged with 4.0 mg (0.017 mmol) (−)-MIB and a stir bar. In the glovebox, 65.5 mg (0.44 mmol) 3 was weighed into the Schlenk flask and the solids diluted with toluene (2 mL). 3.1 eq. (125 μL, 1.23 mmol) Et$_2$Zn was then added neat. The flask was cooled to 0° C. and the aldehyde was added dropwise under an N$_2$ purge. The reaction was stirred until judged complete by TLC and then quenched with saturated NH$_4$Cl (6 mL). The clear biphasic layers were partitioned and the aqueous layer was repeatedly extracted with diethyl ether (3×25 mL). The combined organic layer was washed with brine, dried over MgSO$_4$ and concentrated. The crude product was purified by column chromatography on silica (70:20:10, hexanes:CH$_2$Cl$_2$:EtOAc) to afford the title compound as a colorless oil in 90% yield (58 mg, 0.37 mmol). $[\alpha]_D^{20}$=−16.7 (c=0.104, CHCl$_3$, 92% ee). $^1$H NMR (C$_6$D$_6$, 500 MHz): δ 0.88-0.98 (m, 2H; methylene), 1.09-1.17 (m, 3H; methylene), 1.18 (br, 1H; OH), 1.35 (m, 1H; methylene), 1.46 (m, 1H; methylene), 1.58 (m, 1H; methylene), 1.59 (s, 3H; CH$_3$), 1.64 (m, 1H; methylene), 1.71 (m, 1H; methylene), 2.01 (m, 1H; methylene), 3.54 (d, 4 Hz, 1H; RCHOH), 4.78 (s, 1H; alkene), 4.84 (s, 1H; alkene) ppm. $^{13}C\{^1H\}$ NMR (C$_6$D$_6$, 125 MHz): δ 17.88, 26.81, 26.98, 27.25, 29.02, 30.39, 41.25, 81.16, 112.26, 147.48 ppm. IR (neat): 3383 (OH), 2919, 2848, 1648, 1446, 1372, 1260, 1080, 1019 cm$^{-1}$. LRMS-CI m/z 136.13 [(M−☐☐)$^+$; calcd for; C$_{10}$H$_{17}$: 136.13].

Example 48

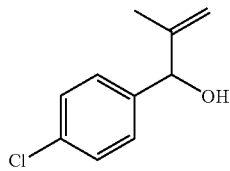

Preparation of (S)-2-Methyl-3-p-tolyl-propen-3-ol

The product was prepared by General procedure P using 73.4 mg (0.50 mmol) 3, 80 μL (0.76 mmol, neat) Et$_2$Zn, 2.5 mg (0.010 mmol) (−)-MIB, and 30.3 mg (0.25 mmol) p-tolualdehyde. The crude product was purified by column chromatography on silica (70:20:10, hexanes:CH$_2$Cl$_2$:EtOAc) to afford the title compound as a colorless oil in 85% yield (34.7 mg, 0.21 mmol). $[\alpha]_D^{20}$=−12.1 (c=0.131, CHCl$_3$, 96% ee). $^1$H NMR (C$_6$D$_6$, 300 MHz): δ 1.52 (s, 3H; CH$_3$), 1.55 (s, 1H; OH), 2.10 (s, 3H; ArCH$_3$), 4.84 (t, 1.5 Hz, 1H; alkene), 4.86 (s, 1H; RCHOH), 5.18 (t, 1.5 Hz, 1H; alkene), 6.98 (d, 8 Hz, 2H; Ar), 7.24 (d, 8 Hz, 2H; Ar) ppm. $^{13}C\{^1H\}$ NMR (C$_6$D$_6$, 75.5 MHz): δ 18.54, 21.43, 78.12, 111.29, 127.16, 129.54, 137.35, 140.41, 147.98 ppm. IR (neat): 3420 (OH), 2923, 2854, 1722, 1656, 1513, 1450, 1260, 1177, 1046, 1020 cm$^{-1}$. HRMS-CI m/z 149.0963 [(M−)$^+$; calcd for C$_{10}$H$_{17}$: 136.13].

Example 49

Preparation of (S)-2-Methyl-3-p-chloro-phenyl-propen-3-ol

The product was prepared by General procedure P using 72.3 mg (0.49 mmol) 3, 75 μL (0.72 mmol, neat) Et$_2$Zn, 2.3 mg (0.01 mmol) (−)-MIB, and 37.5 mg (0.24 mmol) p-chlorobenzaldehyde (Aldrich, 90%). The crude product was purified by column chromatography on silica (70:20:10, hexanes:CH$_2$Cl$_2$:EtOAc) to afford the title compound as a colorless oil in 88% yield (38.6 mg, 0.21 mmol). $[\alpha]_D^{20}$=−9.4 (c=0.101, CHCl$_3$, 97% ee). $^1$H NMR (C$_6$D$_6$, 300 MHz): δ 1.30 (S, 1H; OH), 1.39 (s, 3H; CH$_3$), 4.65 (s, 1H; RCHOH), 4.75 (s, 1H; alkene), 5.00 (s, 1H; alkene), 7.01 (d, 8.5 Hz, 2H; Ar), 7.09 (d, 8.5 Hz, 2H; Ar) ppm. $^{13}C\{^1H\}$ NMR (C$_6$D$_6$, 75.5 MHz): δ 18.03, 77.48, 111.98, 128.43, 128.93, 133.70, 141.58, 147.32 ppm. IR (neat): 3372 (OH), 2974, 2918, 2856, 1903, 1651, 1596, 1488, 1450, 1408, 1373, 1230, 1188, 1091 cm$^{-1}$. HRMS-CI m/z 182.0495 [M$^+$; calcd for C$_{10}$H$_{11}$OCl: 182.0498].

Example 50

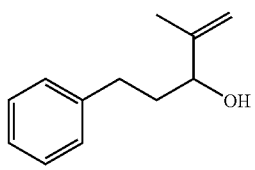

Preparation of (S)-2-Methyl-3-hydrocinnamyl-propen-3-ol

The product was prepared by General procedure P using 49.5 mg (0.34 mmol) 3, 100 μL (0.98 mmol, neat) Et$_2$Zn, 3.1 mg (0.013 mmol) (–)-MIB, and 43.6 mg (0.33 mmol) hydrocinnamaldehyde. The crude product was purified by column chromatography on silica (70:20:10, hexanes:CH$_2$Cl$_2$:EtOAc) to afford the title compound as a colorless oil in 89% yield (51.0 mg, 0.29 mmol). [α]$_D^{20}$=–3.4 (c=0.07, CHCl$_3$, 90% ee). $^1$H NMR (C$_6$D$_6$, 500 MHz): δ 1.01 (s, 1H; OH), 1.55 (t, 1.5 Hz, 3H; CH$_3$), 1.72 (m, 2H; methylene), 2.56 (m, 1H; methylene), 2.65 (m, 1H; methylene), 3.79 (m, 1H; RCHOH), 4.73 (m, 1H; alkene), 4.87 (m, 1H; alkene), 7.06 (t, 7 Hz, 1H; Ph), 7.08 (d, 7.5 Hz, 2H; Ph), 7.14 (d, 8.5 Hz, 2H; Ph) ppm. $^{13}$C{$^1$H} NMR (C$_6$D$_6$, 75.5 MHz): δ 18.04, 32.59, 37.52, 75.29, 111.08, 126.44, 129.02, 129.17, 142.86, 148.43 ppm. IR and mass data were in agreement with the literature values.

Example 51

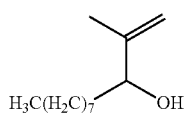

Preparation of (S)-2-Methyl-3-octyl-propen-3-ol

The product was prepared by General procedure P using 84.9 mg (0.58 mmol) 3, 90 μL (0.88 mmol, neat) Et$_2$Zn, 2.8 mg (0.012 mmol) (–)-MIB, and 41.0 mg (0.29 mmol) nonyl aldehyde. The crude product was purified by column chromatography on silica (70:20:10, hexanes:CH$_2$Cl$_2$:EtOAc) to afford the title compound as a colorless oil in 83% yield (44.0 mg, 0.24 mmol). [α]$_D^{20}$=–25.2 (c 0.06, CHCl$_3$, 87% ee). $^1$H NMR (C$_6$D$_6$, 500 MHz): δ 0.89 (t, 6.5 Hz, 3H; CH$_3$), 1.25 (m, 12H; methylene), 1.35 (s, 1H; OH), 1.48 (m, 2H; methylene), 1.63 (s, 3H; CH$_3$), 3.87 (t, 6 Hz, 1H; RCHOH), 4.76 (s, 1H; alkene), 4.92 (s, 1H; alkene) ppm. $^{13}$C{$^1$H} NMR (C$_6$D$_6$, 125.5 MHz): δ 14.70, 17.98, 23.44, 26.43, 30.10, 30.40, 32.65, 35.88, 76.26, 110.90, 148.79 ppm. IR (neat): 3355 (OH), 2926, 1712, 1649, 1458, 1376, 1302, 1260, 1116, 1066, 1026 cm$^{-1}$. HRMS-CI m/z 184.1830 [M$^+$; calcd for C$_{12}$H$_{24}$O: 184.1827].

Example 52

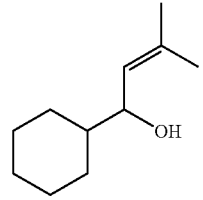

Preparation of (S)-1-Methyl-4-cyclohexyl-buten-4-ol

The product was prepared by General procedure P using 89.5 mg (0.51 mmol) 4, 115 μL (1.13 mmol, neat) Et$_2$Zn, 3.5 mg (0.015 mmol) (–)-MIB, and 40.8 mg (0.36 mmol) cyclohexanecarboxaldehyde. The crude product was purified by column chromatography on silica (70:20:10, hexanes:CH$_2$Cl$_2$:EtOAc) to afford the title compound as a colorless oil in 75% yield (45.8 mg, 0.27 mmol). [α]$_D^{20}$=–8.6 (c=0.06, CHCl$_3$, 90% ee). $^1$H NMR (C$_6$D$_6$, 300 MHz): δ 0.90-1.16 (m, 4H; methylene), 1.19 (s, 1H; OH), 1.21 (m, 1H; methylene), 1.34 (m, 1H; methylene), 1.49 (d, 1.2 Hz, 3H; C[CH$_3$][CH$_3$]), 1.59 (d, 1.2 Hz, 3H; C[CH$_3$][CH$_3$]), 1.68 (m, 4H; methylene), 2.04 (br dd, 14, 1.8 Hz, 1H; methylene), 3.98 (dd, 9, 1.8 Hz, 1H; RCHOH), 5.16 (dt, 9, 1.2 Hz, 1H; alkene) ppm. $^{13}$C{$^1$H} NMR (C$_6$D$_6$, 75 MHz): δ 18.68, 26.25, 26.89, 27.02, 27.42, 29.41, 29.67, 45.17, 73.18, 128.71, 134.45 ppm. IR (neat): 3354 (OH), 2919, 2849, 1678, 1449, 1378 1296, 1190, 1079, 1002 cm$^{-1}$. HRMS-CI m/z 151.1483 [(M–OH)$^+$; calcd for C$_{11}$H$_{19}$: 151.1487].

Example 53

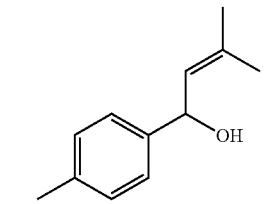

Preparation of (S)-1-Methyl-4-p-tolyl-buten-4-ol

The product was prepared by General procedure P using 81.2 mg (0.46 mmol) 4, 150 μL (1.48 mmol, neat) Et$_2$Zn, 4.5 mg (0.019 mmol) (–)-MIB, and 55.5 mg (0.46 mmol) p-tolualdehyde. The crude product was purified by column chromatography on silica (70:20:10, hexanes:CH$_2$Cl$_2$:EtOAc) to afford the title compound as a colorless oil in 81% yield (66.0 mg, 0.37 mmol). [α]$_D^{20}$=–21.4 (c=0.10, CHCl$_3$, 95% ee). $^1$H NMR (C$_6$D$_6$, 300 MHz): δ 1.29 (s, 1H; OH), 1.52 (s, 6H; C[CH$_3$]$_2$), 2.12 (s, 3H; ArCH$_3$), 5.31 (d, 8.5 Hz, 1H; RCHOH), 5.42 (dt, 8.5, 1.5 Hz, 1H; alkene), 7.03 (d, 8 Hz, 2H; Ar), 7.33 (d, 8 Hz, 2H; Ar) ppm. $^{13}$C{$^1$H} NMR (C$_6$D$_6$, 75.5 MHz): δ 18.46, 21.44, 26.05, 70.98, 126.63, 129.62, 129.84, 133.89, 136.91, 142.77 ppm. IR (neat): 3354 (OH), 2978, 2919, 2367, 2331, 1672, 1514, 1443, 1373, 1243, 1179, 1108, 1038, 1008 cm$^{-1}$. HRMS-CI m/z 158.1088 [(M–H$_2$O)$^+$; calcd for C$_8$H$_{14}$: 158.1096].

Example 54

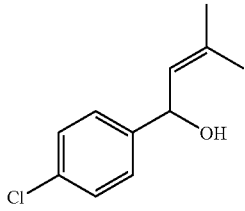

Preparation of (S)-1-Methyl-4-p-chloro-phenyl-buten-4-ol

The product was prepared by General procedure P using 72.3 mg (0.41 mmol) 4, 130 µL (1.27 mmol, neat) Et$_2$Zn, 4.9 mg (0.020 mmol) (–)-MIB, and 57.9 mg (0.41 mmol) p-chlorobenzaldehyde. The crude product was purified by column chromatography on silica (70:20:10, hexanes:CH$_2$Cl$_2$:EtOAc) to afford the title compound as a white solid in 83% yield (67.3 mg, 0.34 mmol). [α]$_D^{20}$=–6.5 (c=0.09, CHCl$_3$, 96% ee). 1H NMR (C$_6$D$_6$, 500 MHz): δ 1.19 (br s, 1H; OH), 1.44 (d, 1.5 Hz, 3H; C[CH3] [CH3]), 1.48 (d, 1.5 Hz, 3H; C[CH3] [CH3]), 5.11 (d, 8.5 Hz, 1H; RCHOH), 5.19 (dt, 8.5, 1.5 Hz, 1H; alkene), 7.09 (d, 8 Hz, 2H; Ar), 7.14 (d, 8.5 Hz, 2H; Ar) ppm. $^{13}$C{$^1$H} NMR (C$_6$D$_6$, 125 MHz): δ 18.40, 25.97, 70.26, 127.98, 128.30, 129.02, 133.32, 134.75, 143.96 ppm. IR (neat): 3354 (OH), 2966, 2931, 1672, 1596, 1489, 1446, 1402, 1378, 1261, 1196, 1090, 1014 cm$^{-1}$. HRMS-CI m/z 196.0655 [M$^+$; calcd for C$_{11}$H$_{13}$OCl: 196.0658].

Example 55

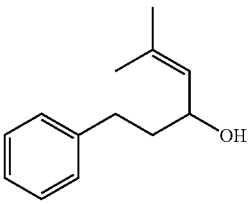

Preparation of (S)-1-Methyl-4-hydrocinnamyl-buten-4-ol

The product was prepared by General procedure P using 65.1 mg (0.35 mmol) 4, 85 µL (0.82 mmol, neat) Et$_2$Zn, 2.5 mg (0.011 mmol) (–)-MIB, and 35.6 mg (0.27 mmol) hydrocinnamaldehyde. The crude product was purified by column chromatography on silica (70:20:10, hexanes:CH$_2$Cl$_2$:EtOAc) to afford the title compound as a colorless oil in 85% yield (42.8 mg, 0.22 mmol). [α]$_D^{20}$=–28.3 (c=0.05, CHCl$_3$, 80% ee). $^1$H NMR (C$_6$D$_6$, 500 MHz): δ 1.14 (s, 1H; OH), 1.42 (s, 3H; C[CH$_3$] [CH$_3$]), 1.56 (s, 3H; C[CH$_3$] [CH$_3$]), 1.71 (m, 1H; methylene), 1.89 (m, 1H; methylene), 2.66 (m, 2H; methylene), 4.23 (q, 8 Hz, 1H; RCHOH), 5.17 (dt, 8.5, 1.5 Hz, 1H; alkene), 7.07 (t, 7 Hz, 1H; Ph), 7.12 (d, 8 Hz, 2H; Ph), 7.17 (d, 8 Hz, 2H; Ph) ppm. $^{13}$C{$^1$H} NMR (C$_6$D$_6$, 75.5 MHz): δ 18.44, 26.07, 32.56, 40.15, 68.17, 126.38, 128.99, 129.16, 129.71, 134.34, 142.98 ppm. IR (neat): 3378 (OH), 2966, 2931, 2861, 2356, 1678, 1602, 1496, 1454, 1378, 1290, 1267, 1114, 1043, 1008 cm$^{-1}$. HRMS-CI m/z 172.1254 [(M–H$_2$O)$^+$; calcd for C$_{13}$H$_{16}$Cl: 172.1252].

Example 56

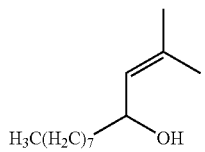

Preparation of (S)-1-Methyl-4-octyl-buten-4-ol

The product was prepared by General procedure P using 62.0 mg (0.35 mmol) 4, 110 µL (1.06 mmol, neat) Et$_2$Zn, 3.4 mg (0.014 mmol) (–)-MIB, and 50.1 mg (0.35 mmol) nonyl aldehyde. The crude product was purified by column chromatography on silica (70:20:10, hexanes:CH$_2$Cl$_2$:EtOAc) to afford the title compound as a colorless oil in 78% yield (54.4 mg, 0.27 mmol). [α]$_D^{20}$=–22.5 (c=0.75, CHCl$_3$, 85% ee). $^1$H NMR (C$_6$D$_6$, 300 MHz): δ 0.89 (t, 6.5 Hz, 3H; CH$_3$), 1.08 (br S, 1H; OH), 1.26 (br, 10H; methylene), 1.42 (q, 6.5 Hz, 2H; methylene), 1.50 (d, 1.5 Hz, 3H; C[CH$_3$] [CH$_3$]), 1.58 (d, 1.5 Hz, 3H; C[CH$_3$] [CH$_3$]), 1.64 (m, 2H; methylene), 4.27 (q, 9 Hz, 1H; RCHOH), 5.19 (dt, 9, 1.5 Hz, 1H; alkene) ppm. $^{13}$C{$^1$H} NMR (C$_6$D$_6$, 75.5 MHz): δ 14.70, 18.49, 23.44, 26.13, 26.34, 30.11, 30.46, 30.53, 32.65, 38.72, 68.96, 130.24, 133.88 ppm. IR (neat): 3360 (OH), 2925, 2855, 2360, 1456, 1375, 1292, 1062 cm$^{-1}$. HRMS-CI m/z 180.1878 [(M–H$_2$O)$^+$; calcd for C$_{13}$H$_{24}$: 180.1876].

Example 57

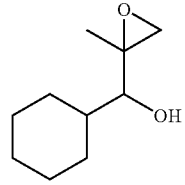

General Procedure Q

Preparation of erythro-(S)-1-(2-Methyl-1-oxiranyl-3-cyclohexyl)-propan-3-ol

Into a 20-mL scintal vial 94.1 mg (0.41 mmol) cyclohexanecarboxaldehyde was added dropwise (neat) and diluted with 1.5 mL toluene in a nitrogen atmosphere glovebox. A dry and thoroughly purged (N$_2$) 10 mL Schlenk flask capped with a rubber septum was charged with 8.0 mg (0.034 mmol) (–)-MIB and a stir bar. In the glovebox, 123.8 mg (0.84 mmol) 3 was weighed into the Schlenk flask and the solids diluted with toluene (2 mL). 3.1 eq. (275 µL, 2.68 mmol) Et$_2$Zn was then added neat. The flask was cooled to 0° C. and the aldehyde was added dropwise under an N₂ purge. The reaction was stirred until the vinylation was complete, then the solution was cooled to −20° C., purged with N₂, and saturated with 1 atm of O₂ for 30 min. 47.7 mg (0.20 mmol) Ti(OiPr)₄ (2 M toluene solution) was added under an N₂ purge dropwise, followed by resaturation of the solution with the O₂ balloon. The reaction was warmed to 0° C. after stirring at −20° C. for 12 hr. The epoxidation reaction was stirred until judged complete by TLC, then quenched with saturated NH₄Cl and Na₂CO₃ (8 mL). The pale yellow biphasic solution and salts were filtered through celite, washed with diethyl ether (2×25 mL), and the aqueous layer was repeatedly extracted with diethyl ether (3×30 mL). The combined organic layer was washed with brine, dried over MgSO₄ and concentrated. The crude product was purified by column chromatography on silica (60:30:10, hexanes:CH₂Cl₂:EtOAc) to afford the title compound as a colorless oil in 90.1% yield (128.7 mg, 0.37 mmol, mixture of diastereomers). [α]$_D^{20}$=−14.2 (c=0.20, CHCl₃). ¹H NMR (C₆D₆, 300 MHz): δ 1.01 (s, 3H; CH₃), 1.08-1.34 (m, 6H; methylene), 1.54 (m, 4H; methylene), 1.67 (d, 1.5 Hz, 1H; OH), 1.70 (m, 1H; methylene), 2.16 (d, 5 Hz, 1H; epoxide), 2.61 (d, 5 Hz, 1H; epoxide), 3.22 (dd, 4.5, 1.5 Hz, 1H, RCHOH) ppm. ¹³C{¹H} NMR (C₆D₆, 125 MHz): δ 18.57, 26.98, 27.08, 27.12, 27.29, 30.82, 30.95, 57.95, 66.25, 76.12 ppm. IR (neat): 3468 (OH), 2927, 2852, 2361, 1450, 1389, 1370, 1258, 1112, 1027 cm⁻¹. HRMS-CI m/z 170.1310 [M⁺; calcd for C₁₀H₁₉O₂: 170.1307].

Example 58

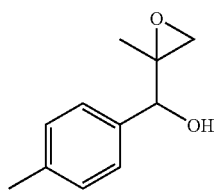

General Procedure R

Preparation of erythro-(S)-1-(2-Methyl-1-oxiranyl-3-p-tolyl)-propan-3-ol

The product was prepared as in General procedure Q using 92.8 mg (0.63 mmol) 3, 205 μL (2.01 mmol, neat) Et₂Zn, 6.0 mg (0.025 mmol) (−)-MIB, 75.5 mg (0.25 mmol) p-tolualdehyde, and 35.9 mg (0.13 mmol) Ti(OiPr)₄; however, the Ti(OiPr)₄ solution (2 mL in toluene) was added to the completed vinylation reaction at 0° C. The reaction was then stirred at 0° C. for 36 hrs, warmed to 25° C. for 12 hr, and quenched as stated in procedure F. The crude product was purified by column chromatography on silica (60:30:10, hexanes:CH₂Cl₂:EtOAc) to afford the title compound as a colorless oil in 85% yield (95.1 mg, 0.53 mmol, mixture of diastereomers). [α]$_D^{20}$=−34.4 (c=0.23, CHCl₃). ¹H NMR (C₆D₆, 500 MHz): δ 1.00 (s, 3H; CH₃), 2.10 (s, 3H; ArCH₃), 2.15 (d, 5 Hz, 1H; epoxide), 2.22 (s, 1H; OH), 2.79 (d, 5 Hz, 1H; epoxide), 4.39 (s, 1H; RCHOH), 6.98 (d, 8 Hz, 2H; Ar), 7.21 (d, 8 Hz, 2H; Ar) ppm. ¹³C{¹H} NMR (C₆D₆, 125 MHz): δ 18.22, 21.44, 50.45, 59.98, 75.19, 127.78, 129.52, 137.93, 138.27 ppm. IR (neat): 3430 (OH), 2979, 2922, 2869, 1513, 1389, 1365, 1235, 1192, 1178, 1056, 1022 cm⁻¹. HRMS-CI m/z 119.1069 [(M+H)⁺; calcd for C₁₁H₁₅O₂: 179.1072].

Example 59

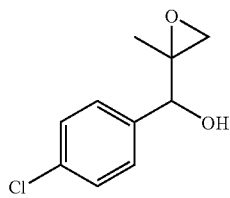

Preparation of erythro-(S)-1-(2-Methyl-1-oxiranyl-3-p-chloro-phenyl)-propan-3-ol The product was prepared by General procedure R using 100.1 mg (0.68 mmol) 3, 225 μL (2.18 mmol, neat) Et₂Zn, 6.5 mg (0.027 mmol) (−)-MIB, 95.4 mg (0.68 mmol) p-chlorobenzaldehyde, and 38.6 mg (0.14 mmol) Ti(OiPr)₄. The crude product was purified by column chromatography on silica (60:30:10, hexanes:CH₂Cl₂:EtOAc) to afford the title compound as a colorless oil in 84.5% yield (114.0 mg, 0.57 mmol, mixture of diastereomers). [α]$_D^{20}$=−15.6 (c=0.17, CHCl₃). ¹H NMR (C₆D₆, 300 MHz): δ 0.87 (s, 3H; CH₃), 1.96 (d, 1.5 Hz, 1H; OH), 2.06 (d, 5 Hz, 1H; epoxide), 2.57 (d, 5 Hz, 1H; epoxide), 4.16 (d, 1.5 Hz, 1H; RCHOH), 6.96 (d, 8 Hz, 2H; Ar), 7.08 (d, 8 Hz, 2H; Ar) ppm. ¹³C{¹H} NMR (C₆D₆, 75.5 MHz): δ 17.84, 50.32, 59.57, 74.70, 127.51, 128.98, 129.05, 139.54 ppm. IR (neat): 3441 (OH), 2984, 1485, 1443, 1443, 1391, 1365, 1235, 1193, 1089, 1063, 1017 cm⁻¹. HRMS-CI m/z 198.0453 [M⁺; calcd for C₁₀H₁₁O₂Cl: 198.0448].

Example 60

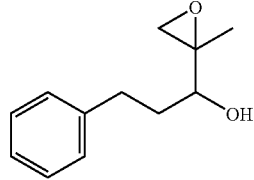

Preparation of erythro-(S)-1-(2-Methyl-1-oxiranyl-3-hydrocinnamyl)-propan-3-ol

The product was prepared by General procedure Q using 106.9 mg (0.72 mmol) 3, 230 μL (2.25 mmol, neat) Et₂Zn, 6.9 mg (0.029 mmol) (−)-MIB, 97.3 mg (0.72 mmol) hydrocinnamaldehyde, and 41.2 mg (0.20 mmol) Ti(OiPr)₄. The crude product was purified by column chromatography on silica (60:30:10, hexanes:CH₂Cl₂:EtOAc) to afford the title compound as a colorless oil in 88.7% yield (123.7 mg, 0.64 mmol, mixture of diastereomers). [α]$_D^{20}$=−18.5 (c=0.15, CHCl₃). ¹H NMR (C₆D₆, 500 MHz): δ 0.94 (s, 3H; CH₃), 1.52 (m, 1H; methylene), 1.69 (m, 1H; methylene), 1.84 (s, 1H; OH), 2.09 (d, 5.5 Hz, 1H; epoxide), 2.55 (d, 5.5 Hz, 1H; epoxide), 2.65 (m, 1H; methylene), 2.84 (m, 1H; methylene), 3.35 (dt, 9, 2 Hz, 1H; RCHOH), 7.05 (t, 7.5 Hz, 1H; Ph), 7.10 (d, 8 Hz, 2H;

Ph), 7.17 (d, 7.5 Hz, 2H; Ph) ppm. $^{13}$C{$^1$H} NMR (C$_6$D$_6$, 75.5 MHz): δ 18.10, 32.58, 35.54, 50.24, 59.04, 71.44, 126.51, 129.04, 129.21, 142.82 ppm. IR (neat): 3456 (OH), 2924, 2863, 2364, 1603, 1560, 1542, 1496, 1453, 1389, 1095, 1064 cm$^{-1}$. HRMS-CI m/z 175.1115 [(M–OH)$^+$; calcd for C$_{12}$H$_{15}$O: 175.1123].

Example 61

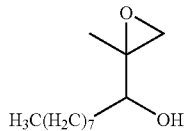

Preparation of erythro-(S)-1-(2-Methyl-1-oxiranyl-3-octyl)-propan-3-ol

The product was prepared by General procedure R using 75.5 mg (0.51 mmol) 3, 170 μL (1.65 mmol, neat) Et$_2$Zn, 4.9 mg (0.021 mmol) (–)-MIB, 72.8 mg (0.51 mmol) nonyl aldehyde, and 29.2 mg (0.102 mmol) Ti(OiPr)$_4$. The crude product was purified by column chromatography on silica (60:30:10, hexanes:CH$_2$Cl$_2$:EtOAc) to afford the title compound as a colorless oil in 84% yield (86.1 mg, 0.43 mmol, mixture of diastereomers). [α]$_D^{20}$=–31.3 (c=0.11, CHCl$_3$). $^1$H NMR (C$_6$D$_6$, 500 MHz): δ 0.90 (t, 7 Hz, 3H; CH$_3$), 1.03 (s, 3H; CH$_3$), 1.24-1.32 (m, 8H; methylene), 1.38-1.47 (m, 4H; methylene), 1.58 (m, 2H; methylene), 1.75 (s, 1H; OH), 2.14 (d, 5 Hz, 1H; epoxide), 2.59 (d, 5 Hz, 1H; epoxide), 3.39 (dt, 8.5, 2 Hz, 1H; RCHOH) ppm. $^{13}$C{$^1$H} NMR (C$_6$D$_6$, 125.5 MHz): δ 14.70, 18.22, 23.43, 26.44, 30.10, 30.36, 30.48, 32.64, 33.70, 50.32, 59.12, 72.35 ppm. IR (neat): 3451 (OH), 2921, 2859, 2356, 1458, 1443, 1396, 1380, 1256, 1069, 1069 cm$^{-1}$. HRMS-CI m/z 182.1675 [M$^+$; calcd for C$_{12}$H$_{22}$O: 182.1671].

Example 62

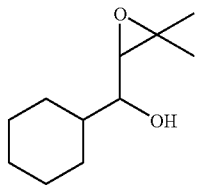

Preparation of threo-(S)-1-(1-Methyl-2-oxiranyl-4-cyclohexyl)-butan-4-ol

The product was prepared by General procedure R using 83.0 mg (0.47 mmol) 4, 155 μL (1.52 mmol, neat) Et$_2$Zn, 4.5 mg (0.019 mmol) (–)-MIB, 53.1 mg (0.47 mmol) cyclohexanecarboxaldehyde, and 27.1 mg (0.095 mmol) Ti(OiPr)$_4$. The crude product was purified by column chromatography on silica (60:30:10, hexanes:CH$_2$Cl$_2$:EtOAc) to afford the title compound as a colorless oil in 79.1% yield (68.9 mg, 0.37 mmol, mixture of diastereomers). [α]$_D^{20}$=–26.9 (c=0.18, CHCl$_3$). $^1$H NMR (CDCl$_3$, 300 MHz): δ 1.00 (m, 2H; methylene), 1.21 (m, 2H; methylene), 1.30 (s, 3H; C[CH$_3$] [CH$_3$]), 1.33 (s, 3H; C[CH$_3$] [CH$_3$]), 1.47 (m, 2H; methylene), 1.71-1.78 (m, 4H; methylene), 1.99 (br, 1H; methylene), 2.03 (br s, 1H; OH), 2.73 (d, 8 Hz, 1H; epoxide), 3.18 (t, 7.8 Hz, 1H; RCHOH) ppm. $^{13}$C{$^1$H} NMR (CDCl$_3$, 75 MHz): δ 19.99, 25.03, 26.09, 26.31, 26.67, 28.52, 29.03, 42.01, 60.67, 67.22, 74.30 ppm. IR (neat): 3442 (OH), 2920, 2849, 2362, 1730, 1451, 1380, 1261, 1095, 1022 cm$^{-1}$. HRMS-CI m/z 183.1380 [M–H$^+$; calcd for C$_{11}$H$_{19}$O$_2$: 183.1385].

Example 63

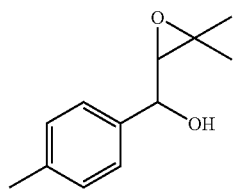

Preparation of threo-(S)-1-(1-Methyl-2-oxiranyl-4-p-tolyl)-butan-4-ol

The product was prepared by General procedure R using 61.5 mg (0.35 mmol) 4, 115 μL (1.12 mmol, neat) Et$_2$Zn, 3.4 mg (0.014 mmol) (–)-MIB, 42.1 mg (0.35 mmol) p-Tolualdehyde, and 19.9 mg (0.070 mmol) Ti(OiPr)$_4$. The crude product was purified by column chromatography on silica (60:30:10, hexanes:CH$_2$Cl$_2$:EtOAc) to afford the title compound as a colorless oil in 84% yield (56.6 mg, 0.29 mmol, mixture of diastereomers). [α]$_D^{20}$=–7.8 (c=0.10, CHCl$_3$). $^1$H NMR (CDCl$_3$, 500 MHz): δ 1.30 (s, 3H; C[CH$_3$] [CH$_3$]), 1.43 (s, 3H; C[CH$_3$] [CH$_3$]), 2.36 (s, 3H; ArCH$_3$), 2.51 (d, 2 Hz, 1H; OH), 2.97 (d, 8 Hz, 1H; epoxide), 4.54 (dd, 8, 1.5 Hz, 1H; RCHOH), 7.20 (d, 8 Hz, 2H; Ar), 7.28 (d, 8 Hz, 2H; Ar) ppm. $^{13}$C{$^1$H} NMR (CDCl$_3$, 125 MHz): δ 19.85, 21.38, 25.09, 60.24, 68.33, 72.81, 126.15, 129.58, 137.42, 138.07 ppm. IR (neat): 3401 (OH), 2966, 2919, 2355, 2345, 1907, 1713, 1613, 1514, 1455, 1414, 1378, 1261, 1196, 1149, 1091, 1043 cm$^{-1}$. HRMS-CI m/z 174.1040 [(M–H$_2$O)$^+$; calcd for C$_{12}$H$_{14}$O: 174.1045].

Example 64

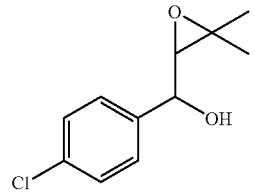

Preparation of threo-(S)-1-(1-Methyl-2-oxiranyl 4-p-chloro-phenyl)-butan-4-ol

The product was prepared by General procedure R using 87.3 mg (0.48 mmol) 4, 165 μL (1.61 mmol, neat) Et$_2$Zn, 4.7 mg (0.020 mmol) (–)-MIB, and 69.8 mg (0.49 mmol) p-chlorobenzaldehyde. The crude product was purified by column chromatography on silica (60:30:10, hexanes:CH$_2$Cl$_2$:

EtOAc) to afford the title compound as a colorless oil in 88% yield (93.1 mg, 0.44 mmol, mixture of diastereomers). $[\alpha]_D^{20}=-7.2$ (c=0.14, CHCl$_3$). $^1$H NMR (CDCl$_3$, 300 MHz): δ 1.31 (s, 3H; C[CH$_3$] [CH$_3$]), 1.45 (s, 3H; C[CH$_3$] [CH$_3$]), 2.64 (s, 1H; OH), 2.91 (d, 8 Hz, 1H; epoxide), 4.55 (d, 8 Hz, 1H; RCHOH), 7.34 (m, 4H; Ar) ppm. $^{13}$C{$^1$H} NMR (CDCl$_3$, 75.5 MHz): δ 19.86, 25.02, 60.44, 68.13, 72.21, 127.57, 129.09, 134.09, 138.79 ppm. IR (neat): 3413 (OH), 2978, 2931, 2367, 1907, 1596, 1490, 1455, 1378, 1249, 1132, 1090, 1043, 1014 cm$^{-1}$. HRMS-CI m/z 194.0493 [(M–H$_2$O)$^+$; calcd for C$_{11}$H$_{11}$OCl: 194.0498].

Example 65

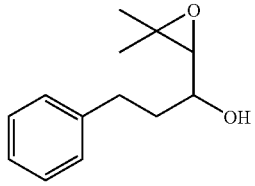

Preparation of threo-(S)-1-(1-Methyl-2-oxiranyl-4-hydrocinnamyl)-butan-4-ol

The product was prepared by General procedure R using 96.7 mg (0.55 mmol) 4, 180 μL (1.76 mmol, neat) Et$_2$Zn, 5.3 mg (0.022 mmol) (–)-MIB, 74.0 mg (0.55 mmol) hydrocinnamaldehyde, and 31.8 mg (0.112 mmol) Ti(OiPr)$_4$. The crude product was purified by column chromatography on silica (60:30:10, hexanes:CH$_2$Cl$_2$:EtOAc) to afford the title compound as a colorless oil in 88% yield (100.0 mg, 0.485 mmol). $[\alpha]_D^{20}=-31.9$ (c=0.05, CHCl$_3$). $^1$H NMR (CDCl$_3$, 300 MHz): δ 1.27 (s, 3H; C[CH$_3$] [CH$_3$]), 1.34 (s, 3H; C[CH$_3$] [CH$_3$]), 1.84 (m, 1H; methylene), 1.99 (m, 1H; methylene), 2.19 (s, 1H; OH), 2.70 (m, 1H; methylene), 2.77 (d, 8 Hz, 1H; epoxide), 2.89 (m, 1H; methylene), 3.53 (dq, 13, 8 Hz, 1H; RCHOH), 7.24 (d, 8 Hz, 2H; Ph), 7.33 (d, 8 Hz, 2H; Ph), 7.35 (t, 7.5 Hz, 1H; Ph) ppm. $^{13}$C{$^1$H} NMR (CDCl$_3$, 75.5 MHz): δ 19.39, 25.09, 31.46, 35.70, 59.80, 67.79, 69.96, 126.21, 128.59, 128.65, 141.75 ppm. IR (neat): 3430 (OH), 2956, 2920, 2801, 1950, 1724, 1599, 1493, 1457, 1380, 1261, 1107, 1065, 1030 cm$^{-1}$. HRMS-CI m/z 189.1284 [(M–OH)$^+$; calcd for C$_{13}$H$_{17}$O: 189.1279].

Example 66

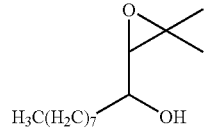

Preparation of threo-(S)-1-(1-Methyl-2-oxiranyl-4-octyl)-butan-4-ol

The product was prepared by General procedure R using 80.7 mg (0.46 mmol) 4, 150 μL (1.47 mmol, neat) Et$_2$Zn, 4.4 mg (0.018 mmol) (–)-MIB, 65.2 mg (0.46 mmol) nonyl aldehyde, and 26.9 mg (0.095 mmol) Ti(OiPr)$_4$. The crude product was purified by column chromatography on silica (60:30:10, hexanes:CH$_2$Cl$_2$:EtOAc) to afford the title compound as a colorless oil in 81.5% yield (80.0 mg, 0.37 mmol). $[\alpha]_D^{20}=-44.3$ (c=0.06, CHCl$_3$). $^1$H NMR (C$_6$D$_6$, 500 MHz): δ 0.90 (t, 7 Hz, 3H; CH$_3$), 1.06 (s, 6H; C[CH$_3$]$_2$), 1.25-1.48 (m, 13 H; methylene), 1.56 (m, 1H; methylene), 1.81 (br s, 1H; OH), 2.57 (d, 7.5 Hz, 1H; epoxide), 3.34 (br q, 7.5 Hz, 1H; RCHOH) ppm. $^{13}$C{$^1$H} NMR (C$_6$D$_6$, 125 MHz): δ 14.68, 19.73, 23.42, 25.24, 25.77, 30.06, 30.31, 30.43, 32.62, 34.93, 59.14, 68.16, 70.68 ppm. IR (neat): 3436 (OH), 2955, 2931, 2861, 2367, 1731, 1461, 1378, 1261, 1096, 1067 cm$^{-1}$. HRMS-CI m/z 197.1904 [(M–H$_2$O)+; calcd for C$_{13}$H$_{25}$O: 197.1905].

Example 67

Conditions for the Determination of Enantiomeric Excess

The enantiomeric excess values for the following allylic alcohols 1-5 were determined by chiral HPLC analysis using a Chiralcel OD-H column. Epoxy alcohol 6 was resolved using a Chiralcel AD column. The conditions for the resolution of the racemates are described below.

(1) (S)-2-Methyl-1-phenyl-pent-1-en-3-ol: $t_1$=31.0 min, $t_2$=35.1 min (hexane/2-propanol: 98/2, 1.0 mL/min).

(2) (S)-1-Phenyl-pent-1-en-ol: $t_1$=7.5 min, $t_2$=11.4 min (hexane/2-propanol: 90/10, 1.0 mL/min).

(3) (S)-4-Phenyl-but-3-en-2-ol: $t_1$=5.0 min, $t_2$=8.4 min (hexane/2-propanol: 90/10, 1.0 mL/min).

(4) (S)-2-Methyl-3-p-chloro-phenyl-propen-3-ol: $t_1$=7.8 min, $t_2$=9.5 min (hexane/2-propanol: 97/3, 1.0 mL/min).

(5) (S)-1-Methyl-4-hydracinnamyl-buten-4-ol: $t_1$=4.9 min, $t_2$=6.1 min (hexane/2-propanol: 97/3, 1.0 mL/min).

(6) erythro-6-(tert-Butyl-diphenyl-silanyloxy)-1-(7-oxabicyclo[4.1.0]hept-1-yl)hexan1-ol: $t_1$=10.3 min, $t_2$=12.5 min (hexane/2-propanol: 97/3, 0.5 mL/min).

The enantiomeric excess values for the following allylic alcohols 7-22 were determined by chiral capillary GC analysis using a Supleco β-Dex 120 fused silica column (30 m×0.25 mm×0.25 μm film thickness). The carrier gas was nitrogen; inlet temperature was 250° C.; FID detector at 270° C. The conditions for the resolution of the racemates are described below.

(7) (S)-4-Methyl-hept-4-en-3-ol: $t_1$=17.9 min, $t_2$=18.9 min (90° C., 0.3 mL/min).

(8) (S)-1-Cyclohex-1-enyl-5-methyl-hexan-1-ol: $t_1$=74.0 min, $t_2$=80.0 min (120° C., 1.0 mL/min).

(9) (S)-1-Cyclohex-1-enyl-propan-1-ol: $t_1$=25.2 min, $t_2$=25.8 min (115° C., 1.0 mL/min).

(10) (S)-5-Methyl-hex-4-en-3-ol: $t_1$=4.9 min, $t_2$=5.6 min (85° C., 1.0 mL/min).

(11) (S)-2-Ethyl-pent-1-en-3-ol: $t_1$=4.4 min, $t_2$=5.1 min (65° C., 1.0 mL/min).

(12) (S)-2,8-Dimethyl-non-2-en-4-ol: $t_1$=44.5 min, $t_2$=47.30 min (130° C., 0.5 mL/min).

(13) (S)-1-Cyclohex-1-enyl-ethanol: $t_1$=13.8 min, $t_2$=15.8 min (115° C., 1.0 mL/min).

(14) (S)-4-Methyl-pent-3-en-2-ol: $t_1$=19.4 min, $t_2$=27.4 min (65° C., 1.0 mL/min).

(15) (S)-2-Methyl-3-cyclohexyl-propen-3-ol.: $t_1$=33.4 min, $t_2$=34.3 min (100° C., 0.5 mL/min).

16) (S)-2-Methyl-3-p-tolyl-propen-3-ol: $t_1$=53.6 min, $t_2$=57.5 min (115° C., 0.5 mL/min).

(17) (S)-2-Methyl-3-hydracinnamyl-propen-3-ol: $t_1$=141.0 min, $t_2$=154.7 min (100° C., 0.5 mL/min).

18) (S)-2-Methyl-3-octyl-propen-3-ol: $t_1$=14.5 min, $t_2$=15.9 min (100° C., 1.0 mL/min).

19) (S)-1-Methyl-4-cyclohexyl-buten-4-ol: $t_1$=111.1 min, $t_2$=130.9 min (95° C., 0.5 mL/min).

20) (S)-1-Methyl-4-p-tolyl-buten-4-ol: $t_1$=102.7 min, $t_2$=105.6 min (100° C., 0.5 mL/min).

21) (S)-1-Methyl-4-p-chloro-phenyl-buten-4-ol: $t_1$=58.8 min, $t_2$=60.5 min (105° C., 1.0 mL/min).

22) (S)-1-Methyl-4-octyl-buten-4-ol: $t_1$=277.4 min, $t_2$=284.0 min (90° C., 0.5 mL/min).

Additional Examples

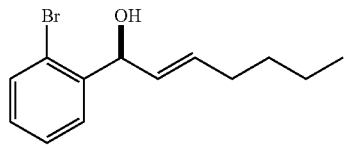

General Procedure S

Preparation of (S)-1-(2-Bromo-phenyl)-hept-2-en-1-ol (4)

A 10 mL Schlenk flask was charged with $Cy_2BH$ (98 mg, 0.55 mmol), prepared according to Oppolzer's procedure,[1] and 1.5 mL of hexanes. 1-Hexyne (64 µL, 0.55 mmol) was added dropwise, and the homogenous reaction mixture was stirred for 30 min at room temp. After cooling the reaction flask to −10° C., (−)-MIB (4.8 mg, 0.02 mmol) was added, followed by $Et_2Zn$ (0.55 mL, 2.0 M), then o-bromobenzaldehyde (58 µL, 0.50 mmol) dropwise. The reaction was stirred at −10° C. for 2 h and quenched with 2 mL $H_2O$. The organic and aqueous layers were separated, and the aqueous layer was extracted with hexanes (3×5 mL). The combined organic layers were then washed with 5 mL $H_2O$ and dried over $MgSO_4$. The filtrate was concentrated in vacuo, and the residue was chromatographed on silica (5% ethyl acetate in hexanes) to afford the title compound in 77% yield (104 mg, 0.39 mmol) as a colorless oil. $[\alpha]_D^{20}$=−31.3 (c=3.2, $CHCl_3$, 93% ee); $^1H$ NMR ($CDCl_3$, 500 MHz): δ 0.86 (t, 3H, J=7.1 Hz), 1.25-1.37 (m, 4H), 2.03 (dt, 2H, J=7.0, 6.7 Hz), 2.11 (br s, 1H), 5.51 (d, 1 H, J=6.1 Hz), 5.58 (dd, 1H, J=15.2, 6.4 Hz), 5.78 (dt, 1H, J=15.2, 6.7 Hz), 7.10 (t, 1H, J=7.6 Hz), 7.31 (t, 1H, J=7.4 Hz), 7.50 (d, 1H, J=7.9 Hz), and 7.53 (d, 1H, J=7.7 Hz) ppm; $^{13}C\{^1H\}$ NMR ($CDCl_3$, 125 MHz): δ 13.9, 22.2, 31.3, 31.9, 73.5, 122.4, 127.70, 127.74, 128.8, 130.2, 132.7, 133.5, and 142.2 ppm; IR (neat): 3360, 3060, 2956, 2926, 2857, 1664, 1567, 1466, 1438, 1378, and 1193 $cm^{-1}$; HRMS-CI m/z 268.0471 [$M^+$; calcd for $C_{13}H_{17}BrO$: 268.0463].

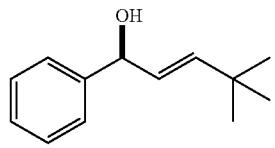

Preparation of (S)-4,4-Dimethyl-1-phenyl-pent-2-en-1-ol (1)

The product was prepared by General procedure S using 1.07 g (6.0 mmol) $Cy_2BH$, 739 µL (6.0 mmol) 2,2-dimethyl-1-butyne, 3.0 mL (6.0 mmol, 2.0 M in toluene) $Me_2Zn$, 24.0 mg (0.1 mmol) (−)-MIB, and 510 µL (5.0 mmol) benzaldehyde. The crude product was purified by column chromatography on silica (20% ethyl acetate in hexanes) to afford the title compound as a colorless oil in 86% yield (819 mg, 4.3 mmol). $[\alpha]_D^{20}$=+40.6 (c=1.00, $CHCl_3$, 96% ee); $^1H$ NMR ($CDCl_3$, 500 MHz): δ 1.14 (s, 9H), 2.54 (s, 1H), 5.19 (d, 1H, J=6.8 Hz), 5.65 (dd, 1H, J=15.4, 6.9 Hz), 5.86 (d, 1H, J=15.9 Hz), and 7.34-7.45 (m, 5H) ppm; $^{13}C\{^1H\}$ NMR ($CDCl_3$, 125 MHz): δ 30.0, 33.3, 75.7, 126.7, 127.8, 128.7, 128.9, 143.7, and 144.1 ppm; IR (neat): 3346, 3086, 3063, 3029, 2959, 2902, 2866, 1494, 1476, and 1453 $cm^{-1}$; HRMS-CI m/z 190.1356 [$M^+$; calcd for $C_{13}H_{18}O$: 190.1358].

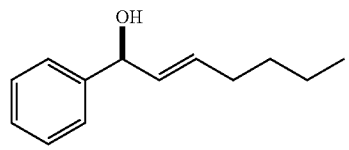

Preparation of (S)-1-Phenyl-hept-2-en-1-ol (2)

The product was prepared by General procedure S using 2.14 g (12.0 mmol) $Cy_2BH$, 1.4 mL (12.0 mmol) 1-hexyne, 6 mL (12.0 mmol, 2.0 M in toluene) $Me_2Zn$, 48 mg (0.2 mmol) (−)-MIB, and 1.01 mL (10.0 mmol) benzaldehyde. The crude product was purified by column chromatography on silica (5% ethyl acetate in hexanes) to afford the title compound as a colorless oil in 85% yield (1.62 g, 8.52 mmol). $[\alpha]_D^{20}$=+38.3 (c=1.01, $CHCl_3$, 95% ee); $^1H$ NMR ($CDCl_3$, 500 MHz): δ 0.85 (t, 3H, J=7.1 Hz), 1.22-1.37 (m, 4H), 1.81 (br s, 1H), 2.02 (dd, 2H, J=7.0, 6.5 Hz), 5.13 (d, 1H, J=6.6 Hz), 5.63 (dd, 1H, J=15.3, 6.7 Hz), 5.73 (dt, 1H, J=15.3, 6.6 Hz) and 7.22-7.34 (m, 5H) ppm; $^{13}C\{^1H\}$ NMR ($CDCl_3$, 125 MHz): δ 13.9, 22.2, 31.2, 31.8, 75.1, 126.1, 127.3, 128.4, 132.2, 132.7, and 143.4 ppm; IR (neat): 3354, 3068, 3027, 2926, 1667, and 1454 $cm^{-1}$; HRMS-CI m/z 190.1350 [$M^+$; calcd for $C_{13}H_{18}O$: 190.1358].

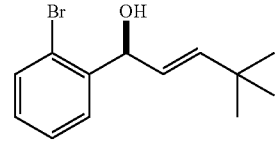

Preparation of (S)-1-(2-Bromo-phenyl)-4,4-dimethyl-pent-2-en-1-ol (3)

The product was prepared by General procedure S using 50 mg (0.28 mmol) $Cy_2BH$, 35 µL (0.28 mmol) 3,3-dimethyl-1-butyne, 0.26 mL (0.53 mmol, 2.0 M in hexanes) $Et_2Zn$, 2.4 mg (0.01 mmol) (−)-MIB, and 29 µL (0.25 mmol) o-bromobenzaldehyde. The crude product was purified by column chromatography (5% ethyl acetate in hexanes) to afford the title compound as a colorless oil in 76% yield (51 mg, 0.19 mmol). $[\alpha]_D^{20}$=−31.8 (c=0.33, $CHCl_3$, 93% ee); $^1H$ NMR ($CDCl_3$, 500 MHz): δ 1.02 (s, 9H), 2.03 (s, 1H), 5.46-5.53 (m, 2H), 5.86 (d, 1H, J=15.0 Hz), 7.13 (t, 1H, J=7.6 Hz), 7.33 (t, 1H, J=7.5 Hz), 7.52 (d, 1H, J=8.9 Hz), and 7.54 (d, 1H, J=8.2 Hz) ppm; $^{13}C\{^1H\}$ NMR ($CDCl_3$, 125 MHz): δ 29.4, 33.0, 73.8, 122.6, 125.0, 127.7, 127.8, 128.9, 132.8, 142.3, and 144.3 ppm; IR (neat): 3353, 3064, 3013, 2958, 2865, 1721, 1661, 1590, 1568, 1465, 1439, 1363, and 1267 cm$^{-1}$; HRMS-CI m/z 251.0432 [(M−OH)$^+$; calcd for $C_{13}H_{16}Br$: 251.0435].

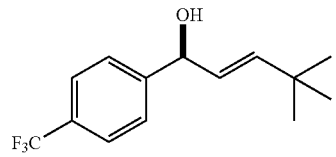

Preparation of (S)-4,4-Dimethyl-1-(4-trifluoromethyl-phenyl)-pent-2-en-1-ol (5)

The product was prepared by General procedure S using 98 mg (0.55 mmol) $Cy_2BH$, 68 μL (0.55 mmol) 3,3-dimethyl-1-butyne, 0.55 mL (1.1 mmol, 2.0 M in hexanes) $Et_2Zn$, 4.8 mg (0.02 mmol) (−)-MIB, and 68 μL (0.50 mmol) p-trifluoromethylbenzaldehyde. The crude product was purified by column chromatography (5% ethyl acetate in hexanes) to afford the title compound as a white solid in 89% yield (115 mg, 0.45 mmol). m.p.: 30-32° C.; $[\alpha]_D^{20}$=−10.0 (c=0.27, $CHCl_3$, 95% ee); $^1$H NMR ($CDCl_3$, 500 MHz): δ 0.98 (s, 9H), 2.03 (br s, 1H), 5.15 (d, 1H, J=7.0 Hz), 5.47 (dd, 1H, J=15.5, 7.2 Hz), 5.78 (d, 1H, J=15.6 Hz), 7.43 (d, 2H, J=8.0 Hz), and 7.55 (d, 2H, J=8.0 Hz) ppm; $^{13}$C{$^1$H} NMR ($CDCl_3$, 125 MHz): δ 29.3, 33.0, 74.9, 123.1, 125.28, 125.31, 125.34, 126.4, 126.7, 129.4, 129.7, 144.6, and 147.3 ppm; IR (film): 3335, 3025, 2962, 2905, 2868, 1661, 162.0, 1477, 1463, 1414, 1364, and 1327 cm$^{-1}$; HRMS-CI m/z 239.1247 [(M−F)$^+$; calcd for $C_{14}H_{17}F_2O$: 239.1247].

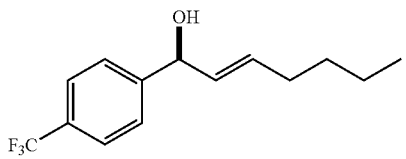

Preparation of (S)-1-(4-Trifluoromethyl-phenyl)-hept-2-en-1-ol (6)

The product was prepared by General procedure S using 98 mg (0.55 mmol) $Cy_2BH$, 64 μL (0.55 mmol) 1-hexyne, 0.55 mL (1.1 mmol, 2.0 M in hexanes) $Et_2Zn$, 4.8 mg (0.02 mmol) (−)-MIB, and 68 μL (0.50 mmol) p-trifluoromethylbenzaldehyde. The crude product was purified by column chromatography (5% ethyl acetate in hexanes) to afford the title compound as a colorless oily solid in 94% yield (121 mg, 0.47 mmol). $[\alpha]_D^{20}$=+69.3 (c=0.88, $CHCl_3$, 95% ee); $^1$H NMR ($CDCl_3$, 500 MHz): δ 0.88 (t, 3H, J=7.1 Hz), 1.25-1.39 (m, 4H), 1.61 (br s, 1H), 2.05 (dt, 2H, J=6.9, 6.7 Hz), 5.19 (d, 1H, J=7.0 Hz), 5.59 (dd, 1H, JT=15.3, 7.1 Hz), 5.77 (dt, 1H, J=15.3, 6.7 Hz), 7.46 (d, 2H, J=8.0 Hz), and 7.58 (d, 2H, J=8.0 Hz) ppm; $^{13}$C{$^1$H} NMR ($CDCl_3$, 125 MHz): δ 13.9, 22.2, 31.3, 31.8, 74.7, 125.3, 125.4, 126.4, 129.4, 129.7, 131.7, 133.9, and 147.2 ppm; IR (neat): 3370, 3037, 2959, 2930, 2859, 2353, 1666, 1620, 1415, 1327, and 1165 cm$^{-1}$; HRMS-ESI m/z 258.1239 [M$^+$; calcd for $C_{14}H_{17}F_3O$: 258.1232].

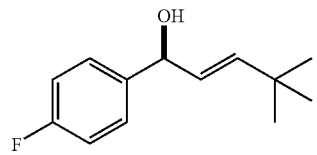

Preparation of (S)-1-(4-Fluoro-phenyl)-4,4-dimethyl-pent-2-en-1-ol (7)

The product was prepared by General procedure S using 98 mg (0.55 mmol) $Cy_2BH$, 68 μL (0.55 mmol) 3,3-dimethyl-1-butyne, 0.55 mL (1.1 mmol, 2.0 M in hexanes) $Et_2Zn$, 4.8 mg (0.02 mmol) (−)-MIB, and 54 μL (0.50 mmol) p-fluorobenzaldehyde. The crude product was purified by column chromatography (5% ethyl acetate in hexanes) to afford the title compound as a white solid in 82% yield (85 mg, 0.41 mmol). m.p.: 38-40° C.; $[\alpha]_D^{20}$=+21.3 (c=1.2, $CHCl_3$, 93% ee); $^1$H NMR ($CDCl_3$, 500 MHz): δ 1.01 (s, 9H), 1.84 (br s, 1H), 5.13 (d, 1H, J=6.9 Hz), 5.52 (dd, 1H, J=15.6, 6.9 Hz), 5.77 (d, 1H, J=15.6 Hz), 7.01 (t, 2H, J=8.7 Hz), and 7.31 (dd, 2H, J=8.3, 5.6 Hz) ppm; $^{13}$C{$^1$H} NMR ($CDCl_3$, 125 MHz): δ 29.4, 32.9, 74.7, 115.1, 115.3, 127.1, 127.77, 127.83, 139.18, 139.20, 143.7, 161.1, and 163.1 ppm; IR (film): 3344, 3025, 2959, 2866, 1725, 1661, 1604, 1509, 1463, 1363, 1294, 1225, and 1156 cm$^{-1}$; HRMS-CI m/z 208.1267 [M$^+$; calcd for $C_{13}H_{17}FO$: 208.1263].

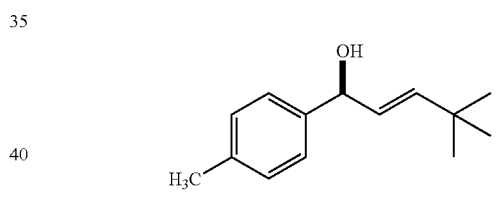

Preparation of (S)-4,4-Dimethyl-1-p-tolyl-pent-2-en-1ol (8)

The product was prepared by General procedure S using 98 mg (0.55 mmol) $Cy_2BH$, 68 μL (0.55 mmol) 3,3-dimethyl-1-butyne, 0.55 mL (1.1 mmol, 2.0 M in hexanes) $Et_2Zn$, 4.8 mg (0.02 mmol) (−)-MIB, and 59 μL (0.50 mmol) p-tolualdehyde. The crude product was purified by column chromatography (5% ethyl acetate in hexanes) to afford the title compound as a white solid in 86% yield (88 mg, 0.43 mmol). m.p.: 38-40° C.; $[\alpha]_D^{20}$=+52.7 (c=0.97, $CHCl_3$, 95% ee); $^1$H NMR ($CDCl_3$, 500 MHz): δ 0.95 (s, 9H), 1.83 (br s, 1H), 2.26 (s, 3H), 5.03 (d, 1H, J=6.7 Hz), 5.47 (dd, 1H, J=15.6, 6.8 Hz), 5.70 (d, 1H, J=15.6 Hz), 7.07 (d, 2H, J=7.7 Hz), and 7.17 (d, 2H, J=7.9 Hz) ppm; $^{13}$C{$^1$H} NMR ($CDCl_3$, 125 MHz): δ 21.1, 29.4, 32.8, 75.2, 126.1, 127.2, 128.1, 137.1, 140.6, and 143.2 ppm; IR (film): 3346, 3023, 2959, 2865, 2361, 2334, 1655, 1613, 1513, 1478, 1461, 1416, 1388, 1362, and 1268 cm$^{-1}$; HRMS-CI m/z 204.1509 [M$^+$; calcd for $C_{14}H_{20}O$: 204.1514].

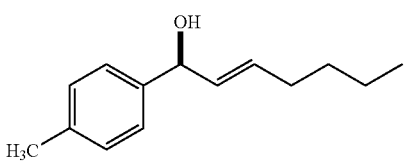

Preparation of (S)-1-p-Tolyl-hept-2-en-1-ol (9)

The product was prepared by General procedure S using 98 mg (0.55 mmol) Cy$_2$BH, 64 μL (0.55 mmol) 1-hexyne, 0.55 mL (1.1 mmol, 2.0 M in hexanes) Et$_2$Zn, 4.8 mg (0.02 mmol) (−)-MIB, and 59 μL (0.50 mmol) p-tolualdehyde. The crude product was purified by column chromatography (5% ethyl acetate in hexanes) to afford the title compound as a colorless oil in 87% yield (89 mg, 0.44 mmol). $[\alpha]_D^{20}$=+43.1 (c=1.3, CHCl$_3$, 95% ee); $^1$H NMR (CDCl$_3$, 500 MHz): δ 0.81 (t, 3H, J=7.1 Hz), 1.20-1.32 (m, 4H), 1.81 (br s, 1H), 1.97 (dt, 2H, J=7.0, 6.6 Hz), 2.26 (s, 3H), 5.04 (d, 1H, J=6.5 Hz), 5.57 (dd, 1H, J=15.3, 6.6 Hz), 5.66 (dt, 1H, J=15.3, 6.5 Hz), 7.07 (d, 2H, J=7.8 Hz), and 7.17 (d, 2H, J=7.8 Hz) ppm; $^{13}$C{$^1$H} NMR (CDCl$_3$, 125 MHz): δ 13.9, 21.1, 22.2, 31.2, 31.9, 75.1, 126.1, 129.1, 132.3, 132.5, 137.1, and, 140.5 ppm; IR (neat): 3346, 3017, 2957, 2925, 2858, 1663, 1613, 1513, 1456, 1377, and 1198 cm$^{-1}$; HRMS-CI m/z 203.1440 [(M−H)$^+$; calcd for C$_{14}$H$_{19}$O: 203.1436].

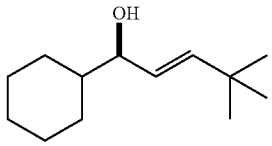

Preparation of (S)-1-Cyclohexyl-4,4-dimethyl-pent-2-en-1-ol (10)

The product was prepared by General procedure S using 98 mg (0.55 mmol) Cy$_2$BH, 68 μL (0.55 mmol) 3,3-dimethyl-1-butyne, 0.55 mL (1.1 mmol, 2.0 M in hexanes) Et$_2$Zn, 4.8 mg (0.02 mmol) (−)-MIB, and 61 μL (0.50 mmol) cyclohexanecarboxaldehyde. The crude product was purified by column chromatography (5% ethyl acetate in hexanes) to afford the title compound as a colorless oil in 80% yield (78 mg, 0.40 mmol). $[\alpha]_D^{20}$=−27.7 (c=0.13, CHCl$_3$, 96% ee); $^1$H NMR (CDCl$_3$, 500 MHz): δ 0.92-0.97 (m, 2H), 1.01 (s, 9H), 1.11-1.26 (m, 4H), 1.41 (m, 1H), 1.64 (m, 2H), 1.73 (m, 2H), 1.86 (br d, 1H, J=12.6 Hz), 3.75 (t, 1H, J=7.0 Hz), 5.35 (dd, 1H, J=15.6, 7.5 Hz), and 5.62 (d, 1H, J=15.7 Hz) ppm; $^{13}$C{$^1$H} NMR (CDCl$_3$, 125 MHz): δ 26.1, 26.2, 26.6, 28.76, 28.84, 29.6, 32.9, 43.8, 77.9, 126.2, and 143.9 ppm; IR (neat): 3351, 2953, 2926, 2853, 1655, 1473, 1450, 1387, 1362, 1305, 1260, and 1204 cm$^{-1}$; HRMS-CI m/z 195.1743 [(M−H)$^+$; calcd for C$_{13}$H$_{23}$O: 195.1749].

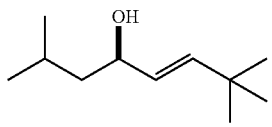

Preparation of (S)-2,7,7-Trimethyl-oct-5-en-4-ol (11)

The product was prepared by General procedure S using 196 mg (1.1 mmol) Cy$_2$BH, 137 μL (1.1 mmol) 3,3-dimethyl-1-butyne, 1.1 mL (2.1 mmol, 2.0 M in hexanes) Et$_2$Zn, 9.6 mg (0.04 mmol) (−)-MIB, and 107 μL (1.0 mmol) isovaleraldehyde. The crude product was purified by column chromatography (5% ethyl acetate in hexanes) to afford the title compound as a colorless oil in 86% yield (146 mg, 0.86 mmol). $[\alpha]_D^{20}$=+16.7 (c=3.0, CHCl$_3$, 85% ee); $^1$H NMR (CDCl$_3$, 500 MHz): δ 0.88 (t, 6H, J=7.0 Hz), 0.97 (s, 9H), 1.26 (m, 1H), 1.43 (m, 1H), 1.50 (br s, 1H), 1.65 (m, 1H), 4.07 (dt, 1H, J=7.0, 6.8 Hz), 5.31 (dd, 1H, J=15.6, 7.2 Hz), and 5.61 (d, 1H, J=15.7 Hz) ppm; $^{13}$C{$^1$H} NMR (CDCl$_3$, 1.25 MHz): δ 22.5, 22.9, 24.6, 29.5, 32.5, 46.6, 71.5, 128.1, and 142.6 ppm; IR (neat): 3334, 3013, 2956, 2869, 2354, 2320, 1662, 1466, 1386, 1363, 1308, 1268, 1220, and 1202 cm$^{-1}$; HRMS-CI m/z 170.1666 [M$^+$; calcd for C$_{11}$H$_{22}$O: 170.1671].

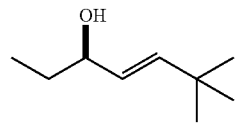

Preparation of (S)-6,6-Dimethyl-hept-4-en-3-ol (12)

The product was prepared by General procedure S using 196 mg (1.1 mmol) Cy$_2$BH, 137 μL (1.1 mmol) 3,3-dimethyl-1-butyne, 1.1 mL (2.1 mmol, 2.0 M in hexanes) Et$_2$Zn, 9.6 mg (0.04 mmol) (−)-MIB, and 72 μL (1.0 mmol) propanal. The crude product was purified by column chromatography (5% ethyl acetate in hexanes) to afford the title compound as a colorless oil in 68% yield (96 mg, 0.68 mmol). $[\alpha]_D^{20}$=−60.3 (c=0.63, CHCl$_3$, 77% ee); $^1$H NMR (CDCl$_3$, 500 MHz): δ 0.86 (t, 3H, J=7.4 Hz), 0.98 (s, 9H), 1.26 (br s, 1H), 1.44-1.59 (m, 2H), 3.93 (dt, 1H, J=6.6, 6.6 Hz), 5.31 (dd, 1H, J=15.7, 7.1 Hz), and 5.62 (d, 1H, J=15.7 Hz) ppm; $^{13}$C{$^1$H} NMR (CDCl$_3$, 125 MHz): δ 9.7, 22.6, 29.5, 30.2, 74.7, 127.4, and 143.2 ppm; IR (neat): 3360, 3025, 2960, 2866, 1660, 1478, 1463, 1414, 1384, 1363, 1331, and 1262 cm$^{-1}$; HRMS-CI m/z 141.1274 [(M−H)$^+$; calcd for C$_9$H$_{17}$O: 141.1279].

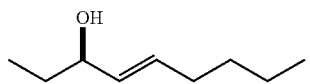

Preparation of (S)-Non-4-en-3-ol (13)

The product was prepared by General procedure S using 50 mg (0.28 mmol) Cy$_2$BH, 32 μL (0.28 mmol) 1-hexyne, 0.39 mL (0.78 mmol, 2.0 M in hexanes) Et$_2$Zn, 2.4 mg (0.01 mmol) (−)-MIB, and 18 μL (0.25 mmol) propanal. The crude product was purified by column chromatography (5% ethyl acetate in hexanes) to afford the title compound as a colorless oil in 74% yield (26 mg, 0.18 mmol). $[\alpha]_D^{20}$=+58.5 (c=0.97, CHCl$_3$, 79% ee); $^1$H NMR (CDCl$_3$, 500 MHz): δ 0.87 (m, 6H), 1.22-1.36 (m, 4H), 1.39 (br s, 1H), 1.43-1.57 (m, 2H), 2.00 (dt, 2H, J=7.0, 6.6 Hz), 3.94 (dt, 1H, J=6.6, 6.6 Hz), 5.41 (dd, 1H, J=15.3, 7.0 Hz), and 5.60 (dt, 1H, J=15.3, 6.7 Hz) ppm; $^{13}$C{$^1$H} NMR (CDCl$_3$, 125 MHz): δ 9.7, 13.9, 22.2, 30.2, 31.4, 31.9, 74.6, 132.4, and 132.7 ppm; IR (neat): 3421,

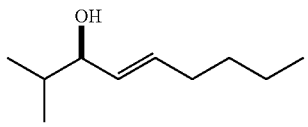

Preparation of (S)-2-Methyl-non-4-en-3-ol (14)

The product was prepared by General procedure S using 98 mg (0.55 mmol) Cy$_2$BH, 64 µL (0.55 mmol) 1-hexyne, 0.55 mL (1.1 mmol, 2.0 M in hexanes) Et$_2$Zn, 4.8 mg (0.02 mmol) (−)-MIB, and 45 µL (0.50 mmol) isobutyraldehyde. The crude product was purified by column chromatography (5% ethyl acetate in hexanes) to afford the title compound as a colorless oil in 88% yield (69 mg, 0.44 mmol). $[\alpha]_D^{20}$=−12.5 (c=1.3, CHCl$_3$, 92% ee); $^1$H NMR (CDCl$_3$, 500 MHz): δ 0.82 (d, 3H, J=6.7 Hz), 0.84 (t, 3H, J=7.2 Hz), 0.87 (d, 3H, J=6.7 Hz), 1.23-1.32 (m, 4H), 1.48 (br s, 1H), 1.64 (m, 1H), 1.99 (dt, 2H, J=6.8, 6.55 Hz), 3.72 (t, 1H, J=6.5 Hz), 5.40 (dd, 1H, J=15.3, 7.2 Hz), and 5.57 (dt, 1H, J=15.3, 6.7 Hz) ppm; $^{13}$C{$^1$H} NMR (CDCl$_3$, 125 MHz): δ 13.9, 18.1, 18.2, 22.2, 31.4, 32.0, 33.8, 78.3, 131.1, and 133.2 ppm; IR (neat): 3221, 2953, 2925, 2862, 1488, 1466, 1381, 1331, 1260, and 1194 cm$^{-1}$; LRMS-CI m/z 139.14 [(M−OH)$^+$; calcd for C$_{10}$H$_{19}$: 139.15].

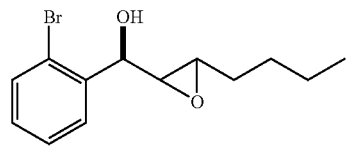

General Procedure T

Preparation of 2-Bromo-phenyl)-(3-butyl-oxiranyl)-methanol (18)

A 10 mL Schlenk flask (A) was charged with Cy$_2$BH (98 mg, 0.55 mmol), prepared according to Oppolzer's procedure,[1] and 1.2 mL of hexanes. 1-Hexyne (64 µL, 0.55 mmol) was added dropwise, and the homogenous reaction mixture was stirred for 30 min at room temp. After cooling the reaction flask to −10° C., (−)-MIB (4.8 mg, 0.02 mmol) was added, followed by Et$_2$Zn (0.78 mL, 2.0 M), then o-bromobenzaldehyde (58 µL, 0.50 mmol) dropwise. The reaction was stirred at −10° C. for 4 h until vinyl addition was complete by TLC. The reaction flask was then capped with a balloon of oxygen and allowed to stir at −10° C. for 1 h. In a separate 10 mL Schlenk flask (B), 1 mL of dichloromethane, Ti(OiPr)$_4$ (100 µL, 1.0 M in hexanes), and (+)-DIPT (21 µL, 0.10 mmol) were combined. After stirring at room temp for 45 min, flask B was evacuated for 1 h to strip off the solvent. The contents of flask B were then redissolved in 1 mL of dichloromethane and stripped again for 1 h. Finally, the contents of flask B were taken up in 1 mL of dichloromethane and transferred to reaction flask A. The reaction continued to stir at −10° C. under an O$_2$ atmosphere for 18 h. It was then quenched with 2 mL 15% tartaric acid solution and allowed to stir for 45 min before the organic and aqueous layers were separated, and the aqueous layer was extracted with hexanes (3×5 mL). The combined organic layers were then washed with 5 mL H$_2$O and dried over MgSO$_4$. The filtrate was concentrated in vacuo and the residue was chromatographed on silica (5% ethyl acetate in hexanes) to afford the title compound in 77% yield (110 mg, 0.39 mmol). threo-diastereomer: Colorless oil. $[\alpha]_D^{20}$=−40.5 (c=0.39, CHCl$_3$); $^1$H NMR (CDCl$_3$, 500 MHz): δ 0.87 (t, 3H, J=7.1 Hz), 1.27-1.44 (m, 4H), 1.53-1.61 (m, 2H), 2.51 (d, 1H, J=5.4 Hz), 2.98 (dd, 1H, J=4.5, 2.1 Hz), 3.24 (dt, 1H, J=5.6, 2.0 Hz), 5.02 (t, 1H, J=4.9 Hz), 7.18 (t, 1H, J=7.6 Hz), 7.37 (t, 1H, J=7.5 Hz), 7.56 (d, 1H, J=7.9 Hz), and 7.61 (d, 1H, J=7.7 Hz) ppm; $^{13}$C{$^1$H} NMR (CDCl$_3$, 125 MHz): δ 13.9, 22.4, 27.9, 31.1, 57.7, 61.1, 71.6, 122.1, 127.9, 128.0, 129.5, 132.8, and 139.8 ppm; IR (neat): 3424, 3063, 2962, 2930, 2861, 1562, 1468, 1434, 1383, and 1260 cm$^{-1}$; HRMS-CI m/z 285.0496 [MH$^+$; calcd for C$_{13}$H$_{18}$BrO$_2$: 285.0490]. erythro-diastereomer: Colorless oil. $[\alpha]_D^{20}$=−55.9 (c=1.2, CHCl$_3$); $^1$H NMR (CDCl$_3$, 500 MHz): δ 0.82 (t, 3H, J=7.1 Hz), 1.20-1.33 (m, 4H), 1.44 (m, 1H), 1.55 (m, 1H), 2.51 (s, 1H), 3.03 (dt, 1H, J=5.6, 1.8 Hz), 3.20 (br t, 1H), 5.37 (br s, 1H), 7.17 (t, 1H, J=7.1 Hz), 7.34 (t, 1H, J=7.5 Hz), 7.50 (d, 1H, J=7.6 Hz), and 7.54 (d, 1H, J=8.0 Hz) ppm; $^{13}$C{$^1$H} NMR (CDCl$_3$, 125 MHz): δ 13.8, 22.2, 27.9, 31.0, 54.8, 59.6, 69.1, 122.1, 127.7, 127.9, 129.4, 132.6, and 138.8 ppm; IR (neat): 3434, 3072, 2957, 2931, 2859, 1590, 1568, 1468, 1438, and 1378 cm$^{-1}$; HRMS-CI m/z 285.0496 [MH$^+$; calcd for C$_{13}$H$_{18}$BrO$_2$: 285.0490].

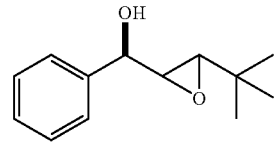

Preparation of (3-tert-Butyl-oxiranyl)-phenyl-methanol (15)

The product was prepared by General procedure T using 50 mg (0.28 mmol) Cy$_2$BH, 35 µL (0.28 mmol) 3,3-dimethyl-1-butyne, 0.39 mL (0.78 mmol, 2.0 M in hexanes) Et$_2$Zn, 2.4 mg (0.01 mmol) (−)-MIB, 25 µL (0.25 mmol) benzaldehyde, 50 µL (0.05 mmol, 1.0 M in hexanes) Ti(OiPr)$_4$, and 10.6 µL (0.05 mmol) (+)-DIPT. The crude product was purified by column chromatography (5% ethyl acetate in hexanes) to afford the title compound in 77% yield (40 mg, 0.19 mmol). threo-diastereomer: White solid. m.p.: 70-73° C. $[\alpha]_D^{20}$=−25.6 (c=0.16, CHCl$_3$); $^1$H NMR (CDCl$_3$, 500 MHz): δ 0.83 (s, 9H), 2.32 (br s, 1H), 2.82 (d, 1H, J=1.6 Hz), 3.01 (dd, 1H, J=5.3, 1.9 Hz), 4.46 (t, 1H, J=4.4 Hz), 7.26 (t, 1H, J=6.9 Hz), and 7.31-7.36 (m, 4H) ppm; $^{13}$C{$^1$H} NMR (CDCl$_3$, 125 MHz): δ 25.7, 30.6, 59.3, 65.1, 74.2, 126.0, 128.0, 128.6, and 140.5 ppm; IR (film): 3413, 3049, 3025, 2955, 2919, 2861, 2355, 1719, 1602, 1478, 1455, 1390, 1360, 1273, 1237, and 1196 cm$^{-1}$; HRMS-CI m/z 189.1288. [(M−OH)$^+$; calcd for C$_3$H$_{17}$O: 189.1279]. erythro-diastereomer: White solid. m.p.: 57-59° C.; $[\alpha]_D^{20}$=−27.1 (c=0.31, CHCl$_3$); $^1$H NMR (CDCl$_3$, 500 MHz): δ 0.82 (s, 9H), 2.20 (br s, 1H), 2.96 (d, 1H, J=2.0 Hz), 3.01 (t, 1H, J=2.7 Hz), 4.82 (br s, 1H), and 7.26-7.32 (m, 5H) ppm; $^{13}$C{$^1$H} NMR (CDCl$_3$, 125 MHz): δ 25.8, 30.4, 58.3, 62.8, 71.2, 126.5, 128.3, 128.6, and 139.8 ppm; IR (film): 3413, 3037, 2955, 2931, 2861, 1719, 1643, 1602, 1449, 1367, and 1327 cm$^{-1}$; HRMS-CI m/z 189.1288 [(M−OH)$^+$; calcd for C$_{13}$H$_{17}$O: 189.1279].

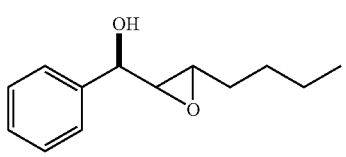

Preparation of (3-Butyl-oxiranyl)-phenyl-methanol (16)

The product was prepared by General procedure T using 50 mg (0.28 mmol) Cy$_2$BH, 32 μL (0.28 mmol) 1-hexyne, 0.39 mL (0.78 mmol, 2.0 M in hexanes) Et$_2$Zn, 2.4 mg (0.01 mmol) (−)-MIB, 25 μL (0.25 mmol) benzaldehyde, 50 μL (0.05 mmol, 1.0 M in hexanes) Ti(OiPr)$_4$, and 10.6 μL (0.05 mmol) (+)-DIPT. The crude product was purified by column chromatography (5% ethyl acetate in hexanes) to afford the title compound in 83% yield (43 mg, 0.21 mmol): threo-diastereomer: Colorless oil. $[\alpha]_D^{20}$=−12.9 (c=2.5, CHCl$_3$); $^1$H NMR (CDCl$_3$, 500 MHz): δ 0.83 (t, 3H, J=7.1 Hz), 1.22-1.41 (m, 4H), 1.46-1.56 (m, 2H), 2.31 (br s, 1H), 2.93 (dt, 1H, J=5.2, 2.0 Hz), 3.01 (dt, 1H, J=5.7, 5.4 Hz), 4.48 (d, 1H, J=2.0 Hz), and 7.27-7.38 (m, 5H) ppm; $^{13}$C{$^1$H} NMR (CDCl$_3$, 125 MHz): δ 14.0, 22.5, 28.1, 31.3, 57.7, 62.6, 74.4, 126.9, 128.8, 129.4, and 141.2 ppm; IR (neat): 3420, 3060, 2957, 2931, 2859, 1713, 1692, 1600, 1578, 1490, 1452, 1408, 1384, and 1314 cm$^{-1}$; HRMS-ESI m/z 189.1275 [(M−OH)$^+$; calcd for C$_{13}$H$_{17}$O: 189.1279]. erythro-diastereomer: Colorless oil. $[\alpha]_D^{20}$=−10.7 (c=0.43, CHCl$_3$); $^1$H NMR (CDCl$_3$, 500 MHz): δ 0.83 (t, 3H, J=7.1 Hz), 1.22-1.38 (m, 4H), 1.44-1.56 (m, 2H), 2.22 (br s, 1H), 2.94 (t, 1H, J=2.4 Hz), 3.13 (dt, 1H, J=5.8, 5.4 Hz), 4.84 (d, 1H, J=2.6 Hz), and 7.28-7.35 (m, 5H) ppm; $^{13}$C{$^1$H} NMR (CDCl$_3$, 125 MHz): δ 14.0, 22.5, 28.2, 31.3, 55.5, 61.7, 71.4, 127.2, 129.0, 129.4, and 139.6 ppm; IR (neat): 3420, 3060, 3025, 2957, 2930, 2859, 1725, 1605, 1496, 1453, 1378, 1284, 1237, and 1190 cm$^{-1}$; HRMS-ESI m/z 189.1275 [(M−OH)$^+$; calcd for C$_{13}$H$_{17}$O: 189.1279].

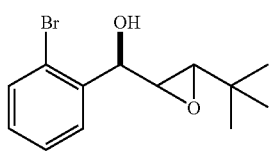

Preparation of (2-Bromo-phenyl)-(3-tert-butyl-oxiranyl)-methanol (17)

The product was prepared by General procedure T using 50 mg (0.28 mmol) Cy$_2$BH, 35 μL (0.28 mmol) 3,3-dimethyl-1-butyne, 0.39 mL (0.78 mmol, 2.0 M in hexanes) Et$_2$Zn, 2.4 mg (0.01 mmol) (−)-MIB, 29 μL (0.25 mmol) o-bromobenzaldehyde, 0.25 mL (0.25 mmol, 1.0 M in hexanes) Ti(OiPr)$_4$, and 63 μL (0.30 mmol) (+)-DIPT. The crude product was purified by column chromatography (5% ethyl acetate in hexanes) to afford the title compound in 78% yield (55 mg, 0.19 mmol). threo-diastereomer: Colorless oil. $[\alpha]_D^{20}$=−65.8 (c=0.40, CHCl$_3$); $^1$H NMR (CDCl$_3$, 500 MHz): δ 0.90 (s, 9H), 2.55 (d, 1H, J=5.2 Hz), 3.08 (m, 2H), 5.00 (t, 1H, J=4.6 Hz), 7.18 (t, 1H, J=7.6 Hz), 7.37 (t, 1H, J=7.5 Hz), 7.55 (d, 1H, J=7.9 Hz), and 7.61 (d, 1H, J=7.3 Hz) ppm; $^{13}$C{$^1$H} NMR (CDCl$_3$, 125 MHz): δ 25.7, 30.6, 58.2, 65.2, 71.7, 122.0, 127.88, 127.94, 129.4, 132.8, and 140 ppm; IR (neat): 3418, 3060, 2957, 2872, 2343, 1568, 1469, 1437, 1396, 1365, and 1190 cm$^{-1}$; HRMS-CI m/z 267.0368 [(M−OH)$^+$; calcd for C$_{13}$H$_{16}$BrO: 267.0385]. erythro-diastereomer: Colorless oil. $[\alpha]_D^{20}$=−55.5 (c=0.53, CHCl$_3$); $^1$H NMR (CDCl$_3$, 500 MHz): δ 0.84 (s, 9H), 2.42 (br d, 1H, J=2.1 Hz), 2.85 (br d, 1H, J=2.3 Hz), 3.29 (t, 1H, J=2.4 Hz), 5.40 (br s, 1H), 7.17 (t, 1H, J=7.4 Hz), 7.34 (t, 1H, J=7.4 Hz), 7.51 (d, 1H, J=7.7 Hz), and 7.54 (d, 1H, J=8.0 Hz) ppm; $^{13}$C{$^1$H} NMR (CDCl$_3$, 125 MHz): δ 25.7, 30.3, 56.5, 62.3, 69.1, 122.1, 127.7, 127.9, 129.4, 132.6, and 138.9 ppm; IR (neat): 3426, 3060, 2958, 2861, 1631, 1590, 1586, 1467, 1439, 1390, and 1364 cm$^{-1}$; HRMS-CI m/z 267.0368 [(M−OH)$^+$; calcd for C$_{13}$H$_{16}$BrO: 267.0385].

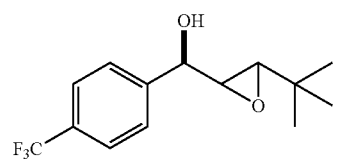

Preparation of (3-tert-Butyl-oxiranyl)-(4-trifluoromethyl-phenyl)-methanol (19)

The product was prepared by General procedure T using 50 mg (0.28 mmol) Cy$_2$BH, 35 μL (0.28 mmol) 3,3-dimethyl-1-butyne, 0.39 mL (0.78 mmol, 2.0 M in hexanes) Et$_2$Zn, 2.4 mg (0.01 mmol) (−)-MIB, 34 μL (0.25 mmol) p-trifluoromethylbenzaldehyde, 50 μL (0.05 mmol, 1.0 M in hexanes) Ti(OiPr)$_4$, and 10.6 μL (0.05 mmol) (+)-DIPT. The crude product was purified by column chromatography (5% ethyl acetate in hexanes) to afford the title compound in 85% yield (58 mg, 0.21 mmol). threo-diastereomer: Colorless solid. m.p.: 76-79° C.; $[\alpha]_D^{20}$=−10.0 (c=0.27, CHCl$_3$); $^1$H NMR (CDCl$_3$, 500 MHz): δ 0.90 (s, 10H), 2.89 (d, 1H, J=2.2 Hz), 3.03 (dd, 1H, J=5.5, 2.2 Hz), 4.58 (d, 1H, J=5.4 Hz), 7.53 (d, 2H, J=8.1 Hz), and 7.64 (d, 2H, J=8.1 Hz) ppm; $^{13}$C{$^1$H} NMR (CDCl$_3$, 125 MHz): δ 25.7, 30.6, 59.0, 65.3, 73.6, 125.54, 125.58, 125.59, and 126.3 ppm; IR (film): 3411, 3028, 2969, 2927, 2871, 2367, 2332, 1622, 1477, 1460, 1420, 1365, 1331, and 1241 cm$^{-1}$; HRMS-CI m/z 255.1192 [(M−F)$^+$; calcd for C$_{14}$H$_{17}$F$_2$O$_2$: 255.1197]. erythro-diastereomer: Colorless solid. m.p.: 74-75° C.; $[\alpha]_D^{20}$=−32.0 (c=0.10, CHCl$_3$); $^1$H NMR (CDCl$_3$, 500 MHz): δ 0.83 (s, 9H), 2.30 (br s, 1H), 2.93 (d, 1H, J=2.0 Hz), 3.03 (t, 1H, J=2.6 Hz), 4.90 (d, 1H, J=2.2 Hz), 7.48 (d, 2H, J=8.0 Hz), and 7.60 (d, 2H, J=8.0 Hz) ppm; $^{13}$C{$^1$H} NMR (CDCl$_3$, 125 MHz): δ 25.7, 31.6, 57.9, 62.8, 75.6, 125.50, 125.51, 125.53, and 126.6 ppm; IR (film): 3350, 3037, 2955, 2868, 1661, 1620, 1477, 1463, 1414, 1365, and 1327 cm$^{-1}$; HRMS-CI m/z 255.1192 [(M−F)$^+$; calcd for C$_{14}$H$_{17}$F$_2$O$_2$: 255.1197].

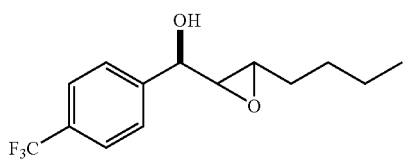

Preparation of (3-Butyl-oxiranyl)-(4-trifluoromethyl-phenyl)-methanol (20)

The product was prepared by General procedure T using 98 mg (0.55 mmol) Cy$_2$BH, 64 μL (0.55 mmol) 1-hexyne, 0.78 mL (1.55 mmol, 2.0 M in hexanes) Et₂Zn, 4.8 mg (0.02 mmol) (−)-MIB, 68 μL (0.50 mmol) p-trifluoromethylbenzaldehyde, 100 μL (0.10 mmol, 1.0 M in hexanes) Ti(OiPr)₄, and 21 μL (0.10 mmol) (+)-DIPT. The crude product was purified by column chromatography (5% ethyl acetate in hexanes) to afford the title compound in 76% yield (104 mg, 0.38 mmol). threo-diastereomer: Colorless oil. $[\alpha]_D^{20}$=−22.4 (c=0.25, CHCl₃); ¹H NMR (CDCl₃, 500 MHz): δ 0.81 (t, 3H, J=7.1 Hz), 1.19-1.35 (m, 3H), 1.45-1.53 (m, 3H), 2.37 (br d, 1H, J=3.7 Hz), 2.87 (dt, 1H, J=5.1, 1.8 Hz), 3.00 (dt, 1H, J=5.3, 1.3 Hz), 4.53 (br t, 1H), 7.46 (d, 2H, J=8.0 Hz), and 7.57 (d, 2H, J=8.0 Hz) ppm; ¹³C{¹H} NMR (CDCl₃, 125 MHz): δ 13.9, 22.4, 27.9, 31.1, 57.4, 61.8, 73.2, 125.56, 125.59, 126.4, and 144.2 ppm; IR (neat): 3432, 2960, 2931, 2860, 2352, 2326, 1621, 1469, 1456, 1417, 1380, 1326, and 1260 cm⁻¹; HRMS-ESI m/z 255.1187 [(M−F)⁺; calcd for C₁₄H₁₇F₂O₂: 255.1197]. erythro-diastereomer: Colorless oil. $[\alpha]_D^{20}$=−26.0 (c=0.80, CHCl₃); ¹H NMR (CDCl₃, 500 MHz): δ 0.77 (t, 3H, J=7.2 Hz), 1.15-1.32 (m, 3H), 1.38-1.52 (m, 3H), 2.27 (br s, 1H), 2.91 (t, 1H, J=2.6 Hz), 3.04 (dt, 1H, J=5.8, 2.0 Hz), 4.87 (br s, 1H), 7.44 (d, 2H, J=8.0 Hz), and 7.57 (d, 2H, J=8.0 Hz) ppm; ¹³C{¹H} NMR (CDCl₃, 125 MHz): δ 13.8, 22.3, 28.0, 31.0, 55.2, 61.0, 70.5, 125.49, 125.52, 126.5, and 143.7 ppm; IR (neat): 3425, 3013, 2966, 2932, 2861, 1619, 1457, 1414, 1384, 1326, and 1261 cm⁻¹; HRMS-ESI m/z 255.1187 [(M−F)⁺; calcd for C₁₄H₁₇F₂O₂: 255.1197].

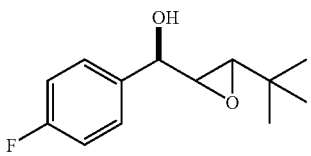

Preparation of (3-tert-Butyl-oxiranyl)-(4-fluoro-phenyl)-methanol (21)

The product was prepared by General procedure T using 98 mg (0.55 mmol) Cy₂BH, 68 μL (0.55 mmol) 3,3-dimethyl-1-butyne, 0.78 mL (1.55 mmol, 2.0 M in hexanes) Et₂Zn, 4.8 mg (0.02 mmol) (−)-MIB, 54 μL (0.50 mmol) p-fluorobenzaldehyde, 100 μL (0.10 mmol, 1.0 M in hexanes) Ti(OiPr)₄, and 21 μL (0.10 mmol) (+)-DIPT. The crude product was purified by column chromatography (5% ethyl acetate in hexanes) to afford the title compound in 92% yield (103 mg, 0.46 mmol). threo-diastereomer: Colorless solid. m.p.: 83-85° C.; $[\alpha]_D^{20}$=−14.8 (c=0.23, CHCl₃); ¹H NMR (CDCl₃, 500 MHz): δ 0.82 (s, 9H), 2.31 (br s, 1H), 2.78 (d, 1H, J=2.1 Hz), 2.95 (dd, 1H, J=5.5, 2.2 Hz), 4.42 (d, 1H, J=5.2 Hz), 6.99 (t, 2H, J=8.6 Hz), and 7.31 (dd, 2H, J=8.3, 5.5 Hz) ppm; ¹³C{¹H} NMR (CDCl₃, 125 MHz): δ 25.7, 30.6, 59.2, 65.1, 73.6, 115.4, 115.6, 127.68, 127.74, 136.2, and 163.5 ppm; IR (neat): 3403, 3002, 2963, 2919, 2872, 1725, 1661, 1637, 1603, 1511, 1461, 1390, 1361, and 1226 cm⁻¹; HRMS-CI m/z 224.1206 [M⁺; calcd for C₁₃H₁₇FO₂: 224.1213]. erythro-diastereomer: Colorless solid. m.p.: 56-59° C.; $[\alpha]_D^{20}$=−34.3 (c=0.40, CHCl₃); ¹H NMR (CDCl₃, 500 MHz): δ 0.85 (s, 9H), 2.28 (br s, 1H), 2.96 (d, 1H, J=2.1 Hz), 3.01 (t, 1H, J=2.7 Hz), 4.84 (br d, 1H, J=2.8 Hz), 7.04 (t, 2H, J=8.5 Hz), and 7.34 (dd, 2H, J=8.3, 5.5 Hz) ppm; ¹³C{¹H} NMR (CDCl₃, 125 MHz): δ 25.8, 30.4, 58.2, 62.7, 70.5, 115.4, 115.6, 128.08, 128.15, 135.6, and 163.6 ppm; IR (KBr): 3409, 3015, 2964, 2871, 1606, 1510, 1463, 1392, 1369, 1331, and 1316 cm⁻¹; HRMS-CI m/z 224.1206 [M⁺; calcd for C₁₃H₁₇FO₂: 224.1213].

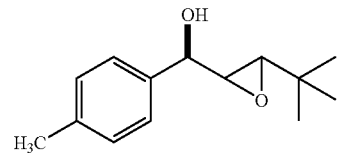

Preparation of (3-tert-Butyl-oxiranyl)-p-tolyl-methanol (22)

The product was prepared, by General procedure T using 98 mg (0.55 mmol) Cy₂BH, 68 μL (0.55 mmol) 3,3-dimethyl-1-butyne, 0.78 mL (1.55 mmol, 2.0 M in hexanes) Et₂Zn, 4.8 mg (0.02 mmol) (−)-MIB, 59 μL (0.50 mmol) p-tolualdehyde, 100 μL, (0.10 mmol, 1.0 M in hexanes) Ti(OiPr)₄, and 21 μL (0.10 mmol) (+)-DIPT. The crude product was purified by column chromatography (5% ethyl acetate in hexanes) to afford the title compound in 85% yield (93 mg, 0.42 mmol). threo-diastereomer: White solid. m.p.: 36-39° C.; $[\alpha]_D^{20}$=−40.0 (c=0.26, CHCl₃); ¹H NMR (CDCl₃, 500 MHz): δ 0.81 (s, 9H), 2.28 (s, 3H), 2.35 (br d, 1H, J=3.9 Hz), 2.78 (d, 1H, J=2.2 Hz), 2.97 (dd, 1H, J=5.5, 2.2 Hz), 4.39 (br t, 1H), 7.10 (d, 2H, J=7.8 Hz), and 7.22 (d, 2H, J=7.9 Hz) ppm; ¹³C{¹H} NMR (CDCl₃, 125 MHz): δ 21.1, 25.7, 30.6, 59.4, 65.1, 74.1, 125.9, 129.2, 137.5, and 137.7 ppm; IR (film): 3416, 3095, 2957, 2867, 1614, 1514, 1482, 1463, 1417, 1393, 1365, 1260, and 1239 cm⁻¹; HRMS-CI m/z 203.1431 [(M−OH)⁺; calcd for C₁₄H₁₉O: 203.1436]. erythro-diastereomer: White solid. m.p.: 65-68° C.; $[\alpha]_D^{20}$=−58.2 (c=0.57, CHCl₃); ¹H NMR (CDCl₃, 500 MHz): δ 0.82 (s, 9H), 2.16 (br s, 1H), 2.28 (s, 3H), 2.95 (d, 1H, J=2.1 Hz), 2.97 (t, 1H, J=2.7 Hz), 4.76 (br s, 1H), 7.10 (d, 2H, J=7.7 Hz), and 7.19 (d, 2H, J=8.0 Hz) ppm; ¹³C{¹H} NMR (CDCl₃, 125 MHz): □ 21.2, 25.8, 30.4, 58.3, 62.8, 71.1, 126.5, 129.2, 136.8, and 137.9 ppm; IR (film): 3418, 3018, 2965, 2923, 2867, 1919, 1515, 1478, 1458, 1412, 1381, and 1322 cm⁻¹; HRMS-CI m/z 203.1431 [(M−OH)⁺; calcd for C₁₄H₁₉O: 203.1436].

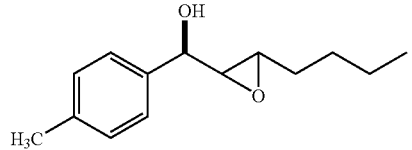

Preparation of (3-Butyl-oxiranyl)-p-tolyl-methanol (23)

The product was prepared by General procedure T using 89 mg (0.55 mmol) Cy₂BH, 64 μL (0.55 mmol) 1-hexyne, 0.78 mL (1.55 mmol, 2.0 M in hexanes) Et₂Zn, 4.8 mg (0.02 mmol) (−)-MIB, 59 μL (0.50 mmol) p-tolualdehyde, 100 μL (0.10 mmol, 1.0 M in hexanes) Ti(OiPr)₄, and 21 μL (0.10 mmol) (+)-DIPT. The crude product was purified by column chromatography (5% ethyl, acetate in hexanes) to afford the title compound in 83% yield (92 mg, 0.42 mmol). threo-diastereomer: Colorless oil. $[\alpha]_D^{20}$=−18.7 (c=0.31, CHCl₃); ¹H NMR (CDCl₃, 500 MHz): δ 0.81 (t, 3H, J=7.1 Hz), 1.20-

1.34 (m, 4H), 1.46-1.51 (m, 2H), 2.25 (br d, 1H, J=4.1 Hz), 2.30 (s, 3H), 2.90 (dd, 1H, J=5.2, 2.0 Hz), 2.97 (dt, 1H, J=5.5, 1.8 Hz), 4.42 (br t, 1H), 7.13 (d, 2H, J=7.7 Hz), and 7.23 (d, 2H, J=7.9 Hz) ppm; $^{13}C\{^1H\}$ NMR (CDCl$_3$, 125 MHz): δ 13.9, 21.1, 22.4, 28.0, 31.2, 57.3, 62.2, 73.8, 126.1, 126.4, 129.3, and 137.5 ppm; IR (neat): 3428, 3051, 2961, 2928, 2860, 2356, 1646, 1512, 1462, 1383, 1260, and 1192 cm$^{-1}$; HRMS-CI m/z 202.1362 [(M−H$_2$O)$^+$; calcd for C$_{14}$H$_{18}$O: 202.1358]. erythro-diastereomer: Colorless oil. $[\alpha]_D^{20}$=−58.4 (c=0.25, CHCl$_3$); $^1$H NMR (CDCl$_3$, 500 MHz): δ 0.79 (t, 3H, J=7.1 Hz), 1.19-1.33 (m, 4H), 1.43-1.50 (m, 2H), 2.15 (br s, 1H), 2.28 (s, 3H), 2.89 (t, 1H, J=2.5 Hz), 3.10 (dt, 1H, J=5.6, 1.5 Hz), 4.77 (br s, 1H), 7.11 (d, 2H, J=7.8 Hz), and 7.19 (d, 2H, J=8.1 Hz) ppm; $^{13}C\{^1H\}$ NMR (CDCl$_3$, 125 MHz): δ 13.9, 21.2, 22.4, 28.0, 31.2, 55.2, 61.3, 70.9, 126.4, 129.3, 136.7, and 138.0 ppm; IR (neat): 3430, 3028, 2950, 2916, 2860, 2356, 2334, 1680, 1607, 1512, 1461, 1383, and 1265 cm$^{-1}$; HRMS-CI m/z 202.1362 [(M−H$_2$O)$^+$; calcd for C$_{14}$H$_{18}$O: 202.1358].

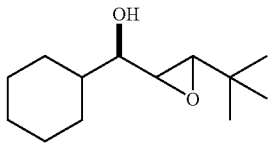

Preparation of (3-tert-Butyl-oxiranyl)-cyclohexyl-methanol (24)

The product was prepared by General procedure T using 98 mg (0.55 mmol) Cy$_2$BH, 68 μL (0.55 mmol) 3,3-dimethyl-1-butyne, 0.78 mL (1.55 mmol, 2.0 M in hexanes) Et$_2$Zn, 4.8 mg (0.02 mmol) (−)-MIB, 61 μL (0.50 mmol) cyclohexane carboxaldehyde, 100 μL (0.10 mmol, 1.0 M in hexanes) Ti(OiPr)$_4$, and 21 μL (0.10 mmol) (+)-DIPT. The crude product was purified by column chromatography (5% ethyl acetate in hexanes) to afford the title compound in 74% yield (79 mg, 0.37 mmol). threo-diastereomer: White solid. m.p.: 48-50° C.; $[\alpha]_D^{20}$=+70.7 (c=0.68, CHCl$_3$); $^1$H NMR (CDCl$_3$, 500 MHz): δ 0.92 (s, 9H), 1.00-1.19 (m, 6H), 1.47 (m, 1H), 1.64-1.87 (m, 5H), 2.79 (d, 1H, J=2.1 Hz), 2.92 (t, 1H, J=2.5 Hz), and 3.57 (t, 1H, J=3.1 Hz) ppm; $^{13}C\{^1H\}$ NMR (CDCl$_3$, 125 MHz): δ 25.9, 26.0, 26.2, 26.5, 28.5, 28.8, 30.5, 41.8, 56.5, 6214, and 72.3 ppm; IR (KBr): 3392, 2922, 2853, 1643, 1449, 1391, 1363, 1262, 1245, and 1211 cm$^{-1}$; HRMS-CI m/z 213.1865 [MH$^+$; calcd for C$_{13}$H$_{25}$O$_2$: 213.1855]. erythro-diastereomer: White solid. m.p.: 38-48° C.; $[\alpha]_D^{20}$=−38.9 (c=0.27, CHCl$_3$); $^1$H NMR (CDCl$_3$, 500 MHz): δ 0.92 (s, 9H), 1.03-1.28 (m, 6H), 1.66 (m, 1H), 1.73 (m, 3H), 1.89 (m, 2H), 2.67 (d, 1H, J=2.0 Hz), 2.87 (dd, 1H, J=5.4, 2.1 Hz), and 3.13 (m, 1H) ppm; $^{13}C\{^1H\}$ NMR (CDCl$_3$, 125 MHz): δ 25.8, 26.0, 26.1, 26.4, 28.6, 28.8, 30.7, 42.2, 57.5, 65.0, and 75.9 ppm; IR (KBr): 3503, 2961, 2929, 2852, 1481, 1447, 1391, 1368, 1312, and 1284 cm$^{-1}$; HRMS-CI m/z 213.1865 [MH$^+$; calcd for C$_{13}$H$_{25}$O$_2$: 213.1855].

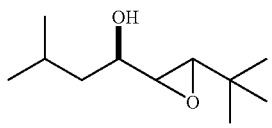

Preparation of 1-(3-tert-Butyl-oxiranyl)-3-methyl-butan-1-ol (25)

The product was prepared by General procedure T using 50 mg (0.28 mmol) Cy$_2$BH, 35 μL (0.28 mmol) 3,3-dimethyl-1-butyne, 0.39 mL (0.78 mmol, 2.0 M in hexanes) Et$_2$Zn, 2.4 mg (0.01 mmol) (−)-MIB, 27 μL, (0.25 mmol) isovaleraldehyde, 50 μL (0.05 mmol, 1.0 M in hexanes) Ti(OiPr)$_4$, and 10.6 μL (0.05 mmol) (+)-DIPT. The crude product was purified by column chromatography (5% ethyl acetate in hexanes) to afford the title compound in 89% yield (42 mg, 0.23 mmol). threo-diastereomer: Colorless oil. $[\alpha]_D^{20}$=+72.5 (c=0.67, CHCl$_3$); $^1$H NMR (CDCl$_3$, 500 MHz): δ 0.90 (s, 9H), 0.91 (d, 3H, J=6.7 Hz), 0.93 (d, 3H, J=6.7 Hz), 1.24-1.29 (m, 1H), 1.36-1.42 (m, 1H), 1.78 (br s, 1H), 1.83 (m, 1H), 2.77 (d, 1H, J=2.3 Hz), 2.83 (t, 1H, J=2.7 Hz), and 3.86 (m, 1H) ppm; $^{13}C\{^1H\}$ NMR (CDCl$_3$, 125 MHz): δ 22.0, 23.5, 24.5, 25.8, 31.6, 42.6, 58.0, 62.3, and 66.5 ppm; IR (neat): 3410, 2957, 2923, 2862, 1730, 1483, 1467, 1387, 1365, 1285, 1261, and 1209 cm$^{-1}$; HRMS-CI m/z 169.1585 [(M−OH)$^+$; calcd for C$_{11}$H$_{21}$O: 169.1592]. erythro-diastereomer: Colorless oil. $[\alpha]_D^{20}$= □□ (c=0.53, CHCl$_3$); $^1$H NMR (CDCl$_3$, 500 MHz): δ 0.90 (s, 9H), 0.93 (t, 6H, J=6.8 Hz), 1.27-1.31 (m, 1H), 1.49-1.53 (m, 1H), 1.55 (br s, 1H), 1.79-1.82 (m, 1H), 2.68 (d, 1H, J=2.2 Hz), 2.78 (dd, 1H, J=5.4, 2.3 Hz), and 3.47 (m, 1H) ppm; $^{13}C\{^1H\}$ NMR (CDCl$_3$, 125 MHz): δ 22.1, 23.2, 24.3, 25.8, 31.6, 43.2, 59.1, 64.9, and 70.1 ppm; IR (neat): 3379, 2959, 2923, 2872, 1726, 1483, 1463, 1417, 1361, and 1255 cm$^{-1}$; HRMS-CI m/z 167.1585 [(M−OH)$^+$; calcd for C$_{11}$H$_{21}$O: 169.1592].

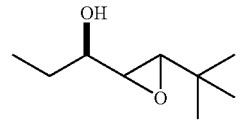

Preparation of 1-(3-tert-Butyl-oxiranyl)-propan-1-ol (26)

The product was prepared by General procedure T using 196 mg (1.1 mmol) Cy$_2$BH, 137 μL (1.1 mmol) 3,3-dimethyl-1-butyne, 1.1 mL (2.1 mmol, 2.0 M in hexanes) Et$_2$Zn, 9.6 mg (0.04 mmol) (−)-MIB, 72 μL (1.0 mmol) propanal, 200 μL (0.20 mmol, 1.0 M in hexanes) Ti(OiPr)$_4$, and 42 μL (0.20 mmol) (+)-DIPT. The crude product was purified by column chromatography (5% ethyl acetate in hexanes) to afford the title compound in 69% yield (109 mg, 0.69 mmol). threo-diastereomer: Colorless oil. $[\alpha]_D^{20}$=+80.3 (c=0.79, CHCl$_3$); $^1$H NMR (CDCl$_3$, 500 MHz): δ 0.90 (s, 9H), 0.96 (t, 3H, J=7.5 Hz), 1.56-1.62 (m, 2H), 1.84 (br d, 1H, J=4.6 Hz), 2.67 (d, 1H, J=2.2 Hz), 2.80 (dd, 1H, J=5.1, 1.8 Hz), and 3.32 (m, 1H) ppm; $^{13}C\{^1H\}$ NMR (CDCl$_3$, 125 MHz): δ 22.6, 25.8, 27.4, 31.6, 58.5, 64.7, and 73.2 ppm; IR (neat): 3401, 2955, 2851, 1728, 1602, 1578, 1462, 1370, 1367, and 1273 cm$^{-1}$; LRMS-CI m/z 141.08 [(M−OH)$^+$; calcd for C$_9$H$_{17}$O: 141.13]. erythro-diastereomer: Colorless oil. $[\alpha]_D^{20}$=28.0 (c=0.79, CHCl$_3$); $^1$H NMR (CDCl$_3$, 500 MHz): δ 0.90 (s, 9H), 0.99 (t, 3H, J=7.5 Hz), 1.47-1.60 (m, 2H), 1.79 (br s, 1H), 2.78 (d, 1H, J=2.2 Hz), 2.85 (t, 1H, J=2.7 Hz), and 3.72 (m, 1H) ppm; $^{13}C\{^1H\}$ NMR (CDCl$_3$, 125 MHz): δ 22.6, 25.8, 26.6, 31.6, 57.5, 62.4, and 69.6 ppm; IR (neat): 3366, 2955, 2922, 2849, 2367, 2332, 1725, 1596, 1455, and 1373 cm$^{-1}$; LRMS-CI m/z 141.08 [(M−OH)$^+$; calcd for C$_9$H$_{17}$O: 141.13].

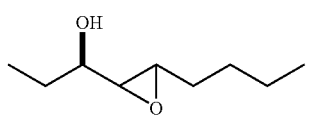

Preparation of 1-(3-Butyl-oxiranyl)-propan-1-ol (27)

The product was prepared by General procedure T using 50 mg (0.28 mmol) Cy$_2$BH, 32 μL (0.28 mmol) 1-hexyne, 0.39 mL (0.78 mmol, 2.0 M in hexanes) Et$_2$Zn, 2.4 mg (0.01 mmol) (−)-MIB, 18 μL (0.25 mmol) propanal, 50 μL (0.05 mmol, 1.0 M in hexanes) Ti(OiPr)$_4$, and 21 μL (0.10 mmol) (+)-DIPT. The crude product was purified by column chromatography (5% ethyl acetate in hexanes) to afford the title compound in 68% yield (27 mg, 0.17 mmol). threo-diastereomer: Colorless oil. $[\alpha]_D^{20}$=−12.5 (c=0.12, CHCl$_3$); $^1$H NMR (CDCl$_3$, 500 MHz): δ 0.88 (t, 3H, J=7.0 Hz), 0.99 (t, 3H, J=7.5 Hz), 1.31-1.41 (m, 4H), 1.48-1.62 (m, 4H), 1.76 (br s, 1H), 2.73 (br t, 1H, J=2.7 Hz), 2.96 (dt, 1H, J=5.7, 2.0 Hz), and 3.70 (m, 1H) ppm; $^{13}$C{$^1$H} NMR (CDCl$_3$, 125 MHz): δ 9.6, 13.9, 22.5, 26.5, 28.1, 31.3, 54.9, 60.7, and 69.7 ppm; IR (neat): 3356, 2960, 2922, 2852, 2355, 2332, 1729, 1463, 1414, 1378, and 1261 cm$^{-1}$; HRMS-CI m/z 141.1273 [(M−OH)$^+$; calcd for C$_9$H$_{17}$O: 141.1279]. erythro-diastereomer: Colorless oil. $[\alpha]_D^{20}$=9.2 (c=0.41, CHCl$_3$); $^1$H NMR (CDCl$_3$, 500 MHz): δ 0.88 (t, 3H, J=7.0 Hz), 0.97 (t, 3H, J=7.5 Hz), 1.22-1.27 (m, 2H), 1.30-1.43 (m, 4H), 1.48-1.56 (m, 2H), 1.82 (br s, 1H), 2.70 (dd, 1H, J=4.9, 2.1 Hz), 2.87 (dt, 1H, J=5.6, 2.0 Hz), and 3.35 (m, 1H) ppm; $^{13}$C{$^1$H} NMR (CDCl$_3$, 125 MHz): δ 9.7, 13.9, 22.5, 27.5, 28.0, 31.3, 56.9, 61.5, and 72.6 ppm; IR (neat): 3424, 2959, 2922, 2851, 2362, 2332, 1731, 1463, 1408, and 1373 cm$^{-1}$; HRMS-CI m/z 141.1273 [(M−OH)$^+$; calcd for C$_9$H$_{17}$O: 141.1279].

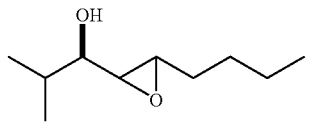

Preparation of 1-(3-Butyl-oxiranyl)-2-methyl-propan-1-ol (28)

The product was prepared by General procedure T using 98 mg (0.55 mmol) Cy$_2$BH, 64 μL (0.55 mmol) 1-hexyne, 0.78 mL (1.55 mmol, 2.0 M in hexanes) Et$_2$Zn, 4.8 mg (0.02 mmol) (−)-MIB, 45 μL (0.50 mmol) isobutyraldehyde, 100 μL (0.10 mmol, 1.0 M in hexanes) Ti(OiPr)$_4$, and 21 μL (0.10 mmol) (+)-DIPT. The crude product was purified by column chromatography (5% ethyl acetate in hexanes) to afford the title compound in 77% yield (66 mg, 0.38 mmol). threo-diastereomer: Colorless oil. $[\alpha]_D^{20}$=−26.3 (c=0.79, CHCl$_3$); $^1$H NMR (CDCl$_3$, 500 MHz): δ 0.85 (t, 3H, J=7.1 Hz), 0.91 (d, 3H, J=6.8 Hz), 0.94 (d, 3H, J=6.8 Hz), 1.27-1.41 (m, 4H), 1.47-1.52 (m, 2H), 1.75 (m, 1H), 1.84 (d, 1H, J=5.7 Hz), 2.70 (dd, 1H, J=5.0, 2.1 Hz), 2.82 (dt, 1H, J=5.7, 1.6 Hz), and 3.10 (q, 1H, J=5.7 Hz) ppm; $^{13}$C{$^1$H} NMR (CDCl$_3$, 125 MHz): δ 13.9, 18.1, 18.4, 22.5, 28.0, 31.3, 32.5, 57.1, 60.3, and 76.0 ppm; IR (neat): 3414, 2959, 2930, 2862, 1466, 1381, 1366, 1280, and 1255 cm$^{-1}$; LRMS-CI m/z 155.17 [(M−OH)$^+$; calcd for C$_{10}$H$_{19}$O: 155.14]. erythro-diastereomer: Colorless oil. $[\alpha]_D^{20}$=8.1 (c=0.36, CHCl$_3$); $^1$H NMR (CDCl$_3$, 500 MHz): δ 0.85 (t, 3H, J=7.0 Hz), 0.93 (d, 3H, J=6.2 Hz), 0.94 (d, 3H, J=6.0 Hz), 1.29-1.40 (m, 4H), 1.50 (dt, 2H, J=7.2, 6.2 Hz), 1.75 (m, 1H), 1.78 (br s, 1H), 2.74 (t, 1H, J=2.4 Hz), 2.94 (dt, 1H, J=5.4, 2.0 Hz), and 3.51 (br t, 1H) ppm; $^{13}$C{$^1$H} NMR (CDCl$_3$, 125 MHz): δ 13.9, 17.8, 18.5, 22.5, 28.1, 31.3, 31.7, 54.9, 59.6, and 73.0 ppm; IR (neat): 3412, 2963, 2929, 2872, 1640, 1534, 1458, and 1381 cm$^{-1}$; LRMS-CI m/z 155.17 [(M−OH)$^+$; calcd for C$_{10}$H$_{19}$O: 155.14].

Conditions for the Determination of Enantiomeric Excess

The enantiomeric excess values for the following compounds were determined by chiral HPLC analysis. The conditions for the resolution of the racemates are described below.

(S)-4,4-Dimethyl-1-phenyl-pent-2-en-1-ol (1): Chiralcel OD-H; $t_1$=9.2 min, $t_2$=11.5 min (hexanes/2-propanol: 95/5, 0.8 mL/min).

(S)-1-Phenyl-hept-2-en-1-ol (2): Chiralcel OD-H; $t_1$=20.3 min, $t_2$=22.5 min (hexanes/2-propanol: 98/2, 0.5 mL/min).

(S)-1-(2-Bromo-phenyl)-4,4-dimethyl-pent-2-en-1-ol (3): Chiralcel OD-H; $t_1$=13.4 min, $t_2$=16.4 min (hexanes/2-propanol: 97/3, 0.5 mL/min).

(S)-1-(2-Bromo-phenyl)-hept-2-en-1-ol (4): Chiralcel OD-H; $t_1$=15.9 min, $t_2$=19.8 min (hexanes/2-propanol: 97/3, 0.5 mL/min).

(S)-1-(4-Trifluoromethyl-phenyl)-hept-2-en-1-ol (6): Chiralcel OB-H; $t_1$=23.1 min, $t_2$=31.3 min (hexanes/2-propanol: 98/2, 0.5 mL/min).

(S)-4,4-Dimethyl-1-p-tolyl-pent-2-en-1ol (8): Chiralcel OD-H; $t_1$=18.8 min, $t_2$=21.8 min (hexanes/2-propanol: 98/2, 0.5 mL/min).

(S)-1-p-Tolyl-hept-2-en-1-ol (9): Chiralcel OD-H; $t_1$=22.1 min, $t_2$=25.0 min (hexanes/2-propanol: 98/2, 0.5 mL/min).

(3-tert-Butyl-oxiranyl)-(4-trifluoromethyl-phenyl)-methanol (19): Chiralcel OD-H; $t_1$=20.8 min, $t_2$=26.3 min (hexanes/2-propanol: 97/3, 0.5 mL/min).

The enantiomeric excess values for the following compounds were determined by chiral capillary GC analysis using a Supelco β-Dex 120 fused silica column (30 m×0.25 mm×0.25 mm film thickness). The carrier gas was nitrogen; inlet temperature was 250° C.; FID detector at 270° C. The conditions for the resolution of the racemates are described below.

(S)-1-(4-Fluoro-phenyl)-4,4-dimethyl-pent-2-en-1-ol (7): $t_1$=371.1 min, $t_2$=376.6 min (110° C., 0.5 mL/min).

(S)-1-Cyclohexyl-4,4-dimethyl-pent-2-en-1-ol (10): $t_1$=98.4 min, $t_2$=101.5 min (110° C., 1.2 mL/min).

(S)-2,7,7-Trimethyl-oct-5-en-4-ol (11): $t_1$=22.6 min, $t_2$=24.6 min (110° C., 0.8 mL/min).

(S)-6,6-Dimethyl-hept-4-en-3-ol (12): $t_1$=48.0 min, $t_2$=49.3 min (80° C., 0.8 mL/min).

(S)-Non-4-en-3-ol (13): $t_1$=79.6 min, $t_2$=81.7 min (80° C., 0.8 mL/min).

(S)-2-Methyl-non-4-en-3-ol (14): $t_1$=35.6 min, $t_2$=37.0 min (100° C., 0.8 mL/min).

The inventive subject matter being thus described, it will be obvious that the same may be modified or varied in many ways. Such modifications and variations are not to be regarded as a departure from the spirit and scope of the inventive subject matter and all such modifications and variations are intended to be included within the scope of the following claims.

We claim:

1. A highly enantio- and diastereoselective process for making an epoxy alcohol from an aldehyde, comprising the steps of:

(a) adding (i) an organozinc compound or (ii) a divinylzinc compound and a diorganozinc compound to said aldehyde in the presence of a first catalyst to form an allylic alkoxide compound, said first catalyst being selected from the group consisting of amino alcohol-based catalysts and bis(sulfonamide) catalysts; and (b) epoxidizing said allylic alkoxide compound in the presence of an oxidant and a second catalyst, said second catalyst being a transition metal catalyst.

2. The process of claim 1, wherein said aldehyde is selected from the group consisting of α,β-unsaturated, aliphatic, and aromatic aldehydes.

3. The process of claim 1, wherein said organozinc compound is a compound of formula $Zn(R^1)_2$:
wherein
each said $R^1$ is independently selected from the group consisting of:
straight or branched chain $C_1$-$C_9$ alkyl,
straight or branched chain $C_1$-$C_9$ alkyl substituted with one or more halo, trifluoromethyl, nitro, $C_1$-$C_6$ straight or branched chain alkyl, $C_2$-$C_6$ straight or branched chain alkenyl, hydroxy, $C_1$-$C_4$ alkoxy, $C_2$-$C_4$ alkenyloxy, phenoxy, benzyloxy, amino, or Ar,
straight or branched chain $C_2$-$C_9$ alkenyl or alkynyl, and straight or branched chain $C_2$-$C_9$ alkenyl or alkynyl substituted with one or more halo, trifluoromethyl, nitro, $C_1$-$C_6$ straight or branched chain alkyl, $C_2$-$C_6$ straight or branched chain alkenyl, hydroxy, $C_1$-$C_4$ alkoxy, $C_2$-$C_4$ alkenyloxy, phenoxy, benzyloxy, amino or Ar,
$C_3$-$C_8$ cycloalkyl, $C_5$-$C_7$ cycloalkenyl, carboxy, cyano, Ar,
wherein Ar is an alicyclic or aromatic, mono-, bi- or tricyclic, carbo- or heterocyclic ring, and the individual ring size is 5-8 members; wherein the heterocyclic ring contains 1-4 heteroatom(s) independently selected from the group consisting of O, N, and S.

4. The process of claim 1, wherein said divinylzinc compound is a compound of formula I:

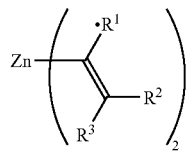

wherein
$R^1$, $R^2$, and $R^3$ are independently selected from the group consisting of:
hydrogen,
straight or branched chain $C_1$-$C_9$ alkyl, strait or branched chain $C_1$-$C_9$ alkyl substituted with at least one halo, trifluoromethyl, $C_1$-$C_6$ straight or branched chain alkyl, $C_2$-$C_6$ straight or branched chain alkenyl, $C_1$-$C_4$ alkoxy, $C_2$-$C_4$ alkenyloxy, phenoxy, benzyloxy amino, or Ar,
O—($C_1$-$C_9$ straight or branched chain alkyl), straight or branched chain $C_2$-$C_9$ alkenyl or alkynyl, and straight or branched chain $C_2$-$C_9$ alkenyl or alkynyl substituted with one or more halo, trifluoromethyl, nitro, $C_1$-$C_6$ straight or branched chain alkyl, $C_2$-$C_6$ straight or branched chain alkenyl, hydroxy, $C_1$-$C_4$ alkoxy, $C_2$-$C_4$ alkenyloxy, phenoxy, benzyloxy, amino, or Ar,
O—($C_2$-$C_9$ straight or branched chain alkenyl),
alkenoxy, alkoxy, alkylamino, alkylaryloxy, alkylthio, amido, amino, aminoalkyl, arylalkyloxy, aryloxy, benzyl, benzyloxy, $C_1$-$C_9$ alkoxy, $C_2$-$C_9$ alkenyloxy, $C_3$-$C_8$ cycloalkyl, $C_5$-$C_7$ cycloalkenyl, carboxy, cyano, ester, formanilido, halo, hydrogen, isocyano, nitroso, O-benzyl, O-phenyl, phenoxy, phenyl, sulfonyl, sulfoxy, thioalkyl, thiocarbonyl, thiocyano, thioester, thioformamido, trifluoromethoxy and Ar;
wherein Ar is an alicyclic or aromatic, mono-, bi- or tricyclic, carbo- or heterocyclic ring, and the individual ring size is 5-8 members; wherein the heterocyclic ring has 1-4 heteroatom(s) independently selected from the group consisting of O, N, and S.

5. The process of claim 1, wherein said amino alcohol-based catalyst is Nugent's morpholino isoborneol ligand.

6. The process of claim 1, wherein said bis(sulfonamide) catalyst is selected from the group consisting of

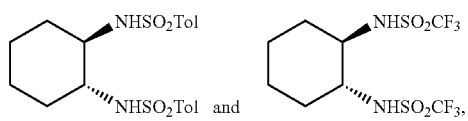

wherein said bis(sulfonamide) catalyst is used with $Ti(O^iPr)_4$ or $Ti(O^tBu)_4$ wherein Tol means p-tolyl.

7. The process of claim 1, wherein said oxidant is selected from the group consisting of dioxygen, tert-butyl hydroperoxide, and hydroperoxides of formula ROOH, R is an alkyl moiety.

8. The process of claim 1, wherein said transition metal catalyst is selected from the group consisting of $VO(acac)_2$, $Ti(O^iPr)_4$, and $Ti(O^tBu)_4$.

9. The process of claim 1 for making an acyclic epoxy alcohol, comprising the steps of:

(a) adding a first organozinc compound to an aldehyde in the presence of a first catalyst selected from the group consisting of Nugent's morpholino isoborneol ligand,

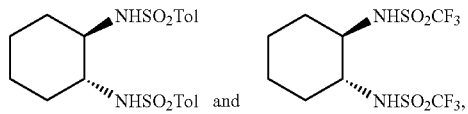

wherein said first catalyst additionally comprises $Ti(O^iPr)_4$ when a bis(sulfonamide) is used, to form an allylic alkoxide compound; and (b) epoxidizing said allylic alkoxide compound in the presence of diethylzinc, an oxidant selected from the group consisting of dioxygen and tert-butyl hydroperoxide, and a second catalyst selected from the group consisting of $VO(acac)_2/Ti(O^iPr)_4$ and $Ti(O^tBu)_4$ wherein Tol means p-tolyl.

10. The process of claim 9, wherein said first organozinc compound is dimethylzinc and said first catalyst is selected from the group consisting of

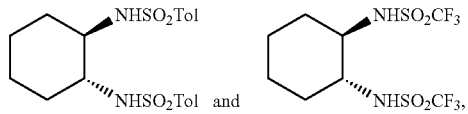

in combination with $Ti(O^iPr)_4$ or $Ti(O^tBu)_4$ wherein Tol means p-tolyl.

11. The process of claim 1 for making an acyclic epoxy alcohol, comprising the steps of:

(a) adding a divinylzinc compound to a aldehyde in the presence of a first catalyst selected from the group consisting of Nugent's morpholino isoborneol ligand,

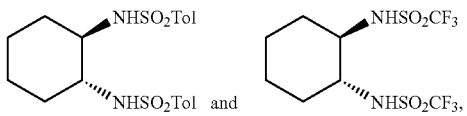

to form an allylic alkoxide compound; and (b) epoxidizing said allylic alkoxide compound in the presence of an oxidant selected from the group consisting of dioxygen and tert-butyl hydroperoxide, and a second catalyst selected from the group consisting of VO(acac)$_2$, Ti(O$^i$Pr)$_4$ and Ti(O$^t$Bu)$_4$.

12. The process of claim 1 for making an allylic epoxy alcohol, comprising the steps of:

(a) adding a trans-disubstituted divinylzinc compound and an organozinc compound to an α,β-unsaturated aldehyde in the presence of a first catalyst selected from the group consisting of

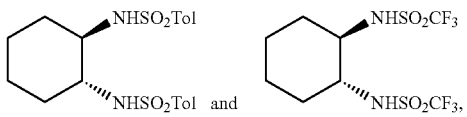

to form a bis(allylic alkoxide) compound; and (b) epoxidizing said bis(allylic alkoxide) compound in the presence of an oxidant selected from the group consisting of dioxygen and tert-butyl hydroperoxide, and a second catalyst selected from the group consisting of VO(acac)$_2$, Ti(O$^i$Pr)$_4$ and Ti(O$^t$Bu)$_4$ wherein Tol means p-tolyl.

13. The process of claim 12, wherein said trans-disubstituted vinylzinc compound is optionally synthesized in situ by a hydroboration/transmetalation reaction of a terminal alkyne with an enal of the formula:

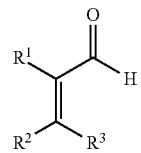

wherein R$^1$, R$^2$, and R$^3$ are independently selected from the group consisting of:

hydrogen, straight or branched chain C$_1$-C$_9$ alkyl, straight or branched chain C$_1$-C$_9$ alkyl substituted with at least one halo, trifluoromethyl, C$_1$-C$_6$ straight or branched chain alkyl, C$_2$-C$_6$ straight or branched chain alkenyl, benzyloxy, amino or Ar, O—(C$_1$-C$_9$ straight or branched chain alkyl), straight or branched chain C$_2$-C$_9$ alkenyl or alkynyl, and straight or branched chain C$_2$-C$_9$ alkenyl or alkynyl substituted with one or more halo, trifluoromethyl, C$_1$-C$_6$ straight or branched chain alkyl, C$_2$-C$_6$ straight or branched chain alkenyl, C$_1$-C$_4$ alkoxy, C$_2$-C$_4$ alkenyloxy, phenoxy, benzyloxy, amino or Ar, alkylamino, alkylaryloxy, alkylthio, amido, amino, arylalkyloxy, aryloxy, benzyloxy, C$_1$-C$_9$ alkoxy, C$_2$-C$_9$ alkenyloxy, C$_3$-C$_8$ cycloalkyl, C$_5$-C$_7$ cycloalkenyl, carboxy, cyano, ester, formanilido, halo, hydrogen, isocyano, nitroso, O-benzyl, O-phenyl, phenoxy, phenyl, sulfonyl, sulfoxy, thioalkyl, thiocarbonyl, thiocyano, thioester, thioformamido, trifluoromethoxy, and Ar, wherein Ar is an alicyclic or aromatic, mono-, bi- or tricyclic, carbo- or heterocyclic ring, the individual ring size is 5-8 members; and wherein the heterocyclic ring has 1-4 heteroatom(s) independently selected from the group consisting of O, N, and S, said enal being substituted at the R$^2$ or R$^3$ position, to generate said bis(allylic alkoxide) compound.

* * * * *